(12) United States Patent
Adachi et al.

(10) Patent No.: US 8,398,551 B2
(45) Date of Patent: Mar. 19, 2013

(54) CAPACITIVE ULTRASONIC TRANSDUCER, PRODUCTION METHOD THEREOF, AND CAPACITIVE ULTRASONIC PROBE

(75) Inventors: Hideo Adachi, Iruma (JP); Yukihiko Sawada, Tokorozawa (JP); Katsuhiro Wakabayashi, Hachioji (JP); Akiko Mizunuma, Hachioji (JP); Takuya Imahashi, Kawasaki (JP); Etsuko Omura, Saitama (JP); Yoshiyuki Okuno, Fussa (JP); Shuji Otani, Oume (JP); Miyuki Murakami, Hino (JP); Kiyoshi Nemoto, Hino (JP); Kozaburo Suzuki, Hachioji (JP); Naomi Shimoda, Fukushima (JP)

(73) Assignee: Olympus Corporation, Tokyo (JP)

( * ) Notice: Subject to any disclaimer, the term of this patent is extended or adjusted under 35 U.S.C. 154(b) by 302 days.

(21) Appl. No.: 12/027,168

(22) Filed: Feb. 6, 2008

(65) Prior Publication Data

US 2008/0139946 A1    Jun. 12, 2008

Related U.S. Application Data

(60) Division of application No. 11/633,399, filed on Dec. 4, 2006, now abandoned, which is a continuation of application No. PCT/JP2005/010163, filed on Jun. 2, 2005.

(30) Foreign Application Priority Data

| Jun. 3, 2004 | (JP) | ................. 2004165934 |
| Jun. 8, 2004 | (JP) | ................. 2004170334 |
| Jun. 14, 2004 | (JP) | ................. 2004176040 |
| Jun. 18, 2004 | (JP) | ................. 2004181521 |

(51) Int. Cl.
    *A61B 8/00* (2006.01)

(52) U.S. Cl. ........ 600/443; 600/407; 600/437; 600/459; 600/444

(58) Field of Classification Search ................. 600/407, 600/437, 443, 459, 444
See application file for complete search history.

(56) References Cited

U.S. PATENT DOCUMENTS

| 5,494,038 A | * | 2/1996 | Wang et al. ................. 600/459 |
| 6,159,149 A | * | 12/2000 | Erikson et al. ................. 600/437 |
| 6,314,057 B1 | | 11/2001 | Solomon et al. |
| 6,504,286 B1 | * | 1/2003 | Porat et al. ................. 310/324 |

(Continued)

FOREIGN PATENT DOCUMENTS

| EP | 1 482 313 A1 | 12/2004 |
| JP | 02-117299 A | 5/1990 |

(Continued)

OTHER PUBLICATIONS

Huang Y. et al "Fabricating Capacitive Micromachined Ultrasonic Transducers With Wafer-Bonding Technology", Journal of Microelectromechanical Systems 12(2):128-137 (2003).

(Continued)

*Primary Examiner* — Brian Casler
*Assistant Examiner* — Joel Lamprecht
(74) *Attorney, Agent, or Firm* — Scully, Scott, Murphy & Presser, P.C.

(57) ABSTRACT

It becomes possible to obtain high sound pressure in a high frequency domain by a capacitive ultrasonic transducer which comprises a membrane on which one electrode is formed, a cavity constructed in its backface, and a substrate on which these are mounted and supported and on whose surface an electrode is provided, on a surface in an ultrasonic transmission and reception side, characterized in that the membrane comprises tow or more layers, and at least one layer of them comprises a high dielectric constant film.

24 Claims, 31 Drawing Sheets

U.S. PATENT DOCUMENTS

| | | |
|---|---|---|
| 6,558,330 B1 | 5/2003 | Ayter et al. |
| 6,592,525 B2 | 7/2003 | Miller et al. |
| 2005/0043625 A1 * | 2/2005 | Oliver et al. .................. 600/459 |
| 2005/0088189 A1 | 4/2005 | Yanagisawa et al. |

FOREIGN PATENT DOCUMENTS

| | | |
|---|---|---|
| JP | 11/233733 | 8/1999 |
| JP | 2002-266082 | 9/2002 |
| JP | 2004-503312 | 2/2004 |
| WO | PCT/EP2001/006868 | 6/2001 |
| WO | WO 03/067268 A1 | 8/2003 |

OTHER PUBLICATIONS

Japanese Office Action dated Oct. 18, 2011, in counterpart Japanese Patent Application No. 2009-125886.

* cited by examiner

FIG.1A
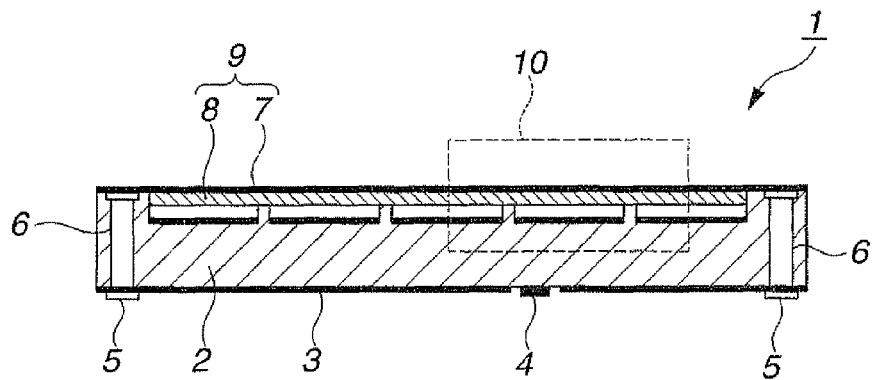
FIG.1B
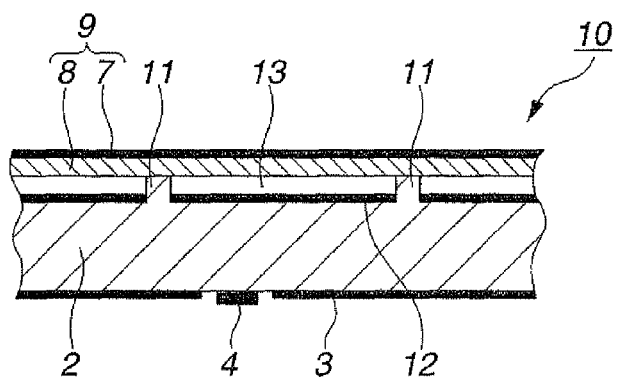
FIG.2A
BEFORE JUNCTION
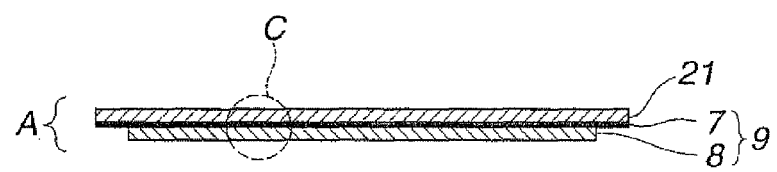
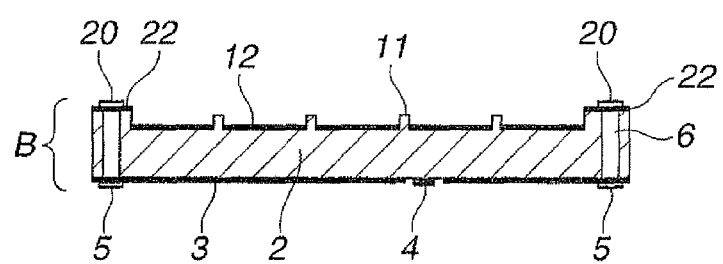

JUNCTION

SUBSTRATE REMOVAL

ADDITION OF SACRIFICE LAYER

ADDITION OF INSULATING LAYER

ADDITION OF UPPER ELECTRODE LAYER

REMOVAL OF SACRIFICE LAYER

ANODE JUNCTION

ALIGNMENT OF ANODE JUNCTION

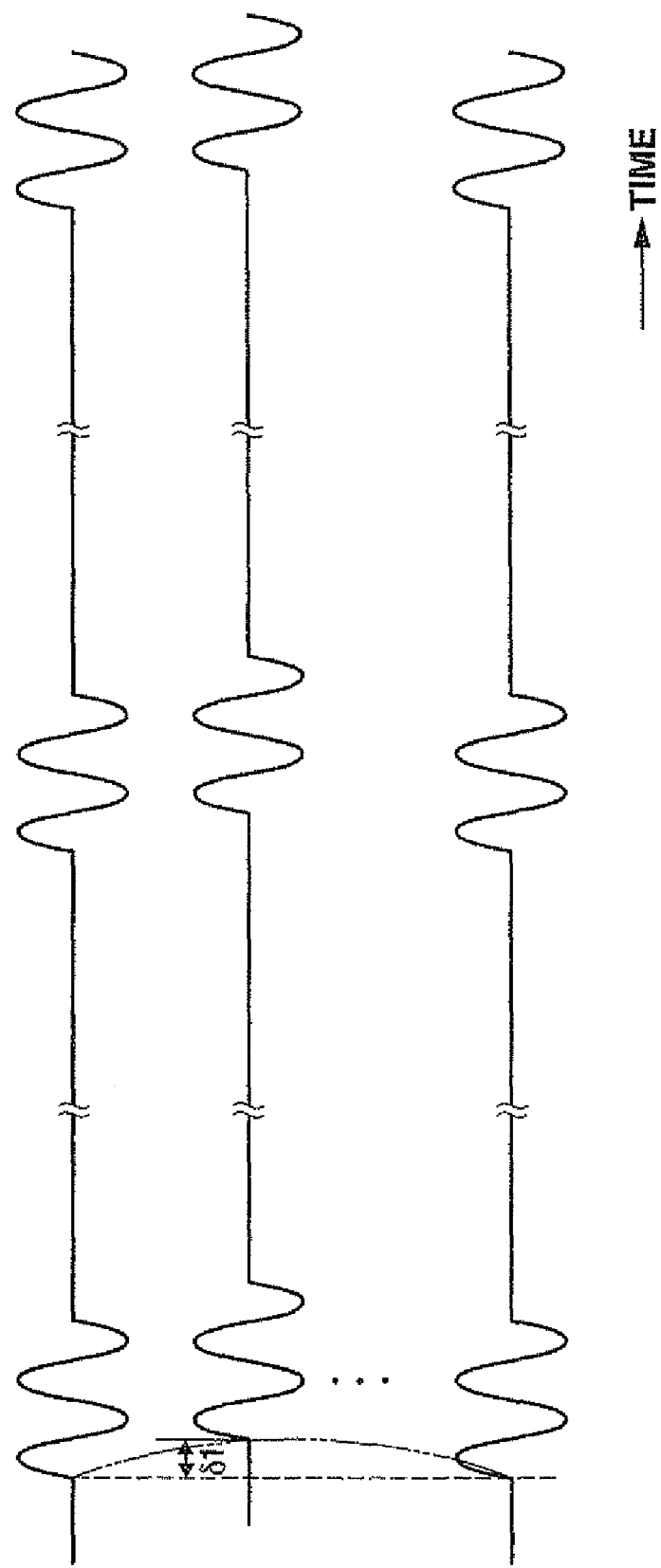

CAPACITIVE ULTRASONIC TRANSDUCER, PRODUCTION METHOD THEREOF, AND CAPACITIVE ULTRASONIC PROBE

CROSS REFERENCE TO RELATED APPLICATION

This application is a divisional application of U.S. application Ser. No. 11/633,399 filed on Dec. 4, 2006 now abandoned, which is a continuation application of PCT/JP2005/010163 filed on Jun. 2, 2005 and claims benefit of Japanese Applications No. 2004-165934 filed in Japan on Jun. 3, 2004, No. 2004-170334 filed in Japan on Jun. 8, 2004, No. 2004-176040 filed in Japan on Jun. 14, 2004 and No. 2004-181521 filed in Japan on Jun. 18, 2004, the entire contents of each of which are incorporated herein by their reference.

BACKGROUND OF THE INVENTION

1. Field of the Invention

The present invention relates to a capacitive ultrasonic transducer, into which a silicon semiconductor substrate is processed using a silicon micromachining technique, and its production method, and to a capacitive ultrasonic probe comprising the capacitive ultrasonic transducer in an end portion of an insertion section inserted into a body cavity.

2. Description of the Related Art

An ultrasonic diagnosis of diagnosing by radiating an ultrasonic wave into a body cavity, and visualizing a state in a living body from its echo signal has spread. There is an ultrasonic endoscope as one of equipment and materials used for this ultrasonic diagnosis. In the ultrasonic endoscope, an ultrasonic transducer is mounted at an end of an insertion section inserted into a body cavity, and this transducer converts an electric signal into an ultrasonic wave, radiates into the body cavity and receives an ultrasonic wave reflected in the body cavity, and converts it into an electric signal.

Heretofore, although a ceramic piezoelectricity material PZT (lead zirconate titanate) has been used in an ultrasonic transducer as a piezoelectric element which converts an electric signal into an ultrasonic wave, a capacitive ultrasonic transducer (Capacitive Micromachined Ultrasonic Transducer (called a c-MUT)) into which a silicon semiconductor substrate is processed using a silicon micromachining technique attracts attention. This is one of elements generically named a micromachine (MEMS: Micro Electro-Mechanical System).

The MEMS element is formed as a fine structure member on a substrate, such as a silicon substrate or a glass substrate, and is an element made by combining a driver which outputs a mechanical drive force, a drive mechanism which drives the driver, a semiconductor integrated circuit which controls the drive mechanism, and the like electrically and further mechanically. A fundamental feature of the MEMS element is that the driver constructed as mechanical structure is incorporated into a part of the element, and drive of the driver is performed electrically by applying a Coulomb attraction between electrodes or the like.

Now, the capacitive ultrasonic transducer (c-MUT) is an element of two electrodes standing with facing each other, there is a cavity in between them, and when an AC signal superimposed on an DC bias is applied, a layer (membrane) including one electrode between them vibrates harmonically to generate an ultrasonic wave.

For example, a method of producing the c-MUT using wafer-boding technology is disclosed in prior art (Yongli Huang and four others, "Fabricating Capacitive Micromachined Ultrasonic Transducers With Wafer-Boding Technology", JOURNAL OF MICROELECTROMECHANICAL SYSTEMS, VOL. 12, NO. 2, p. 128-p. 137, April, 2003. In this antecedent, the transducer is produced by forming a membrane and cavities on an SOI (Silicon On Insulator) wafer and a prime wafer respectively, and bonding those wafers using a silicon direct bonding technique in vacuum.

Ultrasonic transmission pressure P of a capacitive ultrasonic transducer is expressed as follows:

$$P = -\in r \times 8.854 e^{-12} \times W^2/d^2 \times V^2$$

where
  $\in r$: dielectric constant of material between electrodes
  $W^2$: electrode area
  $d$: distance between electrodes
  $V$: applied voltage In addition, a center frequency fc is expressed as follows:

$$fc = (\pi/2) \times (tm/W^2)(E/12\rho)^{1/2}$$

where
  tm: thickness of membrane
  E: Young's modulus
  $\rho$: density

Hence, although enlarging the electrode area $W^2$ enlarges transmitted ultrasonic sound pressure, it causes decrease of the center frequency at the same timer and hence, it was extremely difficult to obtain high sound pressure in a high frequency domain.

In addition, heretofore, production of a capacitive ultrasonic transducer was not easy in an economic aspect. Furthermore, when using a capacitive ultrasonic transducer for an ultrasonic endoscope, it is necessary to radiate an ultrasonic wave with an acoustic impedance near an acoustic impedance of a tissue in a body cavity.

Recent years, although an ultrasonic transducer has been widely used for acoustic diagnosis and a piezoelectric element using piezoelectricity has been usually used for this ultrasonic transducer, the capacitive ultrasonic transducer mentioned above is proposed recently.

For example, a theoretical structural example of a capacitive ultrasonic transducer is disclosed in National Publication of International Patent Application No. 2004-503312. Since sensitivity of a capacitive ultrasonic transducer is low, it is desired to be able to make it more highly sensitive.

For this reason, a capacitive ultrasonic transducer with specific structure, that is, layered structure is disclosed in U.S. Pat. No. 6,558,330.

On the other hand, harmonic imaging diagnosis using a harmonic signal is becoming standard diagnostic modality because of a clear diagnostic image which is not obtained by conventional B mode diagnosis recently.

The harmonic imaging diagnosis is classified into (1) a tissue harmonic imaging method which splits by various methods harmonics which are influenced by nonlinearity of a living body tissue and superimposed on a fundamental ultrasonic wave when an ultrasonic wave spreads an inside of a tissue, and performs visualization using this signal, and (2) a contrast harmonic imaging method which injects contrast medium bubbles into an inside of a body, receives harmonics generated when the bubbles explode or resonate by radiation of a transmitted ultrasonic wave, splits the harmonics superimposed on a fundamental ultrasonic wave by various methods, and performs visualization using this signal.

It turns out that all of these have such a good S/N that cannot be obtained by a conventional B mode tomogram and that a diagnostic image with a satisfactory resolution is obtained, and they contribute to enhancement in diagnostic accuracy of medical diagnosis.

As for an ultrasonic transducer used for a conventional harmonic imaging diagnostic apparatus for an outside of a body, for example, the same ultrasonic transducer serving both for transmission and reception has been used also for fundamental wave transmission and harmonics reception. In addition, construction of receiving an echo of an ultrasonic pulse reflected from a living body tissue with an ultrasonic transducer provided separately from that for transmission is also possible.

Since a signal level of a harmonic signal is far small in comparison with a fundamental wave, it is necessary to remove efficiently a fundamental wave component in connection with degradation of a harmonic image. Therefore, harmonic component (in particular, second harmonic component) extraction technique which is widely known is used.

As ultrasonic transducers, besides a conventional piezoelectric ultrasonic transducer, the above-mentioned capacitive ultrasonic transducer into which a silicon semiconductor substrate is processed using a silicon micromachine technique attracts attention.

As for the capacitive ultrasonic transducer, it is said that, generally, in order to generate an ultrasonic wave, not only a high frequency pulse signal, but also a DC bias voltage is required at the time of both of reception and transmission. In short, it is performed to generate a signal that the high frequency pulse signal is superimposed on the DC bias voltage, to apply it to the capacitive ultrasonic transducer, and to transmit and receive the ultrasonic wave by it.

By the way, since the capacitive ultrasonic transducer conventionally having been proposed has an ultrathin membrane thickness, it reflects acoustic impedance of a cavity, and hence, it is suitable for air ultrasonic waves.

A capacitive ultrasonic probe apparatus aiming at use outside a body is disclosed in the above-mentioned National Publication of International Patent Application No. 2004-503312.

In order to use a harmonic imaging technique, an ultrasonic transducer with a wide band characteristic is necessary, but since the capacitive ultrasonic transducer has a wide band characteristic, it is suitable for harmonic imaging diagnosis. In addition, in the case of a conventional capacitive ultrasonic transducer, since intensity of an ultrasonic beam is small, many capacitive ultrasonic transducer elements are used and ultrasonic beams transmitted by these are focused electronically.

SUMMARY OF THE INVENTION

A capacitive ultrasonic transducer according to the present invention is characterized by comprising: a first electrode, a second electrode which faces the first electrode and is arranged with keeping a predetermined gap, and a high dielectric constant film which is formed on a surface of at least one electrode of the above-mentioned electrodes, and the surface which faces another one of the above-mentioned electrodes.

The above-mentioned high dielectric constant film includes at least any one among barium titanate, strontium titanate, a solid solution of barium and titanate strontium, and niobium oxide stabilized tantalum pentoxide.

The above-mentioned high dielectric constant film is characterized by including at least any one among tantalum oxide, aluminum oxide, and titanium oxide.

The above-mentioned capacitive ultrasonic transducer is characterized by being constructed using a substrate made of silicon single crystal or glass.

A production method of a capacitive ultrasonic transducer according to the present invention is a production method of a capacitive ultrasonic transducer comprising a first electrode, a second electrode which faces the first electrode and is arranged with keeping a predetermined gap, and a high dielectric constant film which is given on a surface of at least one electrode of the above-mentioned electrodes and the surface which faces another one of the above-mentioned electrodes, characterized by comprising: a stacked layer forming step of performs stacked layer formation of one or more layers including the above-mentioned first electrode and high dielectric constant film on a first substrate, a cavity forming step of forming cavities in a second substrate for forming the cavities which are spaces between the above-mentioned first electrode and the above-mentioned second electrode, an electrode forming step of forming a second electrode in bottom sections of the above-mentioned cavities, a bonding step of bonding a surface in a stacked layer formation side of the above-mentioned first substrate, on which the above-mentioned stacked layer formation is performed, with a convex section surface of the above-mentioned second substrate, and a substrate removing step of removing the first substrate from the above-mentioned first substrate on which the above-mentioned stacked layer formation is performed.

It is characterized by using an anode bonding method at the above-mentioned bonding step.

It is characterized in that the above-mentioned high dielectric constant film is formed on the above-mentioned first electrode by performing reduction and oxidation after making a metal alkoxide compound solution of tantalum, titanium, and barium coated and performing a sol-gel method.

A production method of a capacitive ultrasonic transducer according to the present invention is a production method of a capacitive ultrasonic transducer comprising a first electrode, a second electrode which faces the first electrode, and is arranged with keeping a predetermined gap, and a high dielectric constant film which is given on a surface of at least one electrode of the above-mentioned electrodes and the surface which faces another one of the above-mentioned electrodes, characterized by comprising: a cavity forming step of not only forming cavities in a second substrate for forming the cavities which are spaces between the above-mentioned first electrode and the above-mentioned second electrode, but also forming the second electrode in the bottom sections of the above-mentioned cavities, a sacrifice layer forming step of forming a sacrifice layer by making the above-mentioned cavities of the above-mentioned second substrate filled with a resist agent, a high dielectric constant film forming step of forming one or more films, including the above-mentioned high dielectric constant film, on a surface of a side of the above-mentioned second substrate where is filled with the above-mentioned resist agent, an electrode forming step of forming the above-mentioned first electrode on the above-mentioned film, and a sacrifice layer removing step of making holes penetrate the above-mentioned first electrodes and the above-mentioned film, and removing the above-mentioned sacrifice layer from the holes.

It is characterized in that the above-mentioned second substrate comprises two substrates of a glass substrate and a silicon substrate, one or more holes for forming cavities in one substrate among the two substrates are provided, the above-mentioned second electrodes are provided only in positions corresponding to positions of the holes in another substrate, and the two substrates are bonded by anode bonding.

It is characterized by providing an ultrasonic endoscope apparatus equipped with the capacitive ultrasonic transducer described above.

It is characterized by providing an ultrasonic endoscope apparatus equipped with the capacitive ultrasonic transducer produced by the above-described production method.

In the above structure, high sound pressure can be obtained in a high frequency domain by using the capacitive ultrasonic transducer according to the present invention. In addition, since it is possible to produce it by a simple production method, it is to aim at cost reduction. Furthermore, since it becomes easy for ultrasonic vibration of a membrane to conduct a tissue, sensitivity improves as a result.

A capacitive ultrasonic transducer according to the present invention is characterized by having structure of not only arranging capacitive ultrasonic transducer cells, which are constructed of a substrate and electrodes formed on the above-mentioned substrate, a membrane constructed at a distance from an air-gap layer, membrane support members for constructing the above-mentioned membrane on the above-mentioned substrate at a distance from an air-gap layer, and electrodes formed on the membrane, two-dimensionally along with an in-plane of the above-mentioned substrate, but also stacking and arranging them vertically to the above-mentioned substrate.

Because of the above-mentioned structure, the capacitive ultrasonic transducer array with high sensitivity is achieved by not only making the capacitive ultrasonic transducer cells into layered structure, but also making them into the structure of further arranged two-dimensionally in a plane surface of the substrate.

A production method of a capacitive ultrasonic transducer according to the present invention is characterized by not only comprising: a first step of forming an insulating layer on an upper face of a semiconductor substrate and forming a first electrode layer on its upper face, a second step of forming a temporary layer for cavity formation on an upper face of this first electrode layer, a third step of forming masks corresponding to portions, where cavities are formed, on the above-described temporary layer so as to make them arranged two-dimensionally, a fourth step of forming concavities reaching the above-mentioned first electrode layer by removing portions, to which the above-mentioned masks are not given, by etching and the like, a fourth step of removing the above-mentioned masks and exposing the temporary layer, a fifth step of forming a film covering the above-described temporary layer while filling the above-mentioned concavities, a sixth step of forming holes which penetrate the above-mentioned film and reach the above-described temporary layer, a seventh step of removing the above-described temporary layer by etching or the like using the above-mentioned holes, an eighth step of forming a membrane layer on an upper face of the above-mentioned film, a ninth step of forming a second electrode layer on an upper face of the above-mentioned membrane layer, and a tenth step of repeating the above-mentioned second step to ninth step once or more on the above-mentioned second electrode layer, but also forming upper side masks with shifting them so as to become positions between two just lower layers of masks when forming them at that time.

In the above structure, by using the capacitive ultrasonic transducer according to the present invention, since not only capacitive ultrasonic transducer cells are made into layered structure, but also they are made into the structure of further arranged two-dimensionally in a plane surface of the substrate, it is possible to achieve a capacitive ultrasonic transducer array with high sensitivity.

A capacitive ultrasonic probe according to the present invention is a capacitive ultrasonic probe for medical diagnoses, and is characterized by having acoustic matching means of performing acoustic matching of both acoustic impedances between an acoustic impedance of a tissue, and an acoustic impedance of ultrasonic transducer cells which construct the capacitive ultrasonic probe.

The above-mentioned capacitive ultrasonic probe has a capacitive ultrasonic transducer, and a sheath which includes this capacitive ultrasonic transducer, and is characterized in that the above-mentioned acoustic matching means is arranged in a sheath side.

It is characterized in that an air layer intervenes between a surface of the above-mentioned capacitive ultrasonic transducer, and the above-mentioned sheath.

It is characterized in that the above-mentioned acoustic matching means is formed in a cavity which is a component of a capacitive ultrasonic transducer cell.

It is characterized in that the above-mentioned acoustic matching means is a multi-fine elastic pillar.

It is characterized in that conductive films are uniformly formed on surfaces of the multi-fine elastic pillar.

It is characterized in that the above-mentioned acoustic matching means has a distribution characteristic in an acoustic impedance within a surface of an ultrasonic transducer cell.

It is characterized in that the above-mentioned acoustic matching means comprises a concavoconvex protective film horn.

It is characterized in that the above-mentioned concavoconvex protective film horn is a sheet with folding lines which spread in a whole ultrasonic transducer element.

It is characterized in that a lower crown of the above-mentioned concavoconvex protective film horn is arranged and connected so as to contact to a center portion of an ultrasonic transducer cell.

It is characterized in that the above-mentioned acoustic matching means is arranged with intervening between a membrane, which is a component of a capacitive ultrasonic transducer cell, and an object.

It is characterized in that the above-mentioned acoustic matching means comprises at least one layer of acoustic matching layer which performs impedance matching between an apparent acoustic impedance at the time of seeing the membrane, and an acoustic impedance of a tissue.

It is characterized in that the above-mentioned acoustic matching means comprises two layers, their first layer is made of a porous resin, and their second layer is made of a homogeneous resin material which is the same material as that of the first layer, but does not include holes.

It is characterized in that the above-mentioned resin material is any one or a composite resin of a silicone resin, an urethane resin, an epoxy resin, a Teflon® resin, and a polyimide resin.

It is characterized by having structure of an air layer intervening between the above-mentioned acoustic matching means and membrane.

It is characterized by Helmholtz resonator structure intervening between the above-mentioned acoustic matching means and membrane.

It is characterized in that the above-mentioned acoustic matching means is means of changing an apparent acoustic impedance at the time of seeing the membrane.

It is characterized in that means of changing the above-mentioned apparent acoustic impedance is a sound medium arranged between an upper electrode and a lower electrode.

It is characterized in that a sound medium arranged between the above-mentioned upper electrode and lower electrode has an acoustic impedance having a value of 0.5 to 3.0 Mrayl.

In the above structure, the following acoustic matching means a), b), or c) is provided as means of performing acoustic matching of the capacitive ultrasonic transducer to a tissue.

a) To provide means of increasing an acoustic impedance of a cavity for a cavity section. For example, pillar-shaped rod, porous silicon, and porous resin.

b) To construct a folded convexoconcave protective layer film, acting for an acoustic transformation horn sheet, per element on a membrane.

c) To form an internal membrane so that a cavity section may be divided, and to take acoustic matching by multi-layer structure of the internal membrane/divided cavities/an acoustic matching layer (one or more layer)/a tissue or water.

In the above structure, by using the capacitive ultrasonic transducer according to the present invention, it is possible to achieve a capacitive ultrasonic probe, which can achieve acoustic matching with a tissue efficiently, has a low effective drive voltage, can be used in a body cavity, is easily processed and assembled, can secure chemical resistance, can reduce loss by a coaxial cable, and is available to the harmonic imaging diagnosis, by using a capacitive ultrasonic transducer.

The capacitive ultrasonic probe according to the present invention is characterized by forming focusing means of focusing ultrasonic beams structurally by a curvature membrane section made by making the above-mentioned membrane section, which constructs the above-mentioned capacitive ultrasonic transducer, a curvature in a capacitive ultrasonic probe which embeds the capacitive ultrasonic transducer which transmits and receives an ultrasonic wave by vibration of the membrane section. In the above-mentioned structure, by focusing ultrasonic beams structurally by the curvature membrane section, it becomes possible to enlarge intensity of the ultrasonic beams transmitted in simple structure, and hence, it is made to be able to obtain a received signal with a good S/N.

A capacitive ultrasonic transducer according to the present invention is driven by a driving signal, and a shape of the driving signal applied to the capacitive ultrasonic transducer is composed of superimposed waves of a rf pulse and a dc pulse whose period is longer than the period of the rf pulse.

BRIEF DESCRIPTION OF THE DRAWINGS

FIG. 1A is a diagram showing basic structure of an capacitive ultrasonic transducer in a first embodiment of the present invention;

FIG. 1B is an enlarged diagram of a portion surrounded by a broken line in FIG. 1A;

FIG. 2A is a diagram showing a state before bonding in the production process of the capacitive ultrasonic transducer in the first embodiment;

FIG. 7B includes charts showing RF signals generated by the transmitted beam former in FIG. 6;

DETAILED DESCRIPTION OF THE PREFERRED EMBODIMENT(S)

Figure 2B:
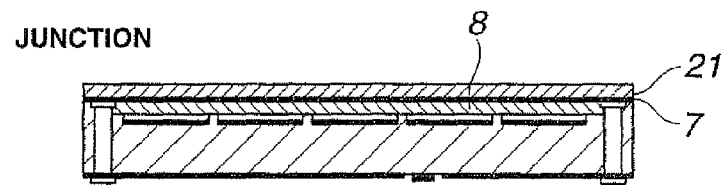
FIG. 2B is a diagram showing a state after bonding in the production process of the capacitive ultrasonic transducer in the first embodiment.

Hereafter, embodiments of the present invention will be explained with reference to drawings

First Embodiment

FIGS. 1A and 1B show basic structure of a capacitive ultrasonic transducer (c-MUT) 1 in this embodiment. FIG. 1A shows a sectional view of the whole capacitive ultrasonic transducer. A unit of the capacitive ultrasonic transducer shown in this FIG. 1A is called an element. In the capacitive ultrasonic transducer, there is a plurality of concavities on a surface of a silicon substrate 2. This one unit is called a cell 10. A membrane 9 covers an upper face of the silicon substrate 2 so as to cover each cell 10. The membrane 9 is a thin film (high dielectric constant film) which comprises an upper electrode 7 and a high dielectric constant oxide layer 8 mentioned later.

In addition, an insulating layer 3 is provided on a backface of the silicon substrate 2. A backface electrode pad (contact pad) 4 is provided in a part of this insulating layer 3. Interconnect via holes 6 are located in both ends of the silicon substrate 2. A contact pad 5 is provided on one end (a backface side of the silicon substrate) of each interconnect via hole.

FIG. 1B is an enlarged diagram of a portion (cell) 10 surrounded by a broken line in FIG. 1A. The cell 10 supports the membrane 9 by membrane support members 11 in both ends of the each cell 10. In addition, a lower electrode 12 is arranged on a surface (a bottom part of a concavity) of the silicon substrate 2 between the membrane support members 11. Then, a cavity 13 comprises a space surrounded by the membrane 9, membrane support members 11, and lower electrode 12.

When an operation of a capacitive ultrasonic transducer 1 is explained, both electrodes pulls each other by applying a voltage to a pair of electrodes of the upper electrode 7 and lower electrode 12, and they return when the voltage is set at 0. An ultrasonic wave is generated by this vibrating motion and an ultrasonic wave is radiated in an upper direction of the upper electrode.

Then, a production process of the capacitive ultrasonic transducer 1 will be explained below.

Figure 2C:
FIG. 2C is a diagram showing a substrate removal state in the production process of the capacitive ultrasonic transducer in the first embodiment.

FIGS. 2A to 2C show the production process of the capacitive ultrasonic transducer in this embodiment. First, FIG. 2A will be observed. In this embodiment, what is expressed by the upper electrode 7, high dielectric constant oxide layer 8, and silicon layer 21 is called an upper unit A, and what is expressed by the silicon substrate 2 and the like is called a lower unit B. FIG. 2A shows respective states of the upper unit A and lower unit B before bonding.

The lower unit B will be explained. First, two or more concavities are formed by etching processing of a surface of the silicon substrate 2. This concavity has structure of being divided by the membrane support members 11. The lower electrode 12 is arranged on a bottom of this concavity. The interconnect via holes 6 are electroconductive channels which are provided by being made to penetrate the silicon substrate from the surface of the silicon substrate 2 to a backside. In addition, the membrane support members are obtained also by forming an insulating member of SiO2 and SiN as a film.

Convex portions of both ends in a topface side of the silicon substrate 2 are covered by the insulating layer 22. Bump pads (for example, solder balls or the like) 20 for bonding the upper electrode 7 later are attached to one end (a topface side of the silicon substrate 2) of the interconnect via hole 6. In addition, a contact pad 5 is provided on another end (a backface side of the silicon substrate 2) of the interconnect via hole 6. The contact pad 5 becomes a terminal in the backface side of the silicon substrate 2 for the upper electrode 7, when the upper electrode 7 is bonded to the silicon substrate 2 as mention later.

The insulating layer (for example, SiO2) 3 is formed on the backface of the silicon substrate 2, and the contact pad 4 is provided on its part. This contact pad 4 is a contact terminal to the lower electrode 12, and since a silicon material with small resistance is used for the silicon substrate 2, it can be conductive to the lower electrode 12 through this contact pad 4.

The insulating layer 3 is for insulating the contact pad 4 from the contact pad 5. Then, after bonding, it is possible to apply a voltage to the upper electrode 7 and lower electrode 12 from the backface side of the silicon substrate 2 respectively through the contact pad 4 and contact pad 5. Although the upper electrode 7 is led to a pad electrode through the interconnect via hole 6 by doing in this way for every element, it is insulated from the silicon substrate 2 with small resistance. On the other hand, since the lower electrode 12 and contact pad are conductive through the silicon substrate 2 with small resistance, both contact pads are insulated, and hence, it never occurs that a signal short-circuits.

Next, the upper unit A will be explained. The upper unit A comprises two or more layers, and an enlarged diagram of a stacked layer portion enclosed by a broken line in FIG. 2A is shown in FIG. 3.

Figure 3:
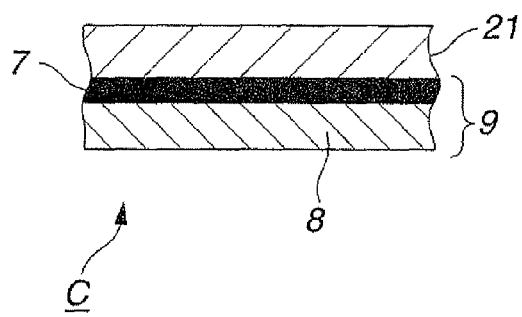
FIG. 3 is an enlarged diagram of a broken line portion in FIG. 2A.

FIG. 3 is an enlarged diagram of a broken line portion in FIG. 2A. In this embodiment, the upper unit A comprises a silicon layer 21 and the membrane 9 (a layer of the upper electrode 7, and the high dielectric constant oxide layer 8).

In the production process, the silicon layer 21 is for supporting this membrane 9 until the membrane 9 is bonded to the silicon substrate 2. Because, since the membrane 9 is in several micron order, it is a substrate for making such membrane easy to be dealt with in the production process.

The upper electrode 7 becomes a pair with the lower electrode 12 as mentioned above, and both electrodes pulls each other by applying a voltage to the pair of electrodes of the upper electrode 7 and lower electrode 12, and they return when the voltage is set at 0. An ultrasonic wave is generated by this vibrating motion and an ultrasonic wave is radiated in an upper direction of the upper electrode. As a material of the upper electrode 7, any one of Au/Ti, Au/Ni, Au/Cr, and Au/(Ni—Cr) is used.

The high dielectric constant oxide layer 8 is a layer formed in order to increase an electrostatic attraction working between the upper electrode 7 and lower electrode 12. The membrane which includes the upper electrode 7 vibrates by controlling a voltage applied to the upper electrode 7 and lower electrode 12 to generate an ultrasonic wave. Therefore, vibration becomes strong as the electrostatic attraction working between the upper electrode 7 and lower electrode 12 becomes strong. Then, it will be investigated to strengthen this electrostatic attraction. The following expression expresses an electrostatic attraction Fatt which works between the upper electrode 7 and lower electrode 12.

$$Fatt = -(1/2) \times \in r \times (W^2/d^2) \times V^2$$

where:
$\in r$: dielectric constant
$W^2$: electrode area
d: distance between electrodes
V: voltage From this formula, it turns out that the electrostatic attraction Fatt working between electrodes becomes large as the dielectric constant is high if d, $W^2$, and V are constant. Therefore, it is possible to strengthen the electrostatic attraction Fatt by making a substance with a large dielectric constant intervene between the upper electrode 7 and lower electrode 12, and what bears the role is just the high dielectric constant oxide layer 8.

Therefore, a material with a high dielectric constant is used for the high dielectric constant oxide layer 8. Then, in this embodiment, a material, which has a high dielectric constant, such as barium titanate BaTiO3 ($\in r$:1200), strontium titanate SrTiO3 ($\in r$:332), barium titanate strontium ($\in r$: according to an ionic ratio of barium and strontium, an intermediate value of barium titanate and strontium titanate is shown), tantalum pentoxide ($\in r$:27), niobium oxide stabilized tantalum pentoxide ($\in r$:27), aluminum oxide or titanium oxide TiO2 (r:100), tantalum oxide Ta2O3, or the like is used as the high dielectric constant oxide layer 8.

As for this upper unit A, first, an electrode film (upper electrode 7) is bonded (evaporated) on a surface of the silicon substrate 21, and the high dielectric constant oxide layer 8 is formed on it.

Next, FIG. 2B will be observed. This FIG. 2B is a step of bonding the upper unit A and lower unit B in FIG. 2A. When a surface of the upper unit A in a side of the high dielectric constant oxide layer 8 which are produced above, and a top-face side of the lower unit are aligned and heat is applied, the interconnect via holes 6 and upper electrode 7 are welded with the bump pads 20.

Next, FIG. 2C will be observed. A state in this FIG. 2C shows a state where etching processing removes the silicon substrate 21. As for the silicon substrate 21, it is possible to remove the silicon substrate 21 from the membrane 9 by performing etching processing, for example, using an alkaline etchant (for example, KOH). In addition, the etching processing is not limited other than this, for example, other etching processing generally used may be also sufficient. In addition, a part of thickness may be also left without etching the whole silicon substrate 21.

In addition, it is also sufficient to form an SiO2 film beforehand between the silicon substrate 21 and upper electrode 7. When advancing to this film, etching is stopped. Even if dispersion is in proceeding of the etching in the silicon substrate 21, it is possible to finally achieve the membrane with a uniform film thickness. Nevertheless, this SiO2 film remains with adhering to the membrane 9, and plays the role of mechanical and chemical reinforcement to the upper electrode 7 and high dielectric constant film 8. In addition, a reason why Au/Ti, Au/Cr, Au/Ni, or Au/(Ni—Cr) is used for the upper electrode 7 is because of securing adhesion to the silicon oxide film (SiO2 film). Since it is hard to form Au directly on the SiO2 film, Ti, Ni, Cr, or Ni—Cr is used as a buffer layer.

Now, a forming method of the above-described high dielectric constant oxide layer 8 will be explained in full detail. The high dielectric constant oxide layer 8 is formed by a sol-gel method. The sol-gel method is a method of starting from an organic metal compound solution, coating the solution to a substrate, making a sol where particulates of metal oxide or hydroxide disperse by hydrolyzing this coated film, making it a gel by further advancing a reaction, heating it to make amorphousness, glass, or polycrystal.

In this embodiment, the oxide layer formed by the sol-gel method is reduced and reoxidated to further increase the dielectric constant. A technique of increasing an apparent dielectric constant by this reduction and reoxidation step is used, for example, as a production technique of a boundary layer (BL) capacitor.

Then, the forming method of the high dielectric constant oxide layer 8 by the sol-gel method will be explained below.

S1: Form a layer of a film of the upper electrode 7 on the Si substrate 21.

S2: Coat a sol-gel precursor liquid, including metal alkoxide of tantalum, titanium, or barium on the film of the upper electrode 7.

S3: Make the sol-gel precursor liquid into a sol where particulates of metaled oxide or hydroxide is melted by hydrolysis, heat an amorphous film gelled by advancing the reaction further, and form a crystal. At this time, since there are various methods in hydrolysis, there are cases, such as adding additives for pH preparation, also when occurring only by H2O, and also when further adding additives of making the hydrolysis advance gradually, and hence, additives are used according to a situation. In addition, the sol generated in this intermediate phase is nano-scale particulates. Hence, the film made by gelling at this step is a nano particle film.

S4: Reduce the nano particle film formed above. As for reduction processing here, the nano particle film is exposed under a deoxidation air current for a predetermined time (for example, at 800 degrees for about 10 minutes). In addition, it is also sufficient to leave it under a low oxygen partial pressure gas or a vacuum for a predetermined time.

S5: Next, oxidize it again. As oxidation here, the nano particle film reduced at S4 is exposed under an oxygen-included air current such as the air for a predetermined time.

Then, it is possible to form the high dielectric constant oxide layer 8 made of particles in nano order on the upper electrode 7.

By doing in this way, it is possible to enlarge transmitted ultrasonic sound pressure by increasing the electrostatic attraction working between electrodes by forming the high dielectric constant oxide layer. In addition, decrease of a center frequency is never caused at this time. Hence, it is possible to obtain high sound pressure in a high frequency domain. In addition, it is also sufficient to form the high dielectric constant material layer in a lower electrode side. Also in this way, it is possible to heighten the electrostatic attraction. In addition, it is also sufficient that the membrane comprises two or more layers (for example, further forming two or more high dielectric constant material layers as films) including the high dielectric constant material layer and upper electrode.

In addition, it is also sufficient to bury cavities with high dielectric constant oxide in an extent of predetermined spaces being kept in the cavities. Because, since the vibration of the membrane is flexing vibration, when the electrostatic attraction acts, it is given flexion deformity to the cavity side, and hence, a space where this deformation can be performed freely is required. Furthermore, as mentioned later, in this embodiment, since there is no sacrifice layer step, it is also possible to aim at cost reduction.

Second Embodiment

An example of a method of fabricating a capacitive ultrasonic transducer with a resin-made cavity forming substrate will be described as the present embodiment. Here, a cavity will hereinafter refer to space between an upper electrode and a lower electrode and does not necessarily have to be hollow. In addition, a concave portion or porosity, which is produced in a process (intermediate stage) prior to becoming a cavity at the time of final fabrication will be also referred to as a cavity.

FIGS. 4A to 4E are drawings showing a fabrication process in the present embodiment. At first, an electrode 31 is formed on a surface of a silicon substrate. Next, on this silicon substrate 29, a supporting portion 28 is formed in a portion where no electrode 31 is disposed (a substrate comprising a silicon substrate 29, a supporting portion 28 and the electrode 31 will be referred to as a resin-made cavity forming substrate 30) (see FIG. 4A). Insulating material selected from the group consisting of SiN, $SiO_2$ and the like is used as the supporting portion 28.

Figure 4A:
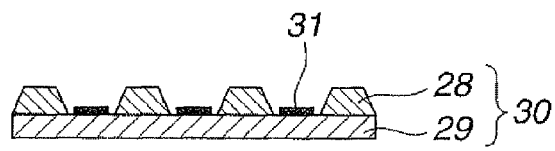
FIG. 4A is a diagram showing a resin substrate for cavity formation in a production process of an capacitive ultrasonic transducer in a second embodiment of the present invention.
Figure 4B:
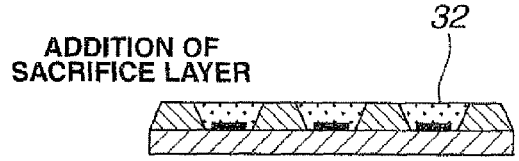
FIG. 4B is a diagram showing an addition state of a sacrifice layer in a production process of the capacitive ultrasonic transducer in the second embodiment.

As a result of forming the supporting portion 28, a sacrifice layer 32 is formed in the formed concave portion (see FIG. 4B). Photoresist material, for example, is used as material of the sacrifice layer 32. Photoresist material is photosensitive corrosion-resisting film material coated on a substrate at the time of drawing a circuit pattern on a semiconductor substrate. The fining process at the time of fabricating IC and LSI semiconductor devices is frequently carried out by adopting photolithography using the photoresist material as protection film.

Photoresist material is divided into a positive type and a negative type, resists in the exposed portion and the unexposed portion are dissolved and removed with developing liquid from the positive type and from the negative type respectively and a circuit pattern is left on the substrate. "TrisP-PA-MF" (produced by Honshu Chemical Industry Co., Ltd.) and "AZ 6100 series" (produced by Clariant (Japan) K. K.), for example, are nominated as such photoresist material.

The concave portion of the resin-made cavity forming substrate 30 is filled with such photoresist material. In order to form such a sacrifice layer, in the process to be described below, an insulating layer to become a membrane is brought into bonding with the surface (the side of a concave portion) of the resin-made cavity forming substrate 30, which is intended to allow no indentations and no wrinkles to appear in the portion located in the concave portion in the insulating layer at that time.

Figure 4C:
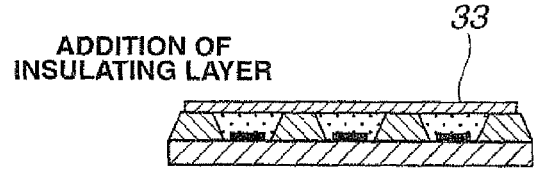
FIG. 4C is a diagram showing an addition state of an insulating layer in the production process of the capacitive ultrasonic transducer in the second embodiment.

Next, an insulating layer 33 being one of the layers forming the membrane is joined together with the surface (the concave portion side) of the resin-made cavity forming substrate 30 (see FIG. 4C). Polymer organic material such as polyimide, for example, is used as material for the insulating layer 33 hereof ("semiconductor surface protection film-interlayer insulating film positive type photosensitive heat resisting polyimide coating agent "Photoneeds PW-1000", for example).

Bonding is carried out with the ultrasonic bonding technology. Ultrasonic waves are radiated to resin and oscillation energy is intensified into the bonding portion, the oscillation energy is converted into friction heat to melt the resin and thereby resin-made cavity forming substrate 30 and resin-made insulating layer 33 are joined together. That method is advantageous in that no consumable supplies such as adhesive and the like are required at all. Here, bonding may be carried out with adhesive.

Figure 4D:
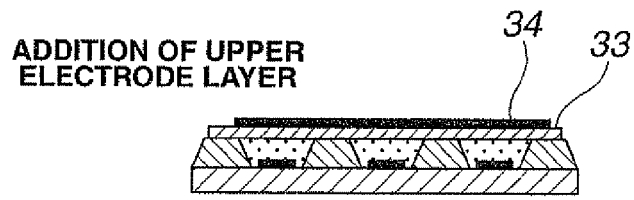
FIG. 4D is a diagram showing an addition state of an upper electrode layer in the production process of the capacitive ultrasonic transducer in the second embodiment.

Next, an upper electrode layer 34 is given to the surface of the insulating layer 33 (see FIG. 4D). Au/Cr, for example, is used as material for the upper electrode layer 34 and that is evaporated onto the surface of the insulating layer 33.

Figure 4E:
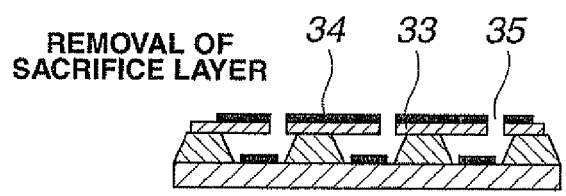
FIG. 4E is a diagram showing a removal state of the sacrifice layer in the production process of the capacitive ultrasonic transducer in the second embodiment.

Lastly, the upper electrode layer 34 and the insulating layer 33 are provided with a hole 35 (a sacrifice layer removal hole) and dipped in solvent such as acetone and then acetone penetrates in to dissolve the photoresist and the dissolved photoresist gets out of the hole so that the sacrifice layer is removed and a cavity (hollow) is formed (see FIG. 4E).

Here, the membrane may be configured by a plurality of layers including insulating layer 33 and electrode 34 (a plurality of insulating layers are filmed further and the like, for example).

The present embodiment is advantageous as follows. As material of an insulating layer, material with acoustic impedance which is comparatively close to that of a living subject such as polyimide is more preferable than TiO2 and SiNx with large acoustic impedance in order to improve acoustic matching with a living subject. Film thickness in this case is several tens of micrometers, wrinkles will appear in a portion to become a membrane with the method of bringing film into bonding. Accordingly, resist material easily dissolvable to solvent, for example, is implanted into a concave portion; subsequently the surface undergoes smoothing processing with means such as grinding so as to give uniformity to the surface; resin film selected from the group consisting of polyimide, silicone, parylene, urethane and the like is evaporated from thereabove and formed with spin coating and spray coating; and thereafter resist material being sacrifice layer material is removed through the sacrifice layer removal hole. Thus formed membrane film lacks wrinkles and is provided with acoustic impedance close to that of a living subject, which will improve acoustic matching with the living subject and lead to improvement in sensitivity as a result thereof.

Third Embodiment

A method of fabricating a capacitive ultrasonic transducer with the anode bonding technology will be described in the present embodiment. The anode bonding technology refers to a technology of applying direct voltage of several hundreds of volts under several hundreds of ° C. and employing Si—O covalent bond to stick a silicon surface and a glass surface together. For the present embodiment, a cavity is formed with die forming in use of the technology hereof. Glass is glass including movable ions such as sodium ions and the like.

Figure 5A:
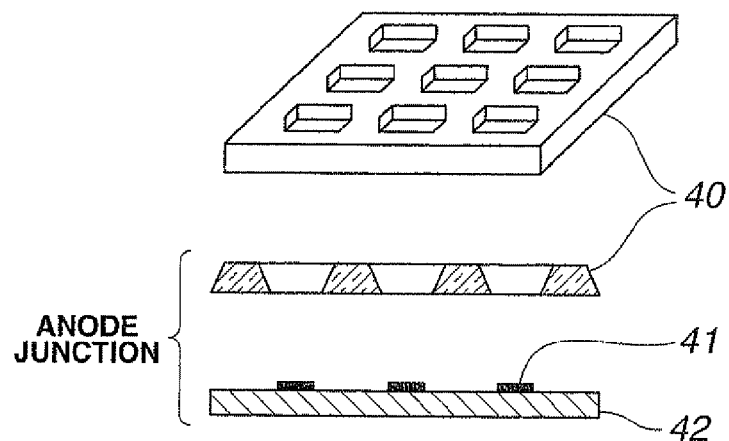
FIG. 5A is a diagram showing a state before bonding in a production process of an capacitive ultrasonic transducer in a third embodiment of the present invention.
Figure 5B:
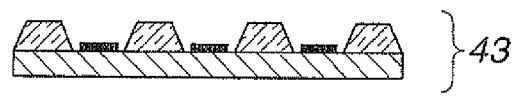
FIG. 5B is a diagram showing a bonding state in the production process of the capacitive ultrasonic transducer in the third embodiment.

FIGS. 5A and 5B are drawings to show fabrication processing for the present embodiment. At first, a silicon substrate 42 subjected to patterning of a plate-like glass substrate 40 provided with a plurality of holes and electrodes 41 thereon is prepared (see FIG. 5A). As to be described below, the glass substrate 40 and the silicon substrate 42 are brought into bonding in the succeeding process and that electrode 41 undergoes patterning on the silicon substrate so that electrode 41 on the silicon substrate 42 is located in the position of the hole of the glass substrate 40.

After the above-described glass substrate 40 and the silicon substrate 42 are prepared, they undergo alignment. Alignment here refers to implementation of positional matching and the glass substrate 40 and the silicon substrate 42 are matched so that the electrode 41 on the silicon substrate 42 is located in the hole portion of the glass substrate 40. At that time, since the glass substrate 40, that is, transparent material is used and the electrode 41 on the silicon substrate 42 can be recognized through the glass substrate 40, positional matching becomes simple for carrying out alignment.

After the above described alignment, direct voltage of several hundreds of volts under several hundreds of ° C. is applied to the glass substrate 40 and the silicon substrate 42 which are brought into bonding (anode bonding). Thereafter, cooling is carried out and, then, a cavity forming substrate (a glass+Si made cavity forming substrate) 43 is formed (see FIG. 5B). Thereafter, a process in FIG. 4B and onwards will be carried out. At that time, in the process in FIG. 4C, using, for the insulating layer 33, a silicon substrate which is exposed at a portion in the resin-made cavity forming substrate 30 side, the insulating layer and the cavity forming substrate 43 made of glass+Si can be brought into bonding here as well with anode bonding.

Here, fabrication of the glass+Si-made cavity forming substrate will not be limited to the above described ones but, after a sacrifice layer is formed at the time of glass plate molding and moreover an insulating layer and an upper electrode are formed on one surface of the glass plate, the sacrifice layer may be removed from the other surface of the glass plate so as to carry out anode bonding with a silicon substrate. In addition, the relationship between glass and Si may be reversed.

As described above, since glass material is used for fabricating the glass+Si-made cavity forming substrate, alignment can be carried out easily due to the property that the other side of glass can be seen through. In addition, since anode bonding is adopted, it is not necessary to use adhesive and the like, and therefore no protrusion of extraneous adhesive to the cavity portion will take place and a highly accurate capacitive ultrasonic transducer can be fabricated.

According to the first to the third embodiments of the present invention described above, a membrane is configured by a plurality of layers and at least one layer among them is formed of high-dielectric film and therefore high acoustic pressure is obtainable in the high-frequency region. In addition, fabrication is feasible with a simple production method, reduction in cost is designed. In addition, ultrasonic vibration of the membrane becomes easily transmissible to a living subject and consequently sensitivity is improved.

Fourth Embodiment

Figure 6:
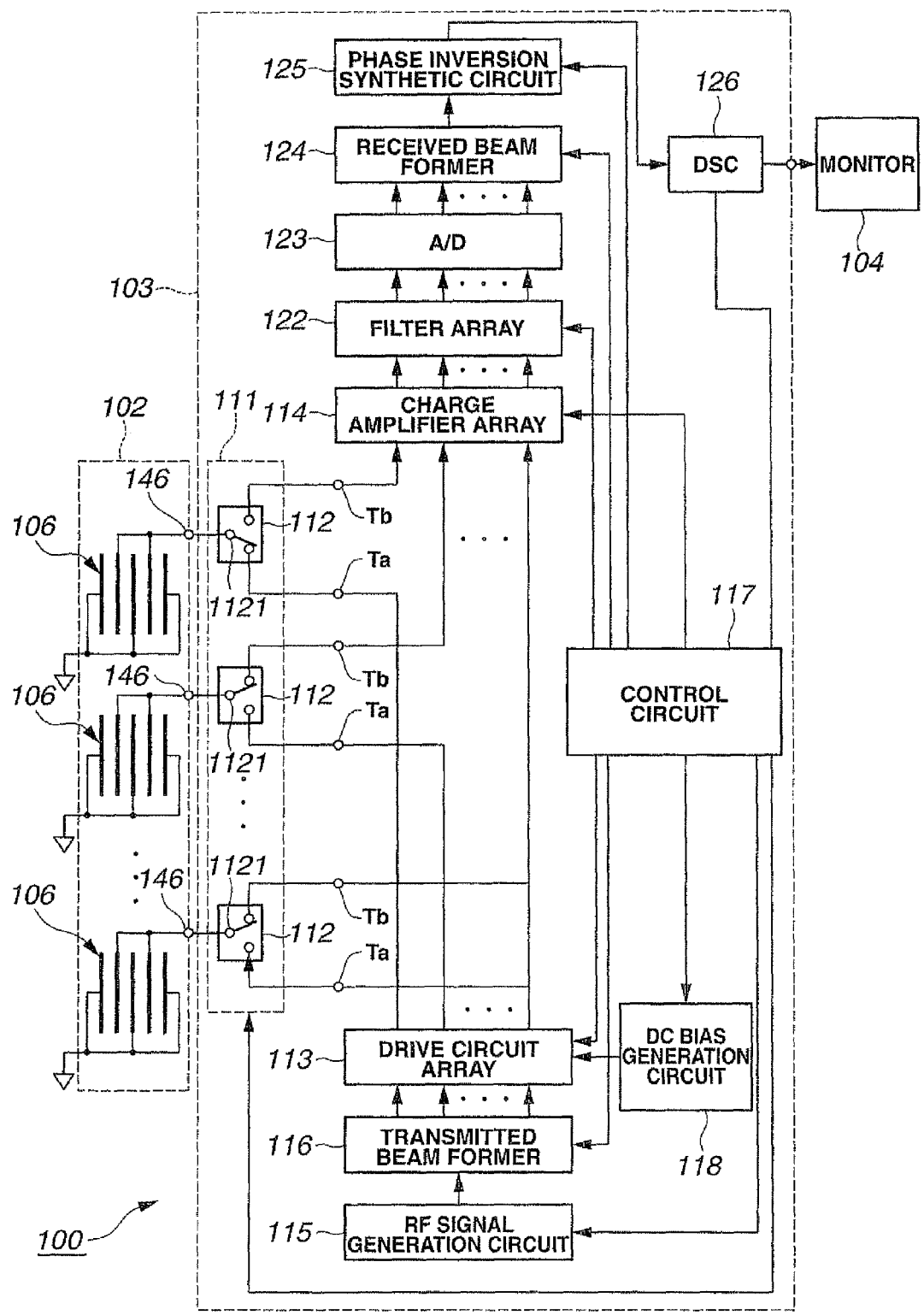
FIG. 6 is a block diagram showing whole structure of an electric system of an ultrasonic diagnostic apparatus comprising a stacked capacitive ultrasonic transducer array of a fourth embodiment of the present invention.
Figure 7A:
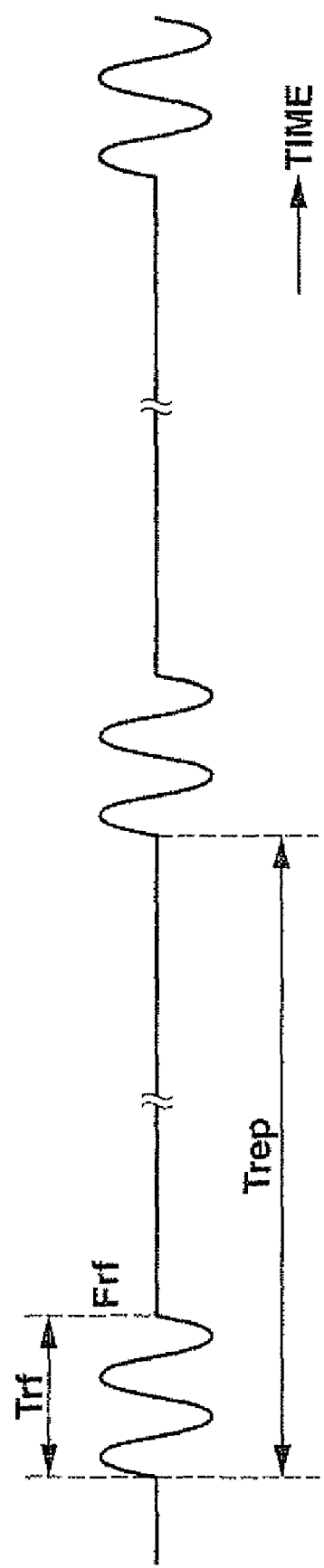
FIG. 7A is a chart showing an RF signal generated by the RF signal generation circuit in FIG. 6.
Figure 8:
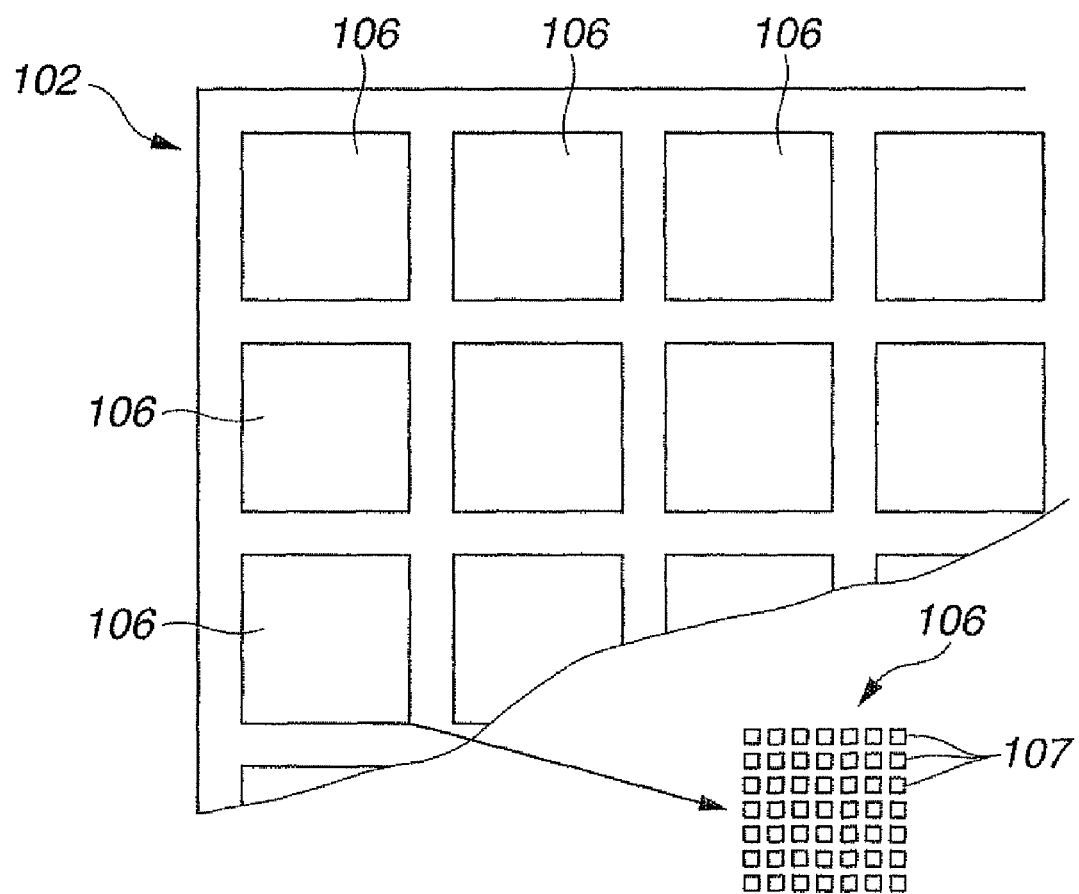
FIG. 8 is a top view showing structure of the stacked capacitive ultrasonic transducer array of the fourth embodiment of the present invention.
Figure 9:
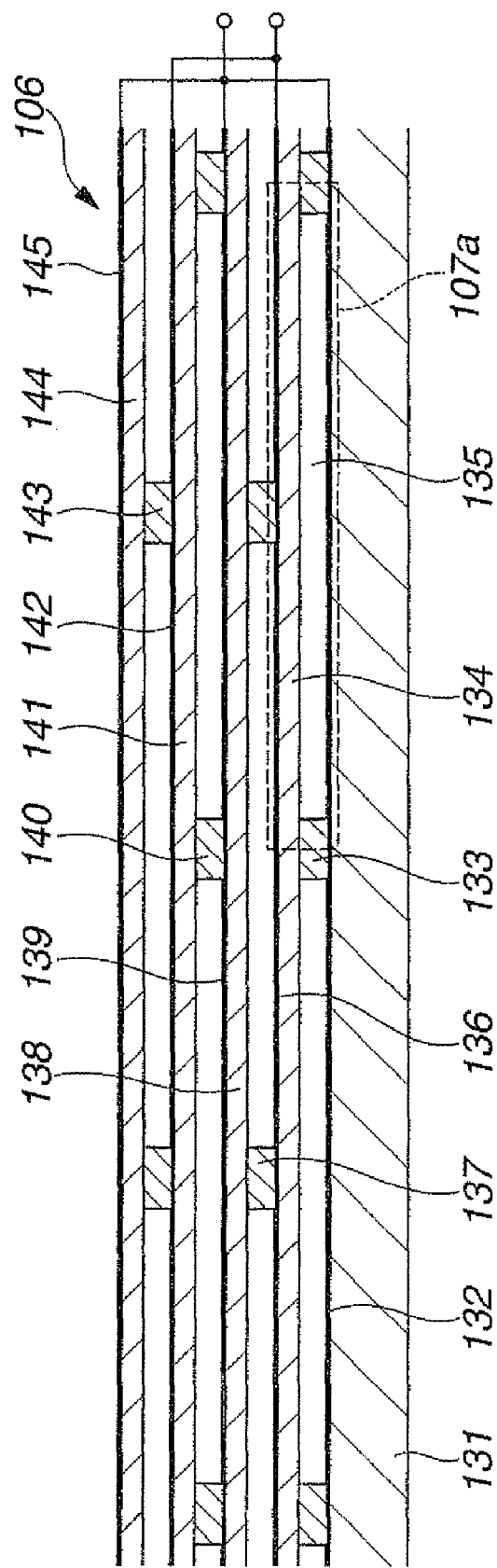
FIG. 9 is a sectional view showing a part of structure of a stacked capacitive ultrasonic transducer element when being not driven.
Figure 10:
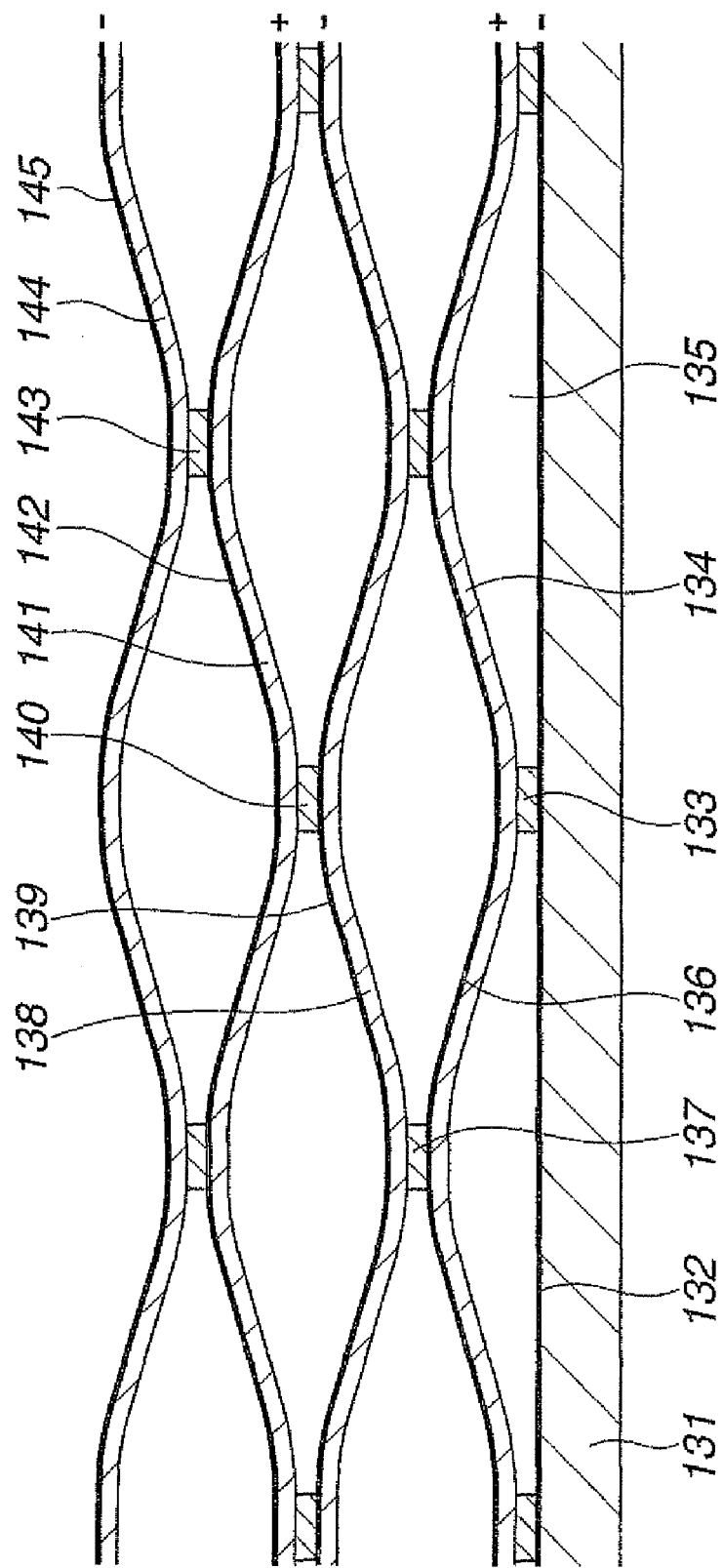
FIG. 10 is a sectional view showing a part of structure of the stacked capacitive ultrasonic transducer element when being driven.

FIGS. 6 to 23H relate to a fourth embodiment of the present invention, FIG. 6 showing a schematic configuration of a holistic electric system of an ultrasonic diagnostic apparatus comprising a stacked type capacitive ultrasonic transducer array of the fourth embodiment of the present invention; FIGS. 7A and 7B showing an RF signal generated by a signal generation circuit and an RF signal generated by a transmitted beam former; FIG. 8 showing a configuration of a stacked type capacitive ultrasonic transducer array of the present embodiment; FIG. 9 showing a part of a sectional structure of a stacked type capacitive ultrasonic transducer element at the time of idling; FIG. 10 showing a part of sectional structure of a stacked type capacitive ultrasonic transducer element at the time of driving; and FIG. 11 showing a configuration example in the case where a stacked type capacitive ultrasonic transducer element is used for transmission and reception.

Figure 11:
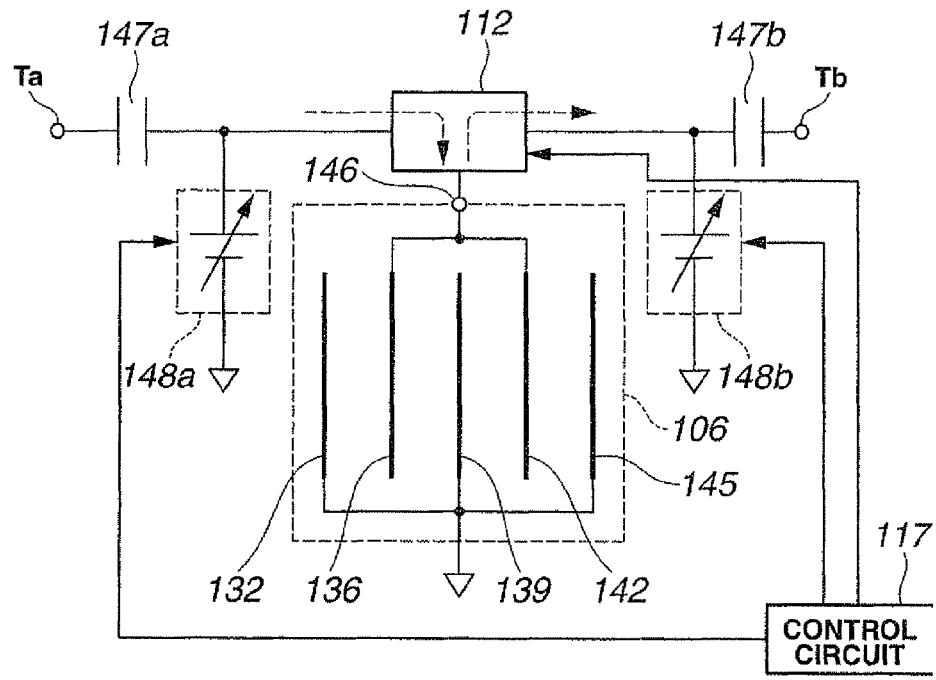
FIG. 11 is a schematic structural diagram at the time of using a stacked capacitive ultrasonic transducer element for both of transmission and reception.
Figure 12:
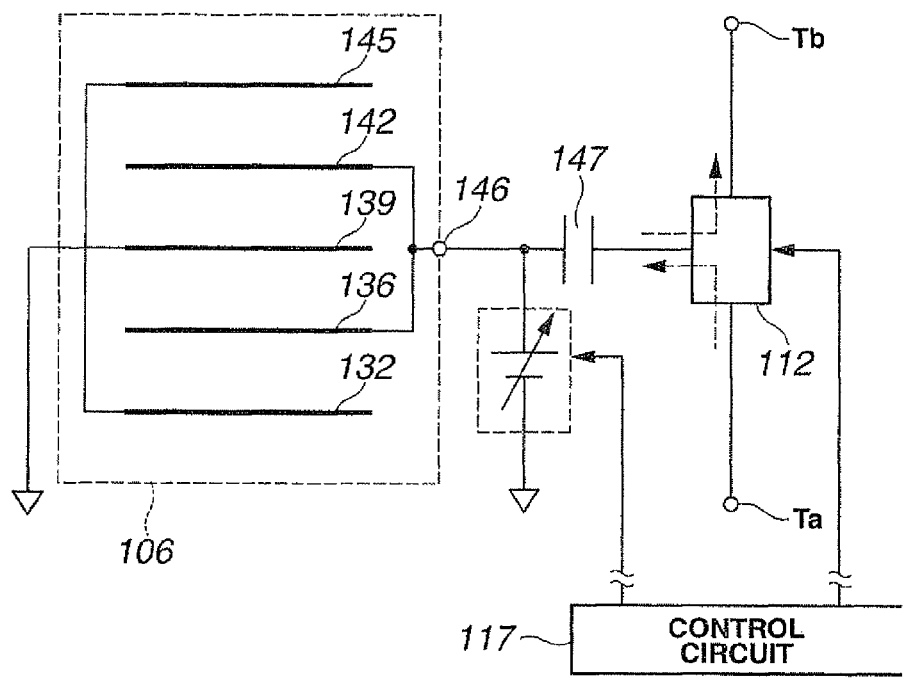
FIG. 12 is a structural diagram showing a modified example of FIG. 11.
Figure 13:
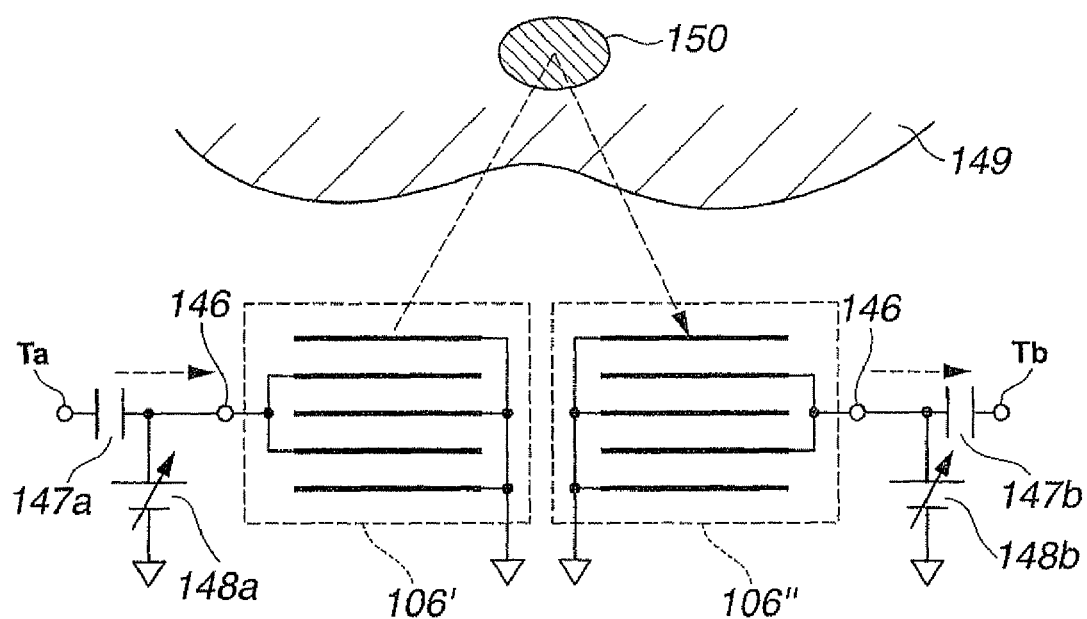
FIG. 13 is a schematic structural diagram at the time of using stacked capacitive ultrasonic transducer elements dedicated for transmission and reception respectively.
Figure 14:
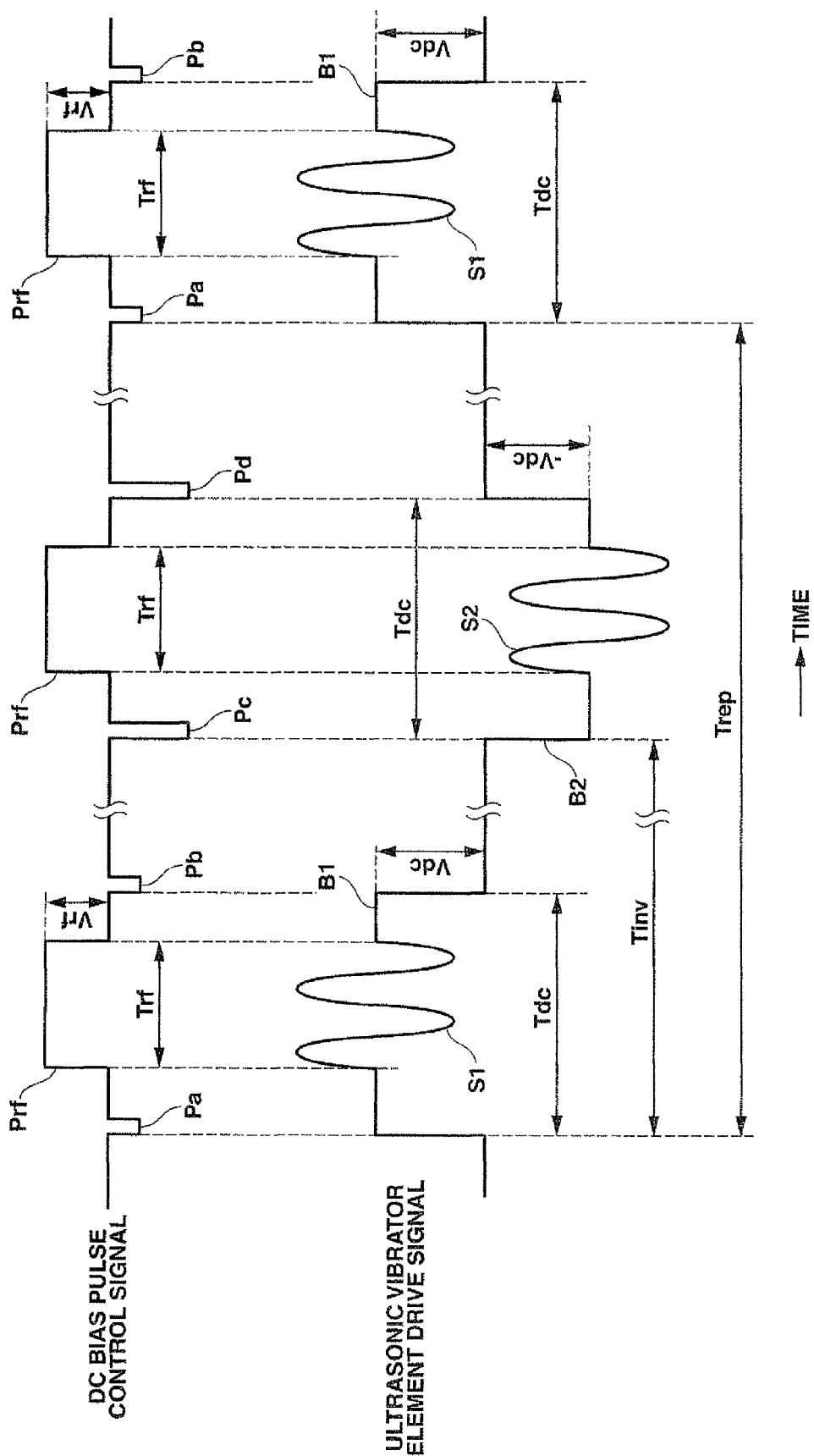
FIG. 14 is a diagram showing a DC bias pulse control signal and an ultrasonic transducer element drive signal for pulse inversion, which are typical waveform examples in the case of performing tissue harmonic imaging in a pulse inversion mode.
Figure 15A:
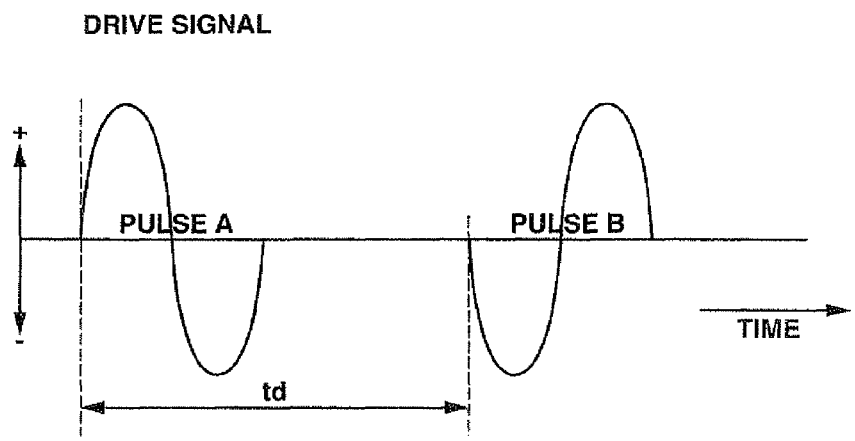
FIG. 15A is a principle diagram of pulse inversion and is a waveform chart showing a drive signal at the time of transmission.
Figure 15B:
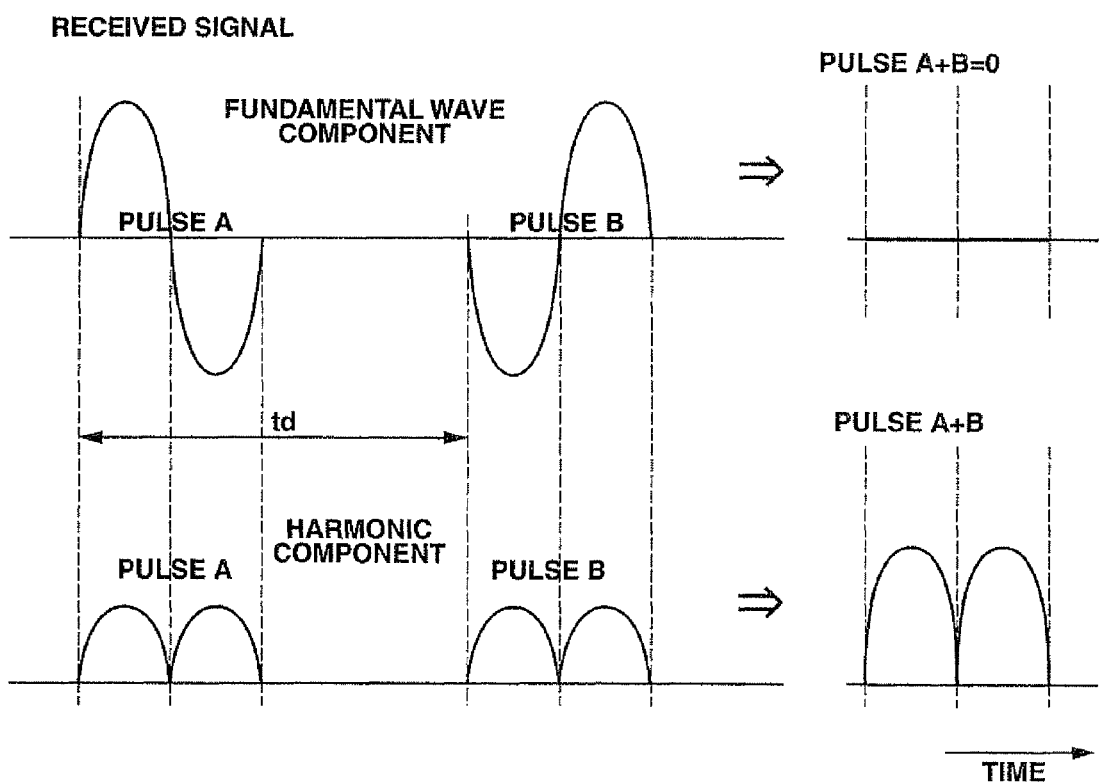
FIG. 15B is a principle diagram of pulse inversion and a waveform chart which illustrates an operation principle of removing a fundamental wave component at the time of reception to obtain a harmonic component.
Figure 16:
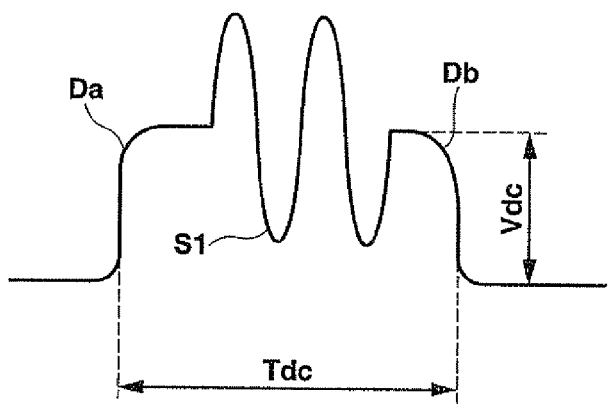
FIG. 16 is a chart showing a waveform example that falling and rising edges of a DC bias voltage are changed.
Figure 17:
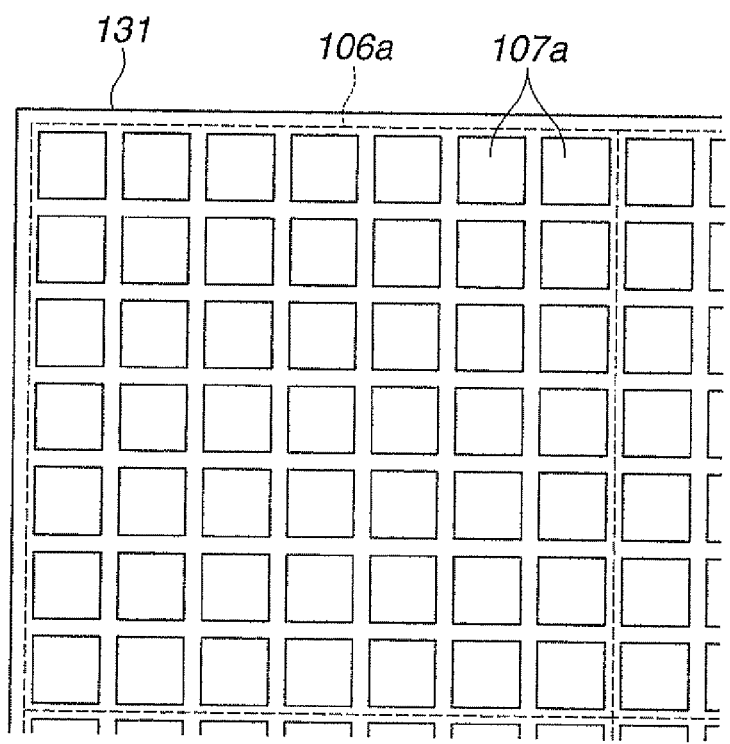
FIG. 17 is a diagram showing an aspect of an array of stacked capacitive ultrasonic transducer cells which is a first layer of a stacked electrostatic capacitive ultrasonic transducer element.

In addition, FIG. 12 shows a variation of FIG. 11; FIG. 13 shows a configuration example in the case where a stacked type capacitive ultrasonic transducer element is used exclusively for transmission and reception. FIG. 14 shows representative signal waveform in the case of carrying out tissue harmonic imaging in a pulse inversion system; FIGS. 15A and 15B show an operation principle diagram of removing fundamental wave component by pulse inversion; FIG. 16 shows a waveform example subjected to change in falling and rising portions of DC bias voltage; and FIG. 17 shows an appearance of arranging stacked type capacitive ultrasonic transducer cells of a first layer of a stacked type capacitive ultrasonic transducer element.

Figure 18:
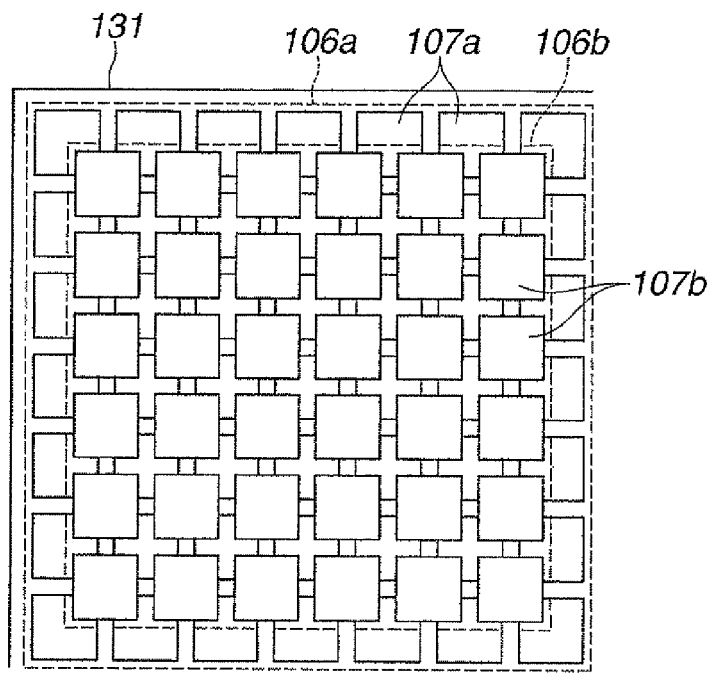
FIG. 18 is a diagram showing an aspect of arrays of stacked capacitive ultrasonic transducer cells which are layers up to a second layer.
Figure 19:
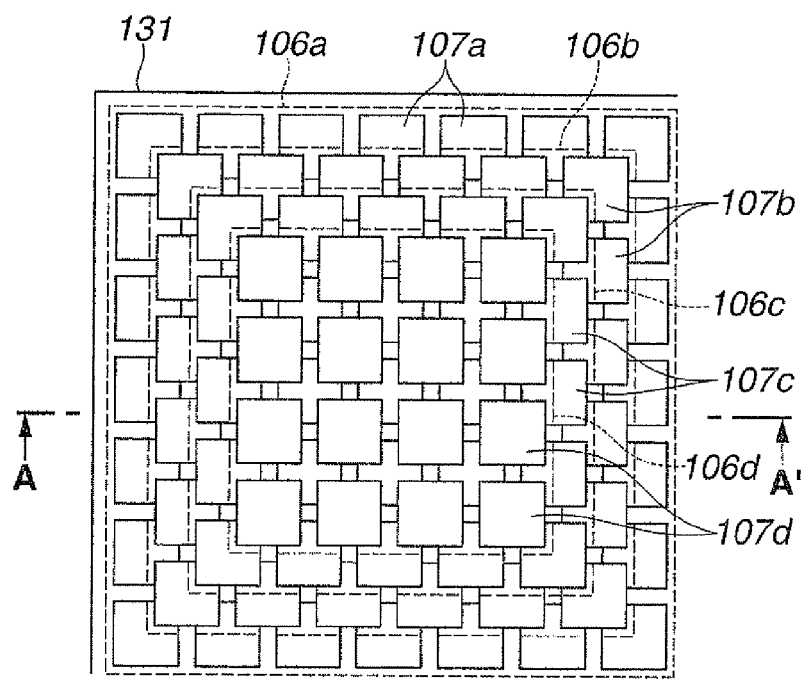
FIG. 19 is a diagram showing an aspect of arrays of stacked capacitive ultrasonic transducer cells which are layers up to a fourth layer.
Figure 20:
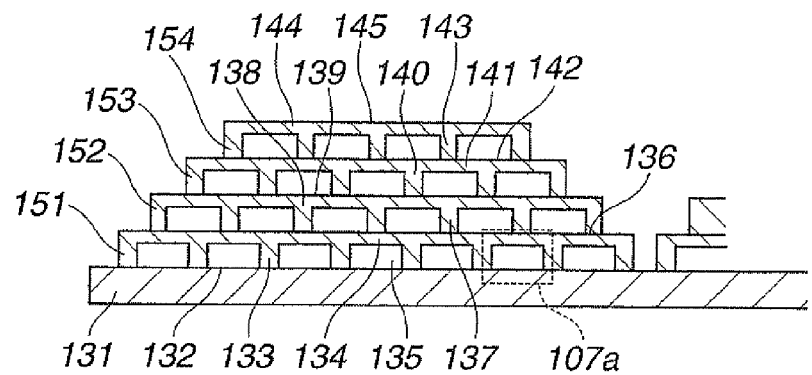
FIG. 20 is a sectional view taken along line A-A' in FIG. 19.
Figure 21:
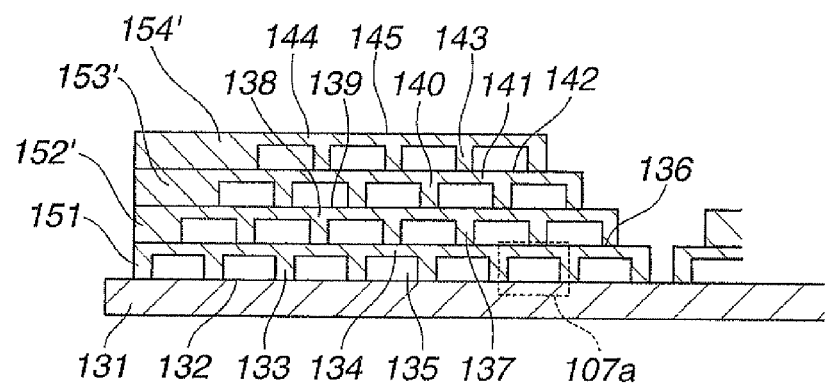
FIG. 21 is a sectional view showing a constituent example of a modified example of FIG. 20.

In addition, FIG. 18 shows appearance of arrangement of stacked type capacitive ultrasonic transducer cells up to a second layer; FIG. 19 shows appearance of arrangement of stacked type capacitive ultrasonic transducer cells up to a fourth layer; FIG. 20 shows a sectional diagram along an A-A' line in FIG. 19; FIG. 21 shows a configuration example of a variation of FIG. 20; FIGS. 22A to 22I show explanatory diagrams of respective processes in the case of fabricating the first layer portion in a stacked type capacitive ultrasonic transducer element; and FIGS. 23R to 23H show explanatory diagrams of respective processes in the case of fabricating up to the second layer portion in a stacked type capacitive ultrasonic transducer element.

As shown in FIG. 6, ultrasonic diagnostic apparatus 100 comprising a fourth embodiment of the present invention is configured by: a stacked type capacitive ultrasonic transducer array (hereinafter simply to be referred to an ultrasonic transducer array) 1022; an ultrasonic observation apparatus 103 driving this ultrasonic transducer array 102 and carrying out a reception process; a monitor 104 to which a video signal outputted from this ultrasonic observation apparatus 3 is inputted and which thereby displays an ultrasonic cross-sectional image of a subject scanned with an ultrasonic beam by the ultrasonic transducer array 2.

The ultrasonic transducer array 102 is configured by a plurality of ultrasonic transducer elements 106 which are arranged two dimensionally. For example, as shown in FIG. 8, an ultrasonic transducer array 102 is configured by an ultrasonic transducer element 106 being regularly arranged in the vertically direction and the horizontal direction. More specifically, the ultrasonic transducer array 102 is configured by N units of ultrasonic transducer elements 106 being, for example, arranged in the vertical direction and M units thereof being arranged in the horizontal direction.

In addition, the ultrasonic transducer element 106 configuring the ultrasonic transducer array 102 of the present embodiment has, as described below, a stacked configuration.

The respective ultrasonic transducer elements 106 are connected to a common terminal 1121 of a transmission reception switching switch 112 configuring a transmission reception switching switch array 111 inside an ultrasonic observation apparatus 103. And, a transmission drive input terminal Ta of this transmission reception switching switch 112 is connected to a drive circuit array 113 and an echo signal output terminal Tb of this transmission reception switching switch 112 is connected to a charge amplifier array 114 having a function as a reception amplifier.

A transmission signal of the RE signal generation circuit 115 is inputted to the drive circuit array 113 through the transmitted beam former 116. The RF signal generation circuit 115 generates a pulsed RF signal with a predetermined frequency Frf in synchronization with, for example, an RF pulse timing signal from the control circuit 117 for transmission. This pulsed RF signal is a low voltage around 10 V and generates, as shown in FIG. 7A, the pulsed RF signal with a predetermined repetition frequency Trep and pulse width Trf.

This low voltage RF signal is inputted to a transmitted beam former 116. This transmitted beam former 116 is configured by, for example, N units of delay circuits so that respective delay amounts are variably settable. And, a delay amount in accordance with a delay time control signal from the control circuit 117 delays an RF signal for transmission, which is outputted to drive the circuit array 113.

FIG. 7B shows output signals by the transmitted beam former 116. For example, the first delay circuit among N units of delay circuits outputs an RF signal with the delay amount remaining at zero while the second delay circuit outputs an RF signal with delay only of a delay amount δ1. Thus, RF signals are outputted with delay amounts being deviated gradually so that the maximum delay amount is set for N units of delay circuits in the vicinity of the center while the delay amount becomes zero for the both ends.

The drive circuit array 113 to which the RE signal from the transmitted beam former 116 is inputted amplifies the REF signal outputted from the transmitted beam former 116 to generate a high voltage RF signal, that is, a drive signal and to output this drive signal, which is superimposed onto DC bias voltage pulse outputted from the DC bias generation circuit 118 to the transmission reception switching switch array 111.

Here, a DC bias waveform control signal is inputted from the control circuit 117 to the DC bias generation circuit 118 and this DC bias generation circuit 118 generates high voltage DC bias voltage pulse in synchronization with a low voltage DC bias waveform control signal and outputs it to drive the circuit array 113.

FIG. 14 is an explanatory diagram in the case of a pulse inversion system and in description with the lower portion of this FIG. 14, DC bias generation circuit 118 generates positive DC bias voltage pulse with voltage value Vdc. That is, what is generated is one after the negative DC bias voltage pulse and negative drive signal of the drive signal in the pulse inversion system for the lower portion in FIG. 14 are deleted.

And in such a state that the drive signal is superimposed onto the DV bias voltage from drive circuit array 113, the drive signal superimposed onto DC bias voltage pulse is applied to the ultrasonic transducer element 106 through the ON-set transmission reception switching switch 112.

As described above, the drive signal in state of a small delay amount is applied to arranged N units of ultrasonic transducer element 106, for example, those on the peripheral side while the drive signal in state of large delay amount is applied to those on the center side.

Thus, a drive signal is applied to arranged N units of ultrasonic transducer element 106 subjected to adjustment in delay time and thereby it is possible to concentrate, in a predetermined direction, and send respective ultrasonic waves transmitted to a subject side with electro-acoustic conversion by N units of the ultrasonic transducer elements 106. In other words, the signal can be transmitted as an ultrasonic beam with intensified ultrasonic energy density.

Here, the transmission reception switching switch array 111 is switched, with a transmission reception switching signal from the control circuit 117 to the reception side from the side of the drive circuit array 113 in which the common terminal 1121 become the transmission side. More specifically, a drive signal with the largest delay amount, for example, is applied to ultrasonic transducer element 106 and thereafter switching from the transmission side to the reception side takes place immediately.

A part of ultrasonic waves reflected by the portion where acoustic impedance on the above described subject side varies is received by the ultrasonic transducer element 106 and is converted into an ultrasonic echo signal, that is, a reception RF signal.

This reception RF signal is inputted to each charge amplifier of the charge amplifying array 114 with high input impedance and is amplified. And a reception RF signal is outputted from each charge amplifier with the output impedance being low impedance. Here, at the time of reception, DC bias voltage is applied to the ultrasonic transducer element 106 from a not shown DC bias generating circuit for reception and the charge amplifier array 114 amplifies the reception RF signal in the state where this DC bias voltage has been applied.

The reception RF signal amplified by the charge amplifier array 114 is inputted to a filter array 122 which is set so as to pass only a predetermined frequency band signal component with the above described frequency Frf as a central frequency. This filter array 122 is designed so that the passband of each filter is made variably settable by a filter property control signal from the control circuit 117.

The reception RF signal having passed the filter array 122 is inputted to an A/D conversion portion 123, is converted from an analogue signal to a digital signal by this A/D conversion portion 123 and thereafter is inputted to received beam former 124. Reception RF signals having N units of phase difference are synthesized into one reception signal by this received beam former 124.

The reception signal synthesized by this received beam former 124 is transmitted to a phase inversion and synthesis circuit 125. Here, in the case where only the normal ultrasonic cross-sectional image is displayed by basic waves to be described below, the signal may be inputted to a digital scan converter (to be abbreviated as DSC) 126 without passing through the phase inversion and synthesis circuit 125.

In the present embodiment, an ultrasonic cross-sectional image by high harmonic is also made displayable by a later described pulse inversion system besides normal display of the normal ultrasonic cross-sectional image by providing the phase inversion and synthesis circuit 125. Control of writing, reading and the like of reception RF signals to the phase inversion and synthesis circuit 125 is carried out by the control circuit 117.

The signal is inputted to the DSC 126 and is converted into a video signal corresponding to the ultrasonic cross-sectional image, and thereafter is outputted to the monitor 104 so that the ultrasonic cross-sectional image is displayed on the display window of the monitor 104.

The ultrasonic transducer array 2 in the present embodiment is configured, as shown in FIG. 8, by regularly arranging ultrasonic transducer elements 106 to become a drive unit in the vertical direction and the horizontal direction.

In addition, each ultrasonic transducer element 106 is configured by a plurality of ultrasonic transducer cells 107 being arranged regularly in the vertical direction and the horizontal direction and are stacked.

In addition, also shown in the schematic diagram in FIG. 6, but each ultrasonic transducer element 106 is configured to be stacked as shown in FIG. 9. Here, FIG. 9 shows such a state where the DC bias voltage and the drive signal for transmission are not applied while FIG. 10 shows such a state where the DC bias voltage and the drive signal for transmission have been applied.

The lower part electrode 132 of a capacitor of the first layer is provided on a silicon substrate 131, a second layer capacitor substrate 134 acting as membrane of the first layer capacitor is stacked on this first layer capacitor lower portion electrode 132 in a state of being supported by a membrane supporting portion 133 of the first layer capacitor at predetermined distance. Here, between adjacent membrane supporting portions 133, a cavity portion 135 making the membrane displaceable is formed. Here, as described below, also on the other layer, the cavity portion 135 is formed.

In addition, the upper surface of this substrate 134 is provided with second layer capacitor lower portion electrode 136 which also operates as an upper portion electrode of the first layer capacitor.

In addition, a third layer capacitor substrate 138 acting as membrane of the second layer capacitor is stacked on this lower part electrode 136 in a state of being supported by the membrane supporting portion 137 of the second layer capacitor at predetermined distance. Also in this layer, the cavity portion 135 is formed between the membrane supporting portions 137.

In addition, the upper surface of this substrate 138 is provided with a third layer capacitor lower portion electrode 139 which also operates as an upper portion electrode of the second layer capacitor.

A fourth layer capacitor substrate 141 acting as a membrane of the third layer capacitor is stacked on this lower part electrode 139 in a state of being supported by the membrane supporting portion 140 of the third layer capacitor at predetermined distance.

In addition, the upper surface of this substrate 141 is provided with a fourth layer capacitor lower portion electrode 142 which also operates as an upper portion electrode of the third layer capacitor.

In addition, a capacitor substrate 144 acting as a membrane of the fourth layer capacitor is stacked on this lower part electrode 142 in a state of being supported by the membrane supporting portion 143 of the third layer capacitor at predetermined distance and the upper surface of this substrate 144 is provided with the fourth layer capacitor upper electrode 145.

Here, thus, each electrode configuring the ultrasonic transducer element 106 in stacked structure is brought into connection so that every other layer of electrodes as shown on the right side of FIG. 9 are brought into conduction.

In addition, an ultrasonic transducer cell is formed in each layer and, for example, the ultrasonic transducer cell in the first layer is indicated by the label 107a, and will be a portion indicated by a dotted line in FIG. 9.

In an ultrasonic transducer element 106 in the present embodiment with such structure, a membrane supporting portion forming each ultrasonic transducer cell 107 has stacked structure to be located approximately in the center portion of the one-layer lower membrane as one of characteristics. In addition, the foot portion of the membrane supporting portion is structured to be brought into bonding only in the vicinity of the center portion of the one-layer lower membrane.

Since such structure is adopted, excitation is made feasible with large amplitude in the case of driving with a drive signal as shown in next FIG. 10.

FIG. 10 shows the state in FIG. 9 in a state that DC bias voltage and the drive signal for transmission are applied.

As apparent from FIG. 10, the membrane supporting portion 137 mounted on the upper surface of the substrate 134 also acting as a membrane supported by the membrane supporting portion 133 in a portion becoming a node of oscillation in the first layer is provided in a portion becoming an abdomen of oscillation in the center position between the adjacent membrane supporting portions 133.

Likewise, the membrane supporting portion 140 mounted on the upper surface of the substrate 138 also acting as a membrane supported by the membrane supporting portion 137 in a portion becoming a node of oscillation in the second layer is provided in a portion becoming an abdomen of oscillation in the center position between the adjacent membrane supporting portions 137.

Since such structure is adopted, it is possible to generate ultrasonic waves with amplitude much larger than in the case of forming an ultrasonic transducer element with a single layer. In addition, it is possible to cause the ultrasonic transducer cell 107 to carry out ultrasonic vibration much more efficiently than in the case of conventional examples of such structure that it is merely stacked.

FIG. 6 shows a schematic configuration of an electric system of the ultrasonic transducer element 106, but when components for switching transmission to reception vise versa with one ultrasonic transducer element 106, FIG. 11 is obtained.

Here, FIG. 11 is configured almost the same as FIG. 6 and FIG. 11 also shows DC cut capacitors 147a and 147b which are omitted in FIG. 6 from description.

As having been described in FIGS. 9 and 10, this ultrasonic element 106 has a lower electrode 132 of the first layer capacitor, for example, on which there disposed are a lower electrode 136 of the second layer capacitor also operating as the upper electrode of the first layer capacitor; a lower electrode 139 of the third layer capacitor also operating as the upper electrode of the second layer capacitor; a lower electrode 142 of the fourth layer capacitor also operating as the upper electrode of the third layer capacitor; and an upper electrode 145 of the fourth layer capacitor, wherein three electrodes of the lower electrode 132 of the first layer capacitor; the lower electrode 139 of the third layer capacitor also operating as the upper electrode of the second layer capacitor; and the upper electrode 145 of the fourth layer capacitor are connected by wire to become a ground terminal which is connected to the ground.

On the other hand, a lower electrode 136 of the second layer capacitor also operating as the upper electrode of the first layer capacitor and a lower electrode 142 of the fourth layer capacitor also operating as the upper electrode of the third layer capacitor are connected by wire to become a signal input/output terminal 146 and be connected to transmission reception switching switch 112.

And at the time of transmission, the transmission reception switching switch 112 is switched by a switch control signal from the control circuit 117 into a state of being connected to the drive terminal Ta side through the DC cut capacitor 147a and, in this case, a drive signal inputted from the driver terminal Ta is applied to the ultrasonic transducer element 106 through the transmission reception switching switch 112 as shown by dotted lines.

In that case, the control circuit 117 is controlled so as to generate predetermined DC bias voltage to a DC bias voltage source 148a. The DC bias voltage source 148a shown in FIG. 11 corresponds to the DC bias generation circuit 118 in FIG. 6.

Accordingly, predetermined DC bias voltage is applied to the ultrasonic transducer element 106 and the drive signal will be applied to the region in the vicinity of the center during the application period of DC bias voltage thereof.

At that occasion, the ultrasonic transducer element 106 is made into stacked structure as shown in FIG. 10, and therefore ultrasonic waves can be transmitted with amplitude much larger than in the case of undergoing no stacking. In addition, it is possible to generate an ultrasonic signal with significant energy since structure with spread with two dimensional arrangement also in the direction of the surface of the silicon substrate 131.

In addition, when transmission (drive) is over, the transmission reception switching switch 112 is switched into a state of being connected to the side of the output terminal Tb by the switching control signal from the control circuit 117, which is, in this case, received by the ultrasonic element 106 so that the echo signal converted into an electric signal is outputted to the side of the charge amplifier array 114 through the DC cut capacitor 147b as indicated by dotted lines via the output terminal Tb of the transmission reception switching switch 112. Also in that case, the control circuit 117 controls the DC bias voltage source 148b to generate predetermined DC bias voltage.

Also at the time of receiving signals, the ultrasonic transducer element 106 in the present embodiment can give rise to amplitude much larger than the ultrasonic transducer of the prior art and can obtain reception signals much larger than the prior art. In other words, it is possible to give rise to much higher sensitivity and obtain reception signals with good S/N.

Here, such a configuration of a variation as shown in FIG. 12 may be adopted. In a configuration shown in FIG. 12, the signal input output terminal 146 is connected to the transmission reception switching switch 112 through the DC cut capacitor 147 and connected to the DC bias voltage source 148. That DC bias voltage source 148 also functions as DC bias voltage sources 148a and 148b in FIG. 11 and is controlled by control circuit 117. Since the other aspects are likewise in FIG. 11, description thereon will be omitted.

In the above described description, one ultrasonic transducer element 106 has been described in the case of being used both for transmission and reception but may be configured, as shown in FIG. 13, to be exclusively used for transmission or reception without switching adjacently disposed two ultrasonic transducer elements 106' and 106".

In that case, at the time of transmission, the drive signal is applied from the drive terminal Ta to the ultrasonic transducer element 106' for transmission through the DC cut capacitor 147a together with the DC bias voltage from the DC bias voltage source 148a.

And ultrasonic waves generated by that ultrasonic transducer element 106' is transmitted to the side of subject 149. When a portion such as a lesioned part 150 and the like different in acoustic impedance is present inside the subject 149, reflection takes place at that portion. A portion of the reflected is received by the ultrasonic transducer element 106" for reception and converted to an electric signal, that is, a reception RF signal. And the signal is outputted to the side of the charge amplifier array 114 through the output terminal Tb via the DC cut capacitor 147b. Also in that case, the control circuit 117 controls the DC bias voltage source 148b to generate a predetermined DC bias voltage. Here, the configuration shown in FIG. 13 also corresponds with a case where an ultrasonic transducer element for transmission and an ultrasonic transducer element for reception are operated as separate units.

In addition, it is possible to carry out tissue harmonic imaging (abbreviated as THI) by pulse inversion with the ultrasonic transducer array 102 of the present embodiment. Also in that case, the ultrasonic transducer array 102 is configured with the ultrasonic transducer element 6 of a stacked type and therefore, an ultrasonic cross-sectional image with good S/N is obtainable.

FIG. 14 shows representative signal waveform in the case of carrying out THI and the upper portion in FIG. 14 shows a DC bias pulse control signal while the lower portion in FIG. 14 shows an ultrasonic transducer element drive signal for pulse inversion. With regard to the drive signal by normal fundamental waves, the drive signal thereof is repeated at the period Trep while the drive signal for pulse inversion is as shown in the lower portion in FIG. 14 is designed to be accompanied by double pulse of driving with phase inversion to period Tinv being a half of period Trep.

In that case, operation principles will be described with FIGS. 15A and 15B. FIGS. 15A and 15B show principle diagrams of pulse inversion.

As shown in FIG. 15A, as a drive signal, pulse B with the opposite phase is applied to the ultrasonic transducer at time difference td (corresponding to period Tinv in FIG. 14) against pulse A so that ultrasonic waves are transmitted to the side of living tissue.

Due to non-linearity of living tissue, there obtained will be a reception signal in which the fundamental wave component of ultrasonic waves and harmonic components having acoustic pressure smaller by several 10 dB, for example, compared with the acoustic pressure of the fundamental wave component, are mixed and therefore it is necessary to remove fundamental wave components from the reception signal mixed with the both components.

In that case, as shown in FIG. 15B, fundamental wave components in the received signal and pulse A, B of odd-order harmonic components retain the same phase relationship as at the time of transmission while even-order harmonic components will become square, biquadratic and so on of fundamental wave and therefore all becomes positive pulse A and B. Higher harmonic in FIG. 15B is depicted with the second higher harmonic.

Accordingly, taking time difference td as 0, addition of pulse A and pulse B of fundamental wave components in a reception signal will derive zero.

In contrast, the harmonic component will be redoubled when the time difference td is set to 0 and addition thereof is taken.

Thus, it is possible to extract only harmonic components. Here, as means for setting the time difference td to 0, phase inversion and synthesis circuit 125 in FIG. 6 in the present embodiment can be adopted. That is, preceding reception pulse is stored in memory inside the phase inversion and synthesis circuit 125 temporarily and the subsequent reception pulse arrives and at that point the preceding reception pulse is read out of the memory and the addition of the both are taken and thereby the fundamental wave component and odd-order harmonic components can be set to 0 and even-order harmonic components can be obtained by redoubling.

FIGS. 15A and 15B are principle diagrams and are for a method not depending on an electrostatic type. In contrast, the method shown in FIG. 14 is a capacitance type, and therefore a drive signal with the same phase is superimposed onto DC bias voltage pulse different in polarity and is applied to the capacitive ultrasonic transducer element 106 and thereby ultrasonic waves in opposite phase are generated and they are transmitted to the side of a live body. Therefore, in the case of THI, the DC bias generation circuit 118 generates positive and negative DC bias voltage pulse as will be described below and the drive circuit array 113 generates a double drive signal with a built-in delay circuit not shown in the drawing.

At the time of reception, the reception signal is designed to be obtained in a state where DC bias voltage with one polarity is applied, giving rise to, thereby, operations likewise in the case of FIGS. 15A and 15B.

Next, with reference to FIG. 14, a method of generating a drive signal for pulse inversion will be described.

The control circuit 117 outputs a DC bias pulse control signal to the drive circuit array 113 and the DC bias generation circuit 118 as shown in the upper portion in FIG. 14.

The DC bias generation circuit 118 is controlled by +DC bias startup timing pulse Pa in this DC bias pulse control signal. And the DC bias generation circuit 118 generates high voltage positive DC bias voltage pulse B1 with a voltage value indicated by Vdc as shown in the lower portion in FIG. 14 in synchronization with this +DC bias start-up timing pulse Pa and stops generation of DC bias voltage pulse B1 with +DC bias stop timing pulse Pb. The generation period of this DC bias voltage pulse B1 will become Tdc.

In addition, the above described DC bias pulse control signal is accompanied by RF signal generation timing pulse Prf with a signal voltage value being Vrf immediately after +DC bias startup timing pulse Pa during the generation period Tdc of DC bias voltage pulse B1. This RF signal generation timing pulse Prf is inputted to each drive circuit in the drive circuit array 113, each drive circuit amplifies the inputted RF signal during the period of this RF signal generation timing pulse Prf to generate the high voltage RF signal S1.

Accordingly, the drive signal shown in the lower portion in FIG. 14 will be obtained by superimposing the amplified high voltage RF signal S1 onto DC bias voltage pulse B1 during the period Trf of the above described RF signal generation timing pulse Prf.

Here, the generation period Trf of that RF signal generation timing pulse Prf is shorter than the generation period Tdc of bias voltage.

And thus the high voltage RE signal S1 is superimposed onto positive DC bias voltage pulse B1 to obtain a drive signal which is applied to the ultrasonic transducer element 106. And the ultrasonic transducer element 106 converts it into ultrasonic waves and those ultrasonic waves are transmitted to the side of the living tissue.

After a predetermined time Tinv from that transmission time, the DC bias pulse control signal from the control circuit 117 has −DC bias startup timing pulse Pc as shown in the upper portion in FIG. 14 and this −DC bias startup timing pulse Pc is inputted to the DC bias generation circuit 118.

And next, as shown in the lower portion in FIG. 14, in synchronization with that −DC bias startup timing pulse Pc, the DC bias generation circuit 118 generates negative DC bias voltage pulse B2 with the voltage value being Vdc, and generation of DC bias voltage pulse B2 is stopped by subsequent −DC bias stop timing pulse Pd. The generation period of that DC bias voltage pulse B2 will become Tdc.

In addition, the DC bias pulse control signal will be accompanied by RF signal generation timing pulse Prf with a signal voltage value being Vrf immediately after the above described −DC bias startup timing pulse Pc and that period Trf is shorter than the generation period Tdo of DC bias voltage pulse B2.

During the period Trf of the above described REF signal generation timing pulse Prf, each drive circuit of the drive circuit array 113 amplifies the Rf signal through a delay circuit with delay time not shown in the drawing being Tinv to generate a high voltage RF signal S2 and this RE signal S2 is superimposed onto DC bias voltage pulse B2 and is outputted.

And thus the high voltage RF signal S2 is superimposed onto negative DC bias voltage pulse B2 to obtain a drive signal which is applied to the ultrasonic transducer element 106. And the ultrasonic transducer element 106 converts it into ultrasonic waves and those ultrasonic waves are transmitted to the side of living tissue.

In that case, since the REF signal S2 is superimposed onto negative DC bias voltage pulse B2 to generate the drive signal, an ultrasonic wave in the opposite phase from the one brought into ultrasonic vibration with a drive signal obtained by superimposing the RF signal S1 onto positive DC bias voltage pulse B1 will be transmitted.

Here, a transducer drive signal in the lower portion in FIG. 14 is applied to N units of ultrasonic transducer elements 6 arranged, for example, in the vertical direction with phase difference.

And, an ultrasonic beam focused in a predetermined direction with intensified ultrasonic energy density will be created and transmitted to the side of a living tissue. The ultrasonic waves reflected on the side of a living subject are converted into an electric signal, that is, an echo signal (or a reception RE signal) with each ultrasonic transducer element 106 again. And, the signal is amplified and undergoes impedance conversion with the charge amplifier array 114, and thereafter inputted to the filter array 122.

Harmonic components of the filter array 122 are lowered together with ultrasonic wave transmission and attenuation by a living subject and frequency components shift to the low frequency side in general. In consideration of this shift, the center frequency of the filter is controlled so that the noise outside the band is blocked. The control signal varying transmission distance of ultrasonic waves together with the center frequency of a filter is transmitted from the control circuit 117 to the filter array 122.

The reception RF signal having passed that filter array 122 is converted into a digital signal with the A/D converter 123 and thereafter synthesized into one reception signal with the received beam former 124. That reception signal is configured by a signal component portion inputted precedingly chronologically and a signal component inputted subsequently, and the preceding signal component is separated and is temporarily stored in the memory inside phase inversion and synthesis circuit 125.

And, the precedingly inputted signal component is read out from the memory after predetermined time Tinv and is added to the subsequently inputted signal component.

That is, each ultrasonic transducer element 106 is driven in the opposite phase after respective predetermined time Tinv and the fundamental wave component in the reception RF signal retains its phase, Also in the case of synthesis with the received beam former 124, each of them retains its phase relation.

In that case, the signal of the memory inside the phase inversion and synthesis circuit 125 is read in timing subjected to deviation by this predetermined time Tinv, the both signals are added together and thereby the fundamental wave components in the opposite phase cancel each other. In contrast, even-ordered harmonic components are the fundamental wave squared, quadruplicated and so on, and therefore without being influenced by the opposite phase, a doubled signal will be extracted as a result of addition.

Thereafter, the synthesized signal is outputted to the DSC 126 and converted into a video signal so that an ultrasonic cross-sectional image obtained by high harmonic is displayed on the display window of the monitor 104.

That is, imaging with high harmonic and imaging with fundamental waves may be carried out alternately to synthesize the both signals and display the ultrasonic cross-sectional image. In that case, in the case of carrying out imaging of the fundamental wave filter array 122 is set to such a frequency band to pass fundamental waves.

Here, in the lower portion in FIG. 14, rise and fall of the DC bias voltage are shaped as steep waveform, but it is preferable to take smoothly rising DC bias pulse rising portion Da as shown in FIG. 16 and a smoothly falling DC bias pulse falling portion Db. Next, structure of the ultrasonic transducer element 6 in the present embodiment will be described further and a fabrication method thereof will be described as well.

FIG. 17 shows an ultrasonic transducer element 6a for the first layer. A plurality of ultrasonic transducer cells 107a configuring an ultrasonic transducer element 106a for the first layer are two-dimensionally arranged regularly on silicon substrate 131. In this example, the ultrasonic transducer element 106a for the first layer is configured by 7×7 units of ultrasonic transducer cells 107a.

And, as shown in FIG. 18, ultrasonic transducer cells 107b configuring an ultrasonic transducer element 106b for the second layer are stacked on the ultrasonic transducer cells 107a configuring this ultrasonic transducer element 106a for the first layer.

Moreover, ultrasonic transducer cells 107c configuring an ultrasonic transducer element 106c for the third layer are stacked on the ultrasonic transducer cells 107b of this ultrasonic transducer element 106b for the second layer.

Moreover, as shown in FIG. 19, ultrasonic transducer cells 107d configuring an ultrasonic transducer element 106d for the fourth layer are stacked on the ultrasonic transducer cell 107c configuring the ultrasonic transducer element 106c for the third layer.

In addition, FIG. 20 shows a sectional diagram along an A-A' line in FIG. 19. As shown in FIG. 9 and the like, ultrasonic transducer element 106 has been stacked.

As shown in FIG. 20, membrane supporting portions 151, 152, 153 and 154 in the periphery portion in each layer are formed so as to block its inside cavity 135 from the outside. In FIG. 20, the bonding portion with its lower layer is formed in a shape of a line in the direction perpendicular to the paper sheet.

Thus, the periphery is structured to be blocked from the outside and is provided with air-tight structure so as to prevent unnecessary steam, liquid and the like being mixed into the cavity 135 not only in use but also in the case of cleaning and the like after use.

Here, as in a variation shown in FIG. 21, in order to uniform the size of the circumference, for example, in order to match the size to the periphery of a membrane supporting portion 151, a membrane supporting portion 152', 153', 154' made larger in thickness may be adopted. Here, as shown in FIGS. 20 and 21, support appropriate for stacked structure may be carried out, making membrane supporting portion thickness thicker and thicker as the position goes down. In addition, with regard to the membrane as well, making a membrane thicker and thicker as the position goes down, structure corresponding with stacked structure may be adopted.

Next, with reference to FIGS. 22A to 22I, a method of fabricating an ultrasonic transducer element 106a in the present embodiment will be described.

Figure 22A:
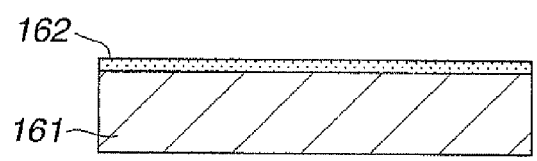
FIG. 22A is an explanatory diagram of an insulating layer forming step in the case of producing a first layer portion in a stacked electrostatic capacitive ultrasonic transducer element.
Figure 22B:
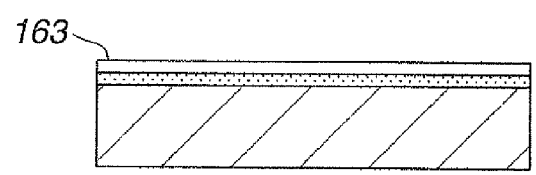
FIG. 22B is an explanatory diagram of a lower electrode forming step in the case of producing the first layer portion in the stacked electrostatic capacitive ultrasonic transducer element.

As shown in FIG. 22A, an insulating layer 162 such as silicon oxide and the like is formed on an upper face of a silicon substrate 161. Next, as shown in FIG. 22B, a lower electrode 163 is formed on this insulating layer 162.

Figure 22C:
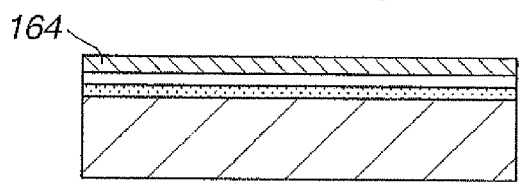
FIG. 22C is an explanatory diagram of a sacrifice layer forming step in the case of producing the first layer portion in the stacked electrostatic capacitive ultrasonic transducer element.

Next, as shown in FIG. 22C, a sacrifice layer 164 necessary for forming a cavity and the like is formed. This sacrifice layer 164 is a temporal layer to be removed later and is formed by, for example, polysilicon which can be easily removed by etching and the like.

Figure 22D:
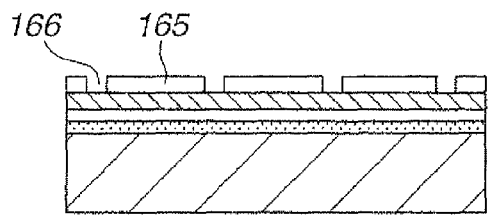
FIG. 22D is an explanatory diagram of a mask forming step in the case of producing the first layer portion in the stacked electrostatic capacitive ultrasonic transducer element.

Next, as shown in FIG. 22D, masks 165 are formed so as to be arranged two dimensionally on the portion where cavities in the sacrifice layer 164 are formed. FIG. 22 shows sectional views in the left-right direction, for example, but masks 165 are formed in the likewise arrangement in the direction perpendicular to the sheet surface as well.

And, no mask 165 will be formed in (portion to become a membrane supporting portion of) circumference 166 of each cavity.

Figure 22E:
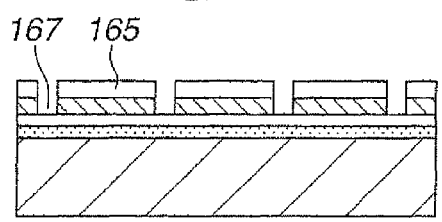
FIG. 22E is an explanatory diagram of a concavity forming step for membrane support section formation in the case of producing the first layer portion in the stacked electrostatic capacitive ultrasonic transducer element.

Next, as shown in FIG. 22E, the sacrifice layer 164 of portions with no mask 165 is removed by etching process to form concave portions 167 for forming a membrane supporting portion.

Figure 22F:
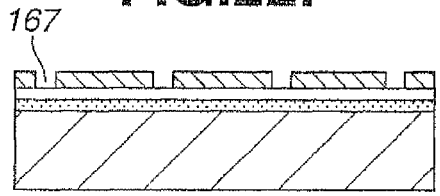
FIG. 22F is an explanatory diagram of a mask removal step in the case of producing the first layer portion in the stacked electrostatic capacitive ultrasonic transducer element.
Figure 22G:
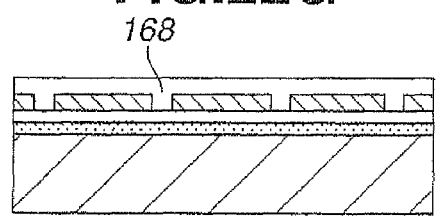
FIG. 22G is an explanatory diagram of a forming step of a film, which becomes a membrane film, in the case of producing the first layer portion in the stacked electrostatic capacitive ultrasonic transducer element.

Next, as shown in FIG. 22F, masks 165 are removed. And, as shown in next FIG. 22G, concave portions 167 are filled in their inside to form a membrane supporting portion and film 168 to become membrane film is formed with insulating silicon nitride and the like so as to cover the upper surface of the sacrifice layer 164.

Figure 22H:
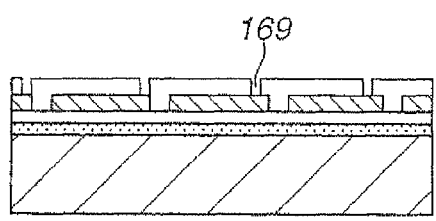
FIG. 22H is an explanatory diagram of a forming step of contact holes from the above-mentioned film to the sacrifice layer in the case of producing the first layer portion in the stacked electrostatic capacitive ultrasonic transducer element.
Figure 22I:
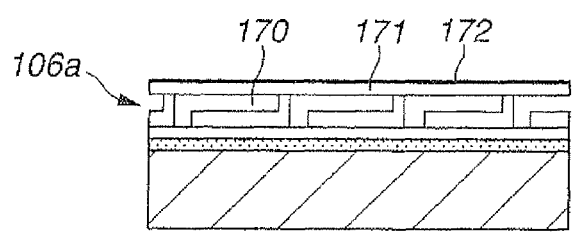
FIG. 22I is an explanatory diagram of a forming step of a membrane layer and an upper electrode in the case of producing the first layer portion in the stacked electrostatic capacitive ultrasonic transducer element.

Next, as shown in FIG. 22H, holes 169 reaching from this film 168 down to the sacrifice layer 164 are formed. And the sacrifice layer 164 is removed by etching and the like. And, the sacrifice layer 164 is removed to form a hollow portion 170 and the membrane layer 171 is formed so as to seal the holes 169 from thereabove. Silicon nitride can be used for this membrane layer 171. An upper electrode 172 is formed on this membrane layer 171, giving rise to FIG. 22I.

Implementing the process shown in FIGS. 22A to 22I, the ultrasonic transducer element 106a for the first layer can be formed. And by repeating the process shown in FIGS. 22C to 22I onto this ultrasonic transducer element 106b for the first layer, an ultrasonic transducer element 106b for the second layer can be formed.

FIGS. 23A to 23H show explanatory diagrams on the process forming the ultrasonic transducer element 106b for the second layer.

Figure 23A:
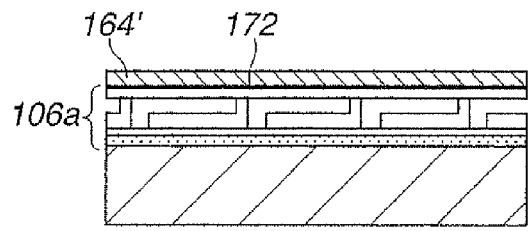
FIG. 23A is an explanatory diagram of a step of forming a sacrifice layer on the above-mentioned upper electrode in the case of producing layers and the like up to a second layer portion in the stacked electrostatic capacitive ultrasonic transducer element.
Figure 23B:
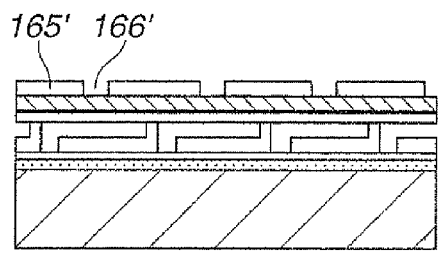
FIG. 23B is an explanatory diagram of a step of forming a mask on the above-mentioned sacrifice layer in the case of producing layers and the like up to the second layer portion in the stacked electrostatic capacitive ultrasonic transducer element.

In brief explanation, FIG. 23A shows a drawing where a sacrifice layer 164' has been formed on an upper electrode 172 and FIG. 23B shows a drawing where the sacrifice layer 164' has been provided with masks 165'. Here, no mask 165' will be formed in (portion to become a membrane supporting portion of) a circumference 1661 of each cavity. In addition, masks 165' on this second layer are formed with displacement by half a pitch two dimensionally apart from the location where masks 165 of the first layer (to become an immediately underneath layer) have been formed.

That is, the center position of a mask 1651 in the second layer is formed to come to a location between two masks 165 in the first layer subjected to two-dimensional displacement. Accordingly, the position of the masks on the third layer will be displaced by half a pitch apart from the second layer and will be formed in the location above the location of the first mask.

Figure 23C:
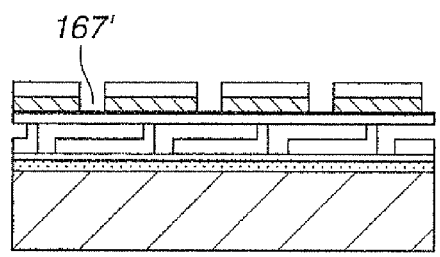
FIG. 23C is an explanatory diagram of a concavity forming step in the case of producing layers up to the second layer portion in the stacked electrostatic capacitive ultrasonic transducer element.
Figure 23D:
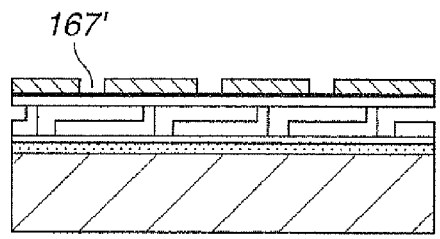
FIG. 23D is an explanatory diagram of a mask removal step in the case of producing layers and the like up to the second layer portion in the stacked electrostatic capacitive ultrasonic transducer element.

FIG. 23C shows a drawing where concave portions 167' are provided subject an etching process and FIG. 23D shows a drawing subjected to removal of the masks 165'.

Figure 23E:
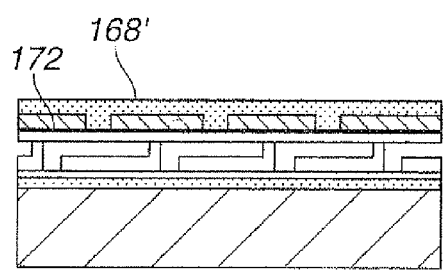
FIG. 23E is an explanatory diagram of a forming step of a film, which becomes a membrane film, in the case of producing layers and the like up to the second layer portion in the stacked electrostatic capacitive ultrasonic transducer element.
Figure 23F:
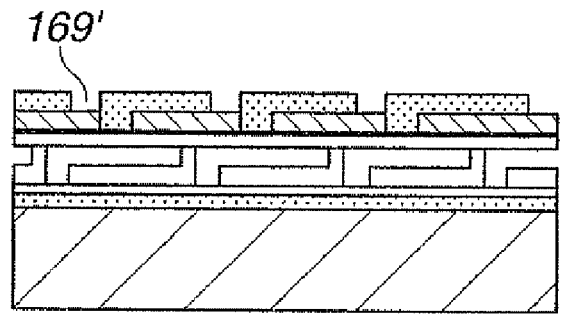
FIG. 23F is an explanatory diagram of a forming step of contact holes from the above-mentioned film to the sacrifice layer in the case of producing layers and the like up to the second layer portion in the stacked electrostatic capacitive ultrasonic transducer element.
Figure 23G:
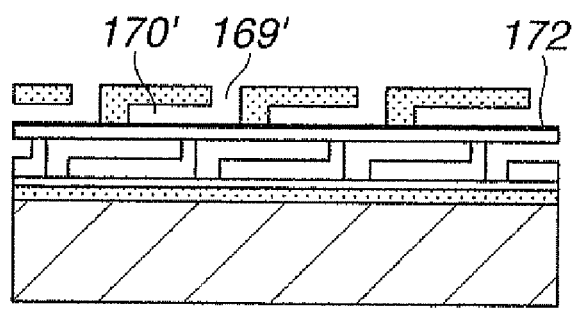
FIG. 23G is an explanatory diagram of a sacrifice layer removal step in the case of producing layers and the like up to the second layer portion in the stacked electrostatic capacitive ultrasonic transducer element.
Figure 23H:
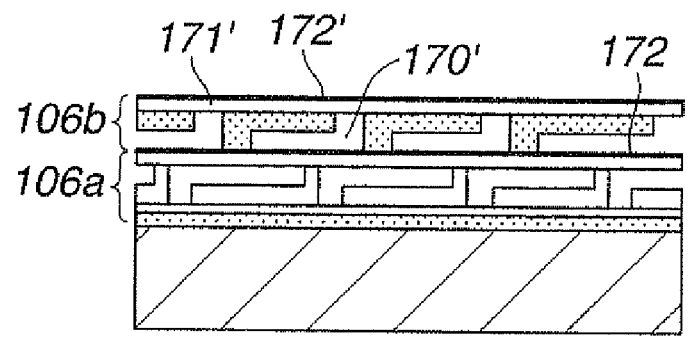
FIG. 23H is an explanatory diagram of a forming step of a membrane layer and an upper electrode in the case of producing layers and the like up to the second layer portion in the stacked electrostatic capacitive ultrasonic transducer element.

In addition, FIG. 23E shows a drawing where film 168' to become a membrane layer is formed; FIG. 23F shows a drawing where holes 169' reaching the sacrifice layer 164' have been provided; and FIG. 23G shows a drawing where the sacrifice layer 164' has been removed by etching.

FIG. 23H shows a drawing where a membrane layer 171' is formed and thereon an upper electrode 1721 has been formed further. With the process shown in FIGS. 23A to 23H, the ultrasonic transducer element up to the second layer can be fabricated. Moreover thereafter, repeating the likewise fabrication process, an ultrasonic transducer element for the third layer can be fabricated, and thereon an ultrasonic transducer element for the fourth layer is formed and thereby, the ultrasonic transducer element 6 with four layer structure can be fabricated.

According to thus fabricated stacked type capacitive ultrasonic transducer element 106, as described above, an ultrasonic beam with large acoustic pressure compared with the prior arts can be generated and can be converted to an electric signal with large amplitude also in the case of reception and an ultrasonic cross-sectional image with good S/N is obtainable.

In addition, beam focusing is carried out with such stacked type capacitive ultrasonic transducer elements 106 being arranged two dimensionally like an array, an ultrasonic beam with further larger acoustic pressure can be generated and can be converted to an electric signal with large amplitude also in the case of reception and an ultrasonic cross-sectional image with good S/N is obtainable.

According to the fourth embodiment of the present invention described above, ultrasonic waves are transmitted to/received from a living subject with a stacked type capacitive ultrasonic transducer, an ultrasonic transducer beam with high energy density can be transmitted/received and an ultrasonic cross-sectional image with good S/N is obtainable.

Fifth Embodiment

Figure 24:
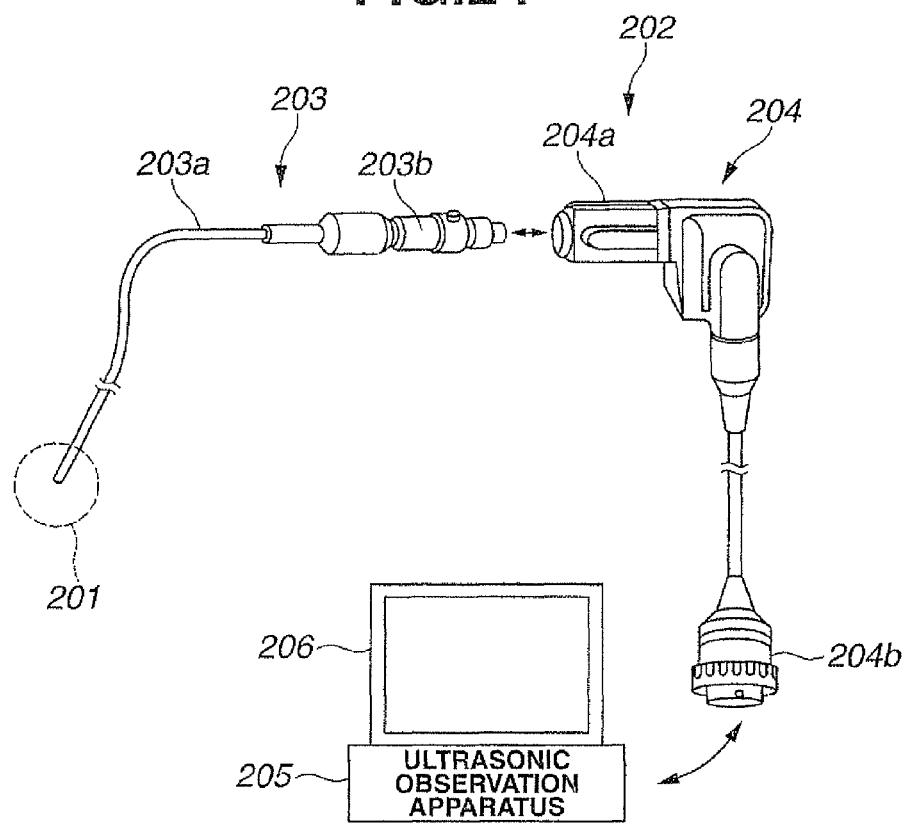
FIG. 24 is a diagram showing a capacitive ultrasonic probe in a capacitive ultrasonic probe apparatus of a fifth embodiment of the present invention.
Figure 25:
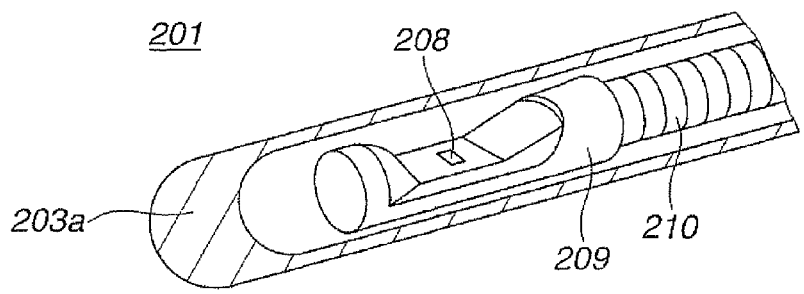
FIG. 25 is a diagram showing enlargingly an end portion of the capacitive ultrasonic probe in FIG. 24.

FIG. 24 is a drawing showing an capacitive ultrasonic probe in an capacitive ultrasonic probe apparatus of a fifth embodiment of the present invention and FIG. 25 is a perspective view showing a capacitive ultrasonic probe tip portion in FIG. 24 in an enlarged fashion.

In FIG. 24, reference numeral 201 denotes a probe head; reference numeral 202 denotes a capacitive ultrasonic probe apparatus; reference numeral 203 denotes an capacitive ultrasonic probe; reference numeral 203a denotes a sheath; reference numeral 203b denotes a joint; reference numeral 204 denotes a drive control portion; reference numeral and character 204a and 204b denote connectors; reference numeral 205 denotes an ultrasonic observation apparatus; reference numeral 206 denotes a motor; reference numeral 208 denotes an capacitive ultrasonic transducer; reference numeral 209 denotes a housing of an ultrasonic transducer; and reference numeral 210 denotes a flexible shaft.

The probe head 201 comprises the ultrasonic transducer 208 as an ultrasonic sensor, and is used by inserting the sheath 203a configured by a thin tube into an ultrasonic forcep hole, looking at an optical image with an endoscope at the point where the tip protrudes to observe an ultrasonic image and the like. A capacitive ultrasonic transducer is used as the ultrasonic transducer 208 of the probe head 201 replacing ultrasonic transducer of a conventional piezo-electric type.

FIG. 25 shows structure of the above described probe head 201.

In FIG. 25, the capacitive ultrasonic transducer 208 is disposed inside the sheath 203a in the probe head 201 in state of being retained by the housing 209. The housing 209 is provided with an opening, the opening is formed opposite to the ultrasonic dispatch surface of the ultrasonic transducer 208.

Figure 26:
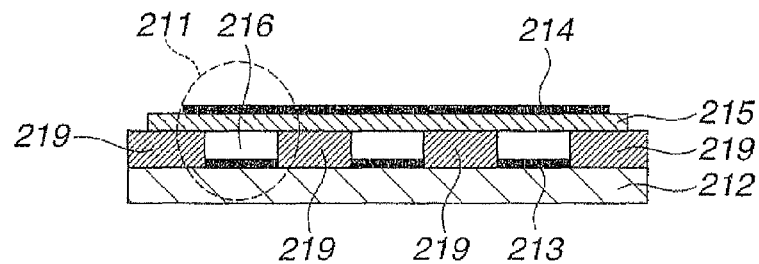
FIG. 26 is a sectional view of a part of the capacitive ultrasonic transducer in FIG. 25.

FIG. 26 shows a sectional view of a portion of the capacitive ultrasonic transducer 208 in FIG. 25.

FIG. 26 shows basic structure, wherein reference numeral 211 denotes a capacitive ultrasonic transducer cell; reference numeral 212 denotes a silicon substrate; reference numeral 213 denotes a lower electrode; reference numeral 214 denotes an upper electrode; reference numeral 215 denotes a membrane; reference numeral 216 denotes a cavity; and reference numeral 219 denotes a membrane supporting portion.

The silicon substrate 212 is configured by low resistant silicon and configured, for example, by insulator selected from the group consisting of SiN, $SiO_2$ and the like.

On the silicon substrate 212, in order that each unit forms a transducer cell, the lower electrode 213 is formed on the low resistant silicon substrate 212; the insulating membrane supporting portion 219 is formed; the membrane 215 is formed of polymer film; and the upper electrode 214 is formed. As described above, the cavity 216 is formed. Cavity 216 is space filled with air and the like. For such structure preparation, it is also possible to make preparation once for all with semiconductor processing.

Figure 27:
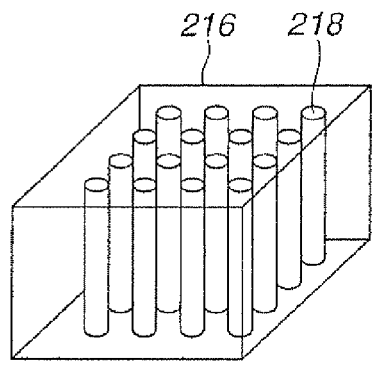
FIG. 27 is a perspective view showing characteristic structure of the fifth embodiment of the present invention three-dimensionally.
Figure 28:
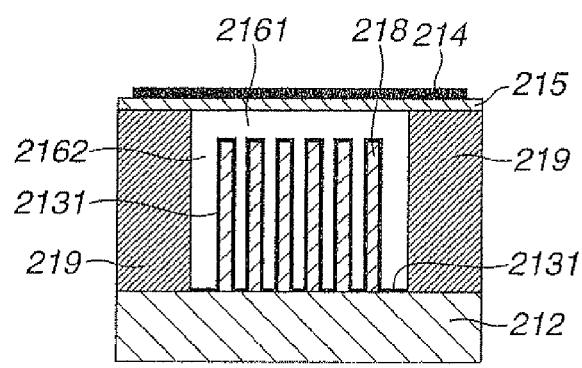
FIG. 28 is a sectional side view where lower and upper electrode, and a membrane are formed on the characteristic structure in FIG. 27.

FIG. 27 is a perspective view three dimensionally showing characteristic structure of a fifth embodiment of the present invention. FIG. 28 shows a side sectional view including lower and upper electrodes and a membrane having been formed on characteristic structure in FIG. 27.

In those drawings, reference numeral 216 denotes a cavity; reference numeral 218 denotes an elastic column; reference numeral 219 denotes a membrane supporting portion; reference numeral 2161 denotes a cavity upper gap; reference numeral 2162 denotes a cavity side portion gap; and reference numeral 2131 denotes a lower electrode. The other reference numeral is likewise in FIG. 26.

FIG. 27 is structured by a plurality of cylindrical or disk-like elastic columns 218 having been forested in the cavity 216 in FIG. 26.

And as shown in FIG. 28, the lower electrode 2131 is formed so as to cover the whole surface of respective cylinders in their entirety of a plurality of elastic columns 218. Thus, covering a plurality of elastic columns 218 to form the lower electrode 2131, acoustic impedance of the cavity 216 will vary. Accordingly, elastic columns 218 function as acoustic impedance adjustment columns.

That is, in the case where the cavity in its entirety is air, only acoustic impedance will be present, and making such structure that a plurality of elastic columns 218 are forested inside that cavity 216, intermediate and averaged impedance will be created so as to increase average acoustic impedance inside the cavity.

This means that height of a plurality of elastic columns 218 is changed variously and density is changed and thereby acoustic impedance inside a cavity can be controlled variously. Accordingly, it is possible to cause apparent acoustic impedance to get closer to the acoustic impedance of a living for acoustic matching.

Figure 29:
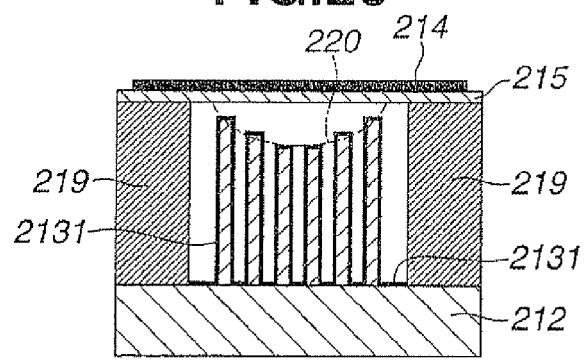
FIG. 29 is a sectional side view showing a modified example of FIG. 28.

FIG. 29 is a side sectional view showing a variation of FIG. 28. FIG. 29 is different from FIG. 28 in that column height of a forest of a plurality of elastic columns 218 gives rise to the spherical distribution curve 220. With such an arrangement, acoustic impedance viewed from the above will present a distribution property along the curved surface. An acoustic impedance property of the cavity 216 will extremely vary in the boundary to the silicon substrate, but it will become possible to smooth the change in the acoustic impedance property in the vicinity of the boundary, that is, in the periphery portion of the opening of the capacitive ultrasonic transducer by making in advance column height high in the vicinity of the boundary as in FIG. 29 and column height low in the center portion of spherical distribution curve 220.

Here, the embodiments of FIGS. 28 and 29 may be configured to cause Helmholtz resonator structure as acoustic matching means configuring capacitive ultrasonic transducer cell to intervene between an acoustic impedance adjustment column configured by a plurality of elastic columns 218 and membrane 215. That is, providing the membrane 215 in the ultrasonic transducer cell with, for example, a hole, then acoustic waves resonated in the cavity is dispatched through the hole so that it is possible to configure cavity structure with a hole that can utilize that acoustic wave, that is, Helmholtz resonator structure.

Sixth Embodiment

Figure 30:
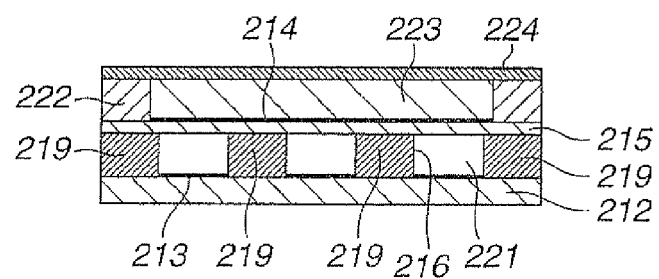
FIG. 30 is a sectional side view of a capacitive ultrasonic transducer in a capacitive ultrasonic probe of a sixth embodiment of the present invention.

FIG. 30 shows side sectional view of an capacitive ultrasonic transducer of an capacitive ultrasonic probe apparatus of a sixth embodiment of the present invention. Reference numeral 221 denotes porous material selected form the group consisting of porous silicon, porous resin and the like; reference numeral 223 denotes acoustic media such as liquid paraffin and the like; and reference numeral 224 denotes skin such as a cap and the like.

In FIG. 30, in order to take acoustic matching between acoustic impedance of a living subject and a capacitive ultrasonic transducer in use of air in the cavity 216, liquid paraffin 223 as acoustic media is disposed on the silicon substrate 212 where the cavity 216 is formed in a state with its periphery being enclosed by a spacer 222; and moreover the cap 224 is disposed as skin so that liquid paraffin 223 will never be scattered thereon. Liquid paraffin 223 is a paraffin-like and flowable liquid acoustic media, is extremely high in acoustic impedance compared with air and is closer to acoustic impedance of a living subject. And, in order to keep thickness of the layer of liquid paraffin 223 constant inside a surface, a parallel layer is designed to be formed by providing the above described spacer 222.

Here, in the case of using air as the cavity 216, the layer of liquid paraffin 223 forms the acoustic impedance matching layer bringing, into impedance matching, the apparent acoustic impedance in view of the membrane 215 and the acoustic impedance of a living not shown in contact with the skin 224.

As a condition related to acoustic impedance, it is necessary that the acoustic matching layer has thickness of the layer being a constant. That is, it is necessary to provide thickness corresponding to λ/4 (where λ is wavelength of ultrasonic wave). In order to fulfill that condition, thickness of the layer of liquid paraffin 223 as acoustic media is made constant with the spacer 222, for example, inserted between the skin 224 and the membrane 215 made of polymer film.

Next, as the cavity 216 in FIG. 30, the case in use of the porous member 221 selected from the group consisting of porous silicon, porous resin and the like will be described. This porous member is provided with extremely minute holes in silicon (Si) in the case of porous silicon. The hole is not closed but open. Since air comes in those holes, in an average, an averaged acoustic impedance value of air and silicon material will be obtainable. There is elasticity to a certain extent as well and oscillation is feasible as well. As for the direction of holes of that porous member, the direction of depth of holes is the direction of thickness. That is, the holes are dug down in the direction of thickness. An extremely great number of such holes are distributed inside the surface. Accordingly, in average, there derivable will be acoustic impedance corresponding to average addition of the volume of silicon and the volume occupied by the air layer.

Thus embedding the porous member 221 as described above into the cavity 216, material with acoustic impedance to a certain extent will come in instead of air, and only thereby acoustic matching is feasible. In that case, the above described liquid paraffin 223 only act to merely transmit ultrasonic waves to a living subject without any loss.

Seventh Embodiment

Figure 31:
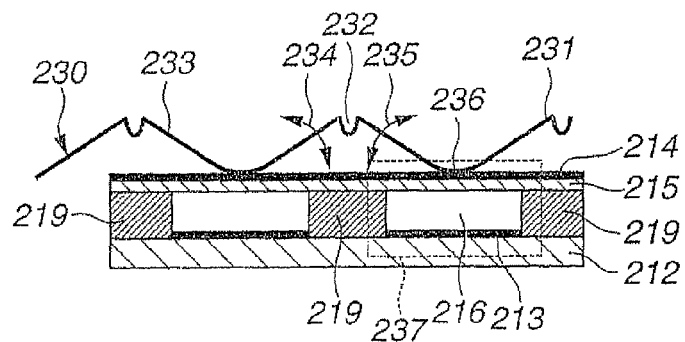
FIG. 31 is a sectional side view of a capacitive ultrasonic transducer in a capacitive ultrasonic probe of a seventh embodiment of the present invention.
Figure 32:
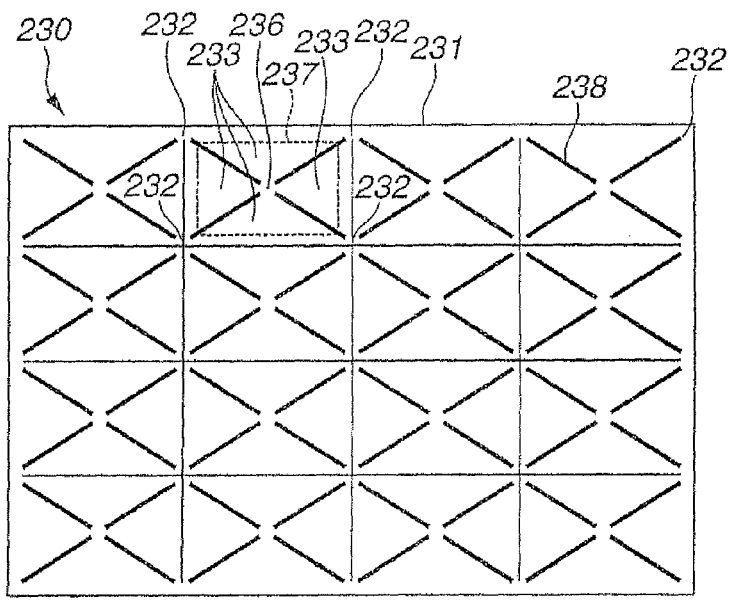
FIG. 32 is a top view of a convexoconcave polyimide sheet in FIG. 31.

FIG. 31 shows a side sectional view of a capacitive ultrasonic transducer of an capacitive ultrasonic probe apparatus of a seventh embodiment of the present invention. FIG. 32 shows a plan view of a relief polyimide sheet (hereinafter to be referred to as PI sheet) in FIG. 31. In those drawings, respectively reference numeral 230 denotes a relief PI sheet; reference numeral 231 denotes a protective film horn; reference numeral 232 denotes a crease portion; reference numeral 233 denotes a displacement portion; reference numerals 234 and 235 denote displacement; reference numeral 236 denotes a membrane center portion in capacitive ultrasonic transducer cell; reference 237 numeral denotes a capacitive ultrasonic transducer cell region; and reference 238 numeral denotes a broken ridge.

The displacement portion 233 is a slope and is formed like a bent roof. That roof shape functions as protection film and an insulating layer horn. PI sheet 230 is a polyimide sheet, therefore is resistant to chemicals and corrosion resistant to function as a protective film, and also is electrically insulative to function as an insulating layer as well. Moreover, roof-like structure functions as a horn. The position 236 corresponding to the concave portion corresponds with the center portion of membrane 25 of the capacitive ultrasonic transducer cell.

Thus horn structure with the relief PI sheet 230 will make it possible to carry out acoustic impedance conversion only with this structure itself. Structure of the lower electrode 213, the upper electrode 214, the cavity 216, the membrane 215 besides the PI sheet 230 is likewise the fifth and sixth embodiments. Here, depending on the horn shape, it is possible to provide an amplifying function for increasing ultrasonic energy, but here, the structure is intended merely for carrying out acoustic impedance conversion.

Eighth Embodiment

Figure 33:
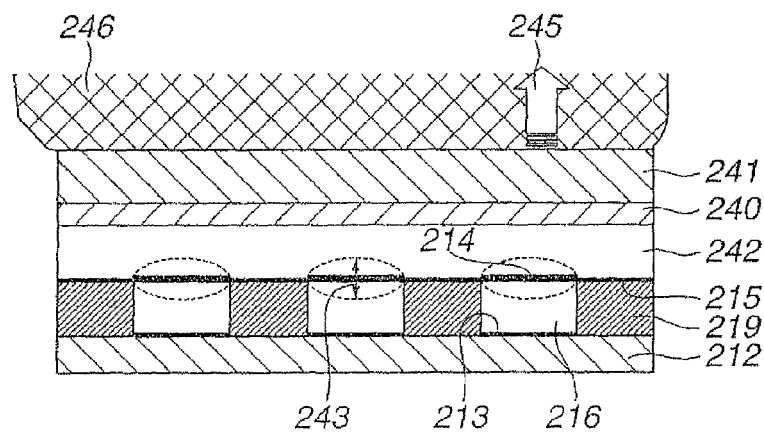
FIG. 33 is a sectional side view of a capacitive ultrasonic transducer in a capacitive ultrasonic probe of an eighth embodiment of the present invention.
Figure 34:
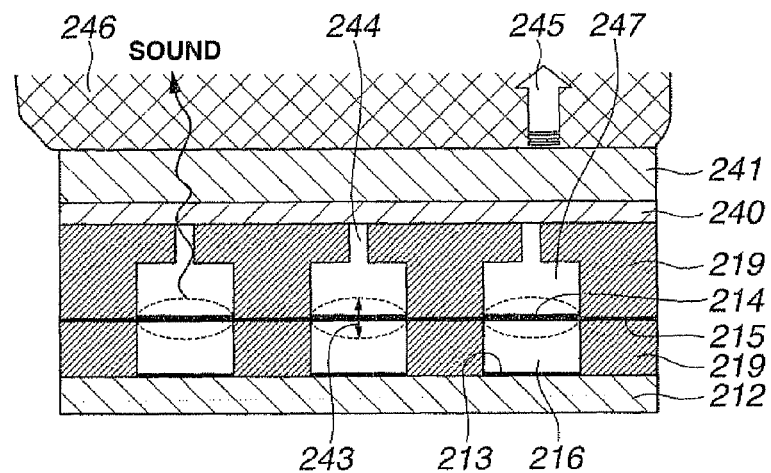
FIG. 34 is a sectional side view of a capacitive ultrasonic transducer, comprising Helmholtz cavities, in the capacitive ultrasonic probe of the eighth embodiment of the present invention.

FIGS. 33 and 34 show a side sectional view of a capacitive ultrasonic transducer of a capacitive ultrasonic probe apparatus of an eighth embodiment of the present invention. In those drawings, reference numeral 240 denotes a first acoustic matching layer; reference numeral 241 denotes a second acoustic matching layer; reference numeral 242 denotes an air layer; reference numeral 244 denotes an ultrasonic radiation hole; reference numeral 245 denotes an ultrasonic transmission direction; reference numeral 246 denotes a diagnostic object; and reference numeral 247 denotes a hollow layer. Here, polymer film forming membrane 215 is configured by flexible film and reference numeral 243 denotes an oscillation displacement of the flexible film.

FIG. 33 is for structure causing a plurality of (two in the drawing) acoustic matching layers 240 and 241 and air layer 242 to intervene between the diagnostic object 246 and the membrane 215 made of polymer film of a normally configured capacitive ultrasonic transducer including the lower electrode 213 being formed on the bottom of the cavity 216 formed with air; the membrane 215 being formed on the cavity 216, and the upper electrode 214 being disposed further thereon.

The acoustic matching layer 240 for the first layer is porous silicon resin and the acoustic matching layer 241 for the second layer is silicon resin. As the total number of layers carrying out acoustic matching increases, more accurate acoustic matching will become feasible.

Porus silicon resin includes silicon resin as base material to form silicon resin film. Silicon resin film undergoes processing to shape porous and that is used as acoustic matching layer film. Acoustic impedance of porous silicon resin will result in a middle value between that of air and silicon resin lacking holes since air comes in the porous. And, silicon resin lacking holes for the second layer is present and finally connected with a living subject being a diagnostic object.

Acoustic matching is carried out, in the case where acoustic impedance $(\rho c)o$ of an object is different from acoustic impedance $(\rho c)s$ of the sound source, by causing a layer having middle acoustic impedance $(\rho c)m$ thereof to intervene between the both. Accordingly, in the case where two layers m1 and m2 are present as the intervening layer, taking acoustic impedance thereof as $(\rho c)m1$ and $(\rho c)m2$ respectively, it is necessary to fulfill:

$$(\rho c)s < (\rho c)m1 < (\rho c)m2 < (\rho c)o$$

Accordingly, silicon resin m2 being $(\rho c)m2=1$ will derive $(\rho c)m1<1$.

Since acoustic impedance of air layer 242 is $\ll 1$, relationship of $\rho c$ will be as follows:

$$(\rho o)s < (\rho c)m1 < (\rho o)m2 < (\rho c)o$$

Here as for $\rho c$, $(\rho c)s=10-2\text{Mrayl}$, $(\rho c)m1\ll 1.0\text{Mrayl}$, $(\rho c)m2=1.0\text{Mrayl}$, $(\rho c)o=1.5\text{Mrayl}$, for example.

FIG. 34 shows an example of structure called Helmholtz cavity. The membrane 215 made of flexible film is formed in the middle of the silicon substrate 21. In the silicon substrate 212, the cavity 216 and the hollow layer 247 opposite thereto are formed with the membrane 215 being a boundary, and the ultrasonic radiation hole 244 piercing through the silicon substrate 212 is provided in substantially the center of the hollow layer 247. And on the surface on the ultrasonic dispatch side where the hole 244 of the silicon substrate 212 is formed, acoustic matching layers 240 and 241 comprising two layers are formed. Likewise in FIG. 33, the lower electrode 213 is formed on the bottom surface of the cavity 216 and the upper electrode 214 is formed on the membrane 215 facing this lower electrode 213.

Thus, the providing hollow layer 247 on the membrane 215 in the ultrasonic transducer cell so as to face the cavity 216 and providing, for example, a hole 244 there, acoustic waves having resonated in the cavity 216 and the hollow layer 247 go through the hole 244 and are dispatched through the acoustic matching layers 240 and 241 on the ultrasonic radiation side of the silicon substrate 212 so that those acoustic waves will become utilizable.

Ninth Embodiment

Figure 35:
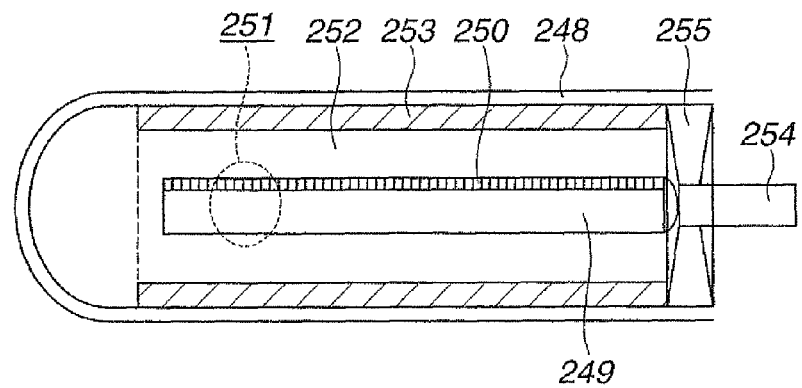
FIG. 35 is a sectional side view of a capacitive ultrasonic transducer in a capacitive ultrasonic probe of a ninth embodiment of the present invention.
Figure 36:
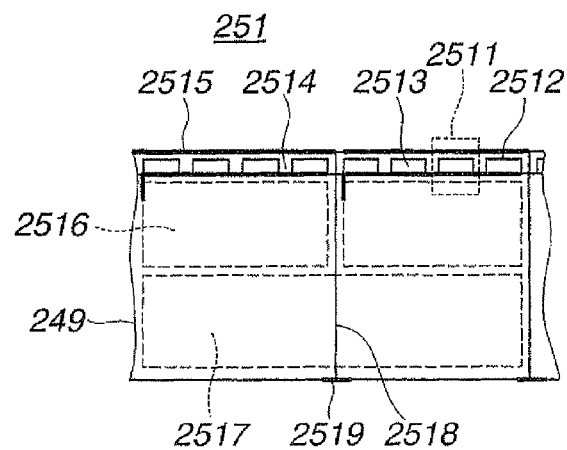
FIG. 36 is a sectional side view showing enlargingly a part of the capacitive ultrasonic transducer array in FIG. 35.

FIGS. 35 and 36 show a side sectional view of a capacitive ultrasonic transducer of a capacitive ultrasonic transducer probe apparatus of a ninth embodiment of the present invention. In those drawings, respectively reference numeral 248 denotes a sheath; reference numeral 249 denotes a silicon substrate; reference numeral 250 denotes a capacitive ultrasonic transducer array; reference numeral 251 denotes a capacitive ultrasonic transducer array piece; reference numeral 252 denotes an air layer; reference numeral 253 denotes an acoustic matching layer; reference numeral 254 denotes a coaxial cable; reference numeral 255 denotes an isolation wall; reference numeral 2511 denotes a capacitive ultrasonic transducer cell; reference numeral 2512 denotes a membrane; reference numeral 2513 denotes a hollow portion; reference numeral 2514 denotes a lower electrode; reference numeral 2515 denotes an upper electrode; reference numeral 2516 denotes a control circuit (SW circuit); reference numeral 2517 denotes a control circuit; reference numeral 2518 denotes an interconnect; and reference numeral 2519 denotes an outside contact electrode.

The capacitive ultrasonic transducer array 250 prepared with semiconductor processing on the silicon substrate 249 is housed in the tube-like sheath 248 and is isolated from the outside with the isolation wall 255. The coaxial cable 254 electrically connected to the capacitive ultrasonic transducer array 250 and the silicon substrate 249 are pulled from the sheath 248 to the outside. The air layer 252 is present between the capacitive ultrasonic transducer array 250 and the sheath 248 and next thereto the acoustic matching layer 253 formed on the inner surface of the sheath 248 is formed. And, a living subject being a diagnostic object comes to the outside that sheath 248.

Using material with acoustic impedance close to that of a living subject as the sheath 248, acoustic matching will be carried out in the order of the capacitive ultrasonic transducer, air, the acoustic matching layer, sheath material and a living subject.

FIG. 36 shows a portion of the capacitive ultrasonic transducer array piece 251 in FIG. 35 in an enlarged fashion. Silicon substrate 249 has thickness, and therefore can build control circuits 2516 and 2517 in. The control circuit 2516 is a switch circuit while the control circuit 2517 is, for example, a power amplifier and a charge amplifier. The interconnect 2518 is formed to pierce the silicon substrate; the hollow portion 2513 is present in the direction of thickness of the silicon substrate; and the membrane 2512 and the upper electrode 2515 are present on the exterior surface of the hollow portion 2513. The lower electrode 2514 is present in the lower portion of the hollow portion 2513. Wiring is lead to the opposite surface side of the silicon substrate 249 though the interconnect 2518.

A drive signal generating portion, a power amplifier and a charge amplifier are configured in the vicinity of the capacitive ultrasonic transducer with semiconductor silicon processing to transmit signals subjected to conversion into low impedance, and thereby it will become possible to deprive the coaxial cable 254 of loss.

Tenth Embodiment

Figure 37:
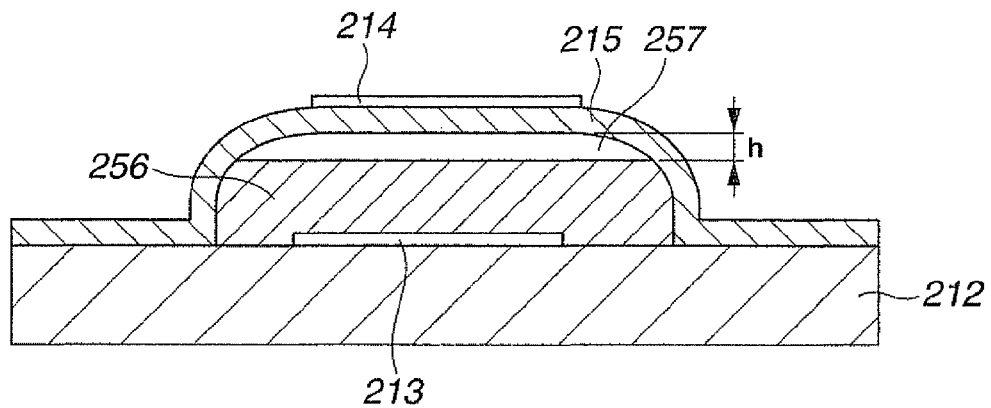
FIG. 37 is a sectional side view of a capacitive ultrasonic transducer cell in a capacitive ultrasonic probe of a tenth embodiment of the present invention.

FIG. 37 shows a side sectional view of a capacitive ultrasonic transducer of a capacitive ultrasonic probe apparatus of a tenth embodiment of the present invention. In this drawing, respectively reference numeral 256 denotes a resin layer, reference numeral 257 denotes a gap layer.

The lower electrode 213 is formed on the surface of the silicon substrate 212; the resin layer 256 is disposed thereon; moreover polymer film functioning as the membrane 215 is formed on silicon substrate 212 so that a predetermined height is given by the resin layer 256 and the gap layer 257 provided thereon; and moreover the upper electrode 214 is formed on polymer film which constitutes the membrane 215 with the resin layer 256 and the gap layer 257 provided with a predetermined height. That will enhance the apparent acoustic impedance inside the cavity formed between the lower electrode 213 and the upper electrode 214 to get closer to acoustic impedance of a living subject being a diagnostic object.

Thus, as the resin layer 256 disposed inside the cavity, in use of the one with acoustic impedance closer to that of a living subject, acoustic impedance of the cavity can be made not to be acoustic impedance of air but to be higher than that. The gap layer 257 besides the resin layer in the cavity is like an air layer and adjustment in height h of this gap layer 257 makes it possible to optimize acoustic impedance. Here, instead of the resin layer 256, a liquid layer may be adopted. However, in the case of using liquid, it is necessary to fulfill the cavity in its inside with liquid or to provide a device for retaining constant thickness.

The fifth to the tenth embodiments of the present invention described above will make effective acoustic impedance feasible and therefore is useful for utilization in the technology of extracting minute harmonic components from echo signals in receipt to obtain harmonic imaging diagnostic image.

Eleventh Embodiment

Figure 38:
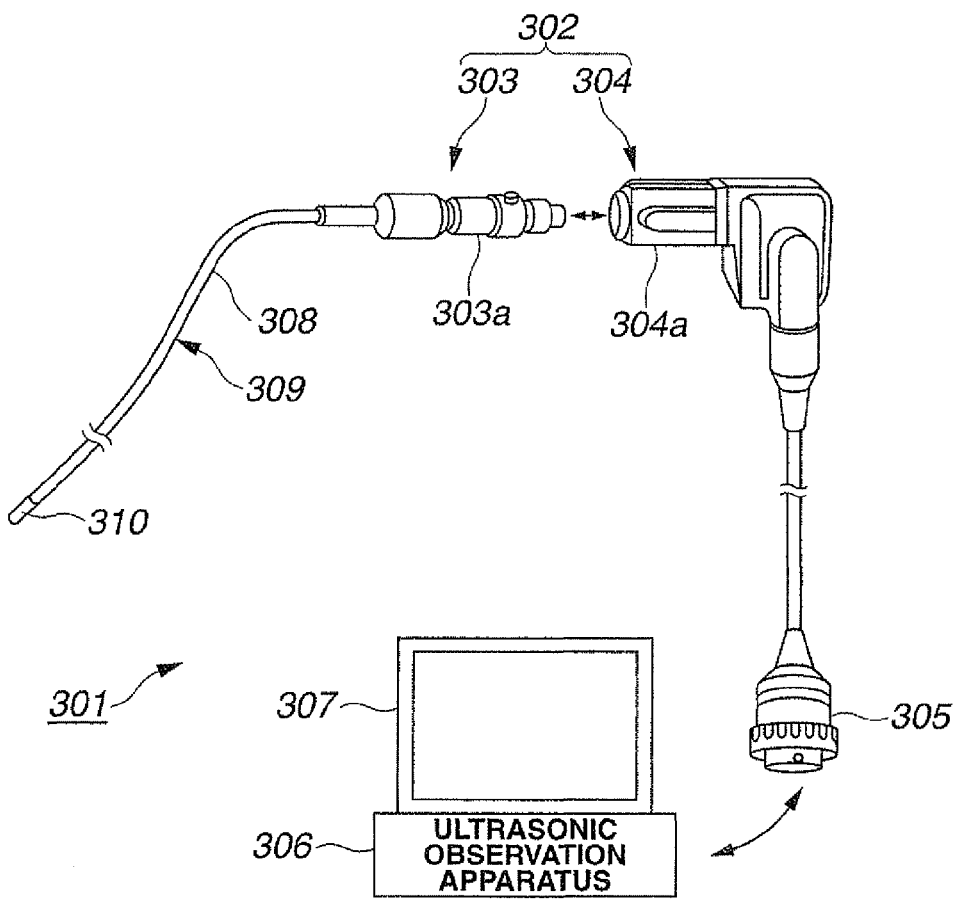
FIG. 38 is a general view showing structure of an ultrasonic diagnostic apparatus, comprising a capacitive ultrasonic probe for body cavity insertion, according to an eleventh embodiment of the present invention.
Figure 39:
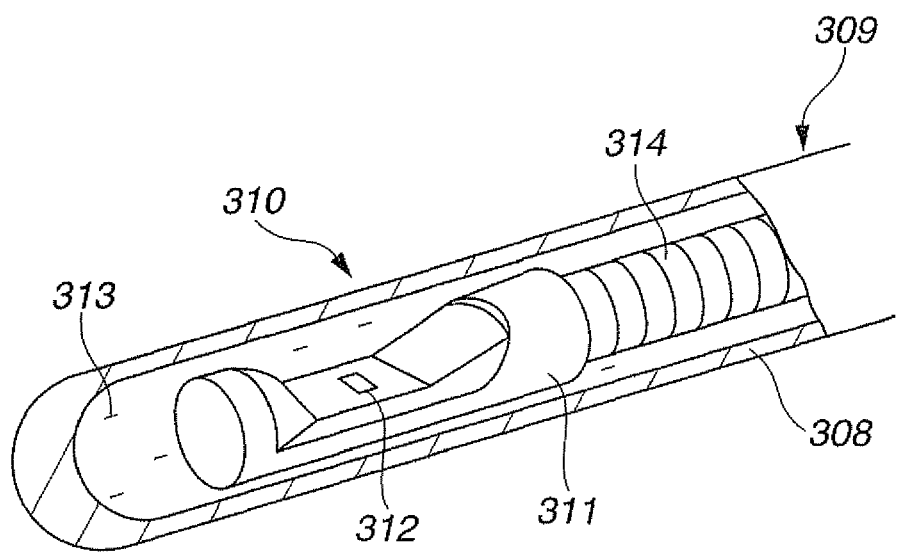
FIG. 39 is a partially cutaway perspective view showing structure of an edge side of the capacitive ultrasonic probe for body cavity insertion according to the eleventh embodiment of the present invention.
Figure 40:
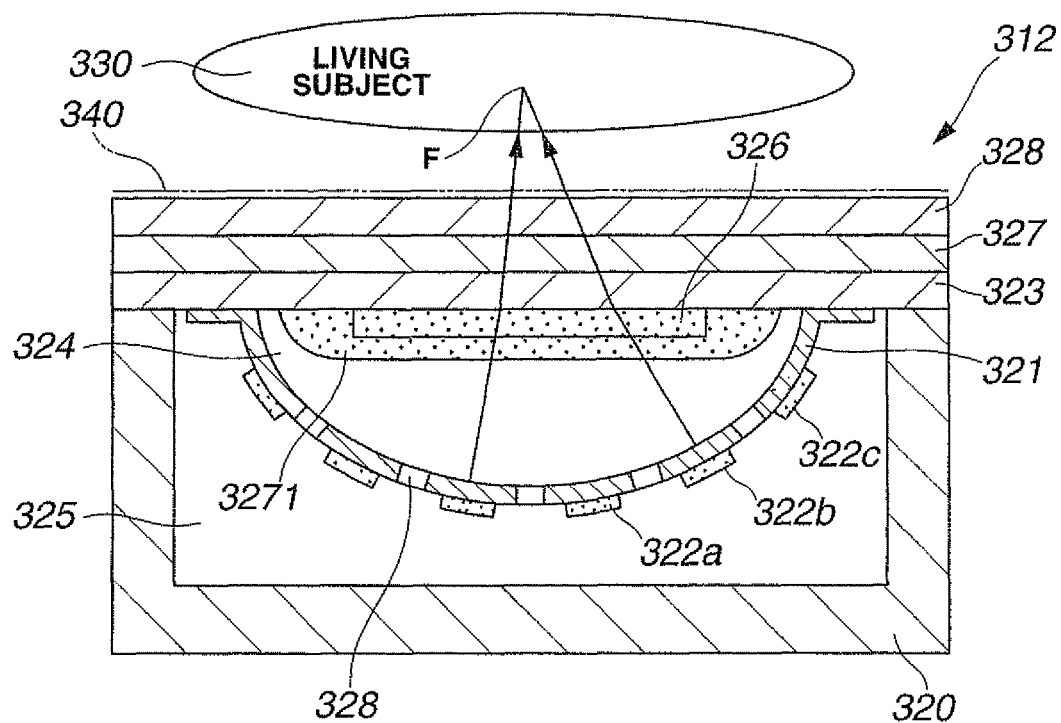
FIG. 40 is a sectional view showing structure of a capacitive ultrasonic transducer element.
Figure 41:
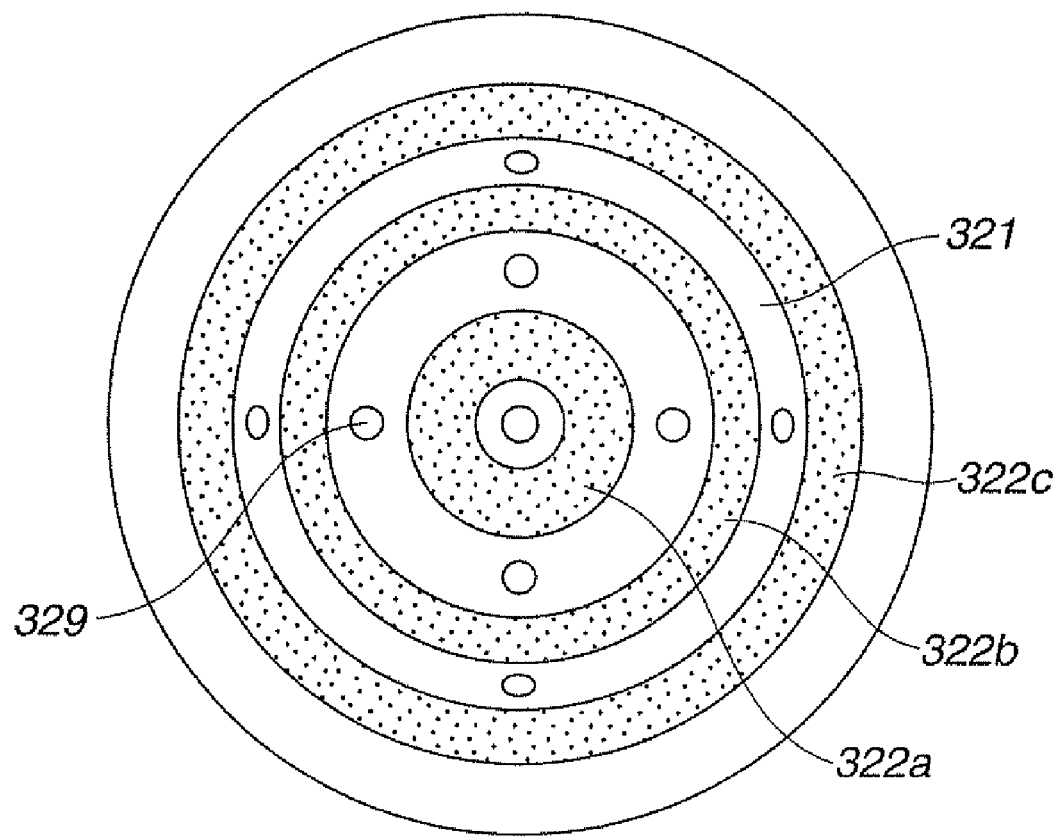
FIG. 41 is a diagram showing forms of membranes and the like in view of a bottom face side in FIG. 40.
Figure 42:
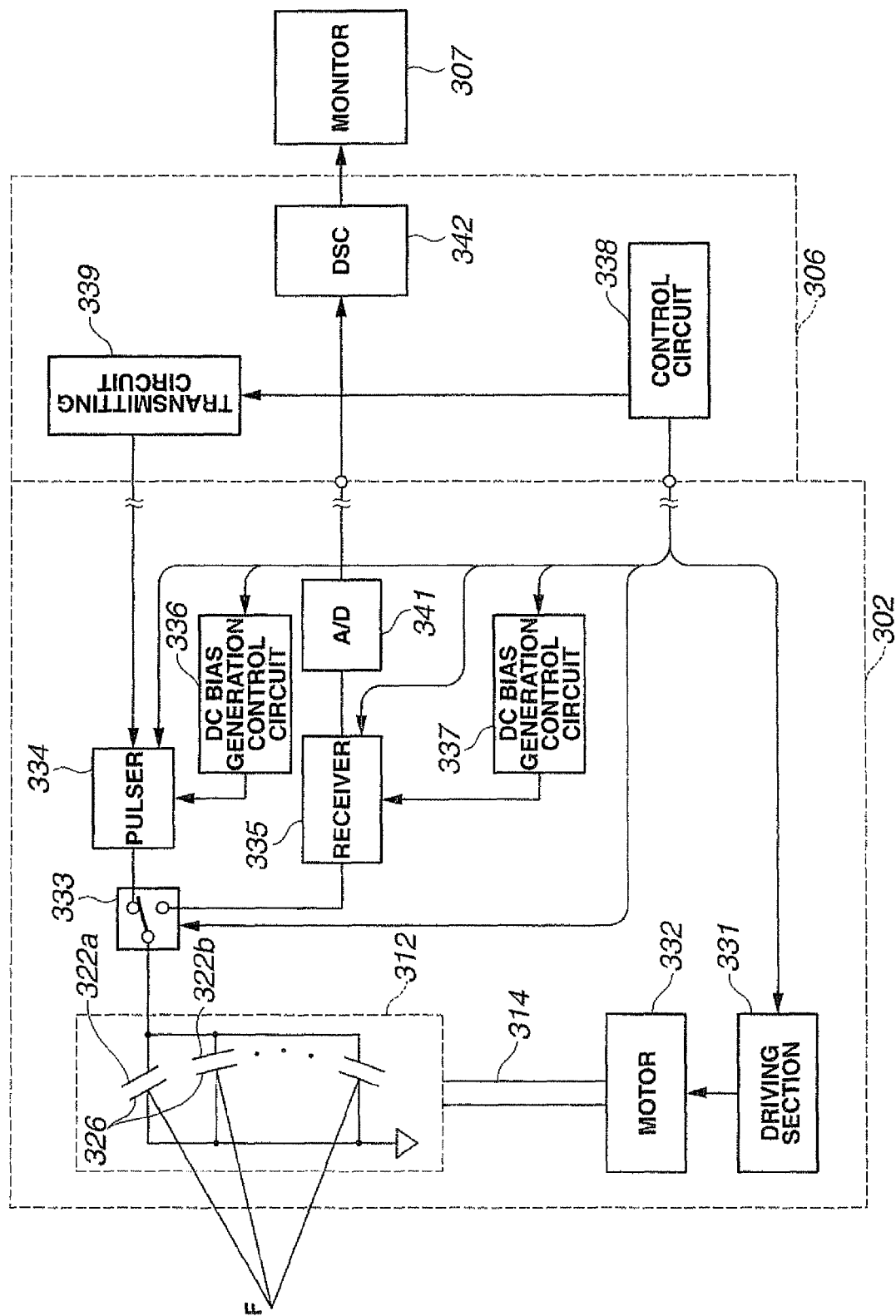
FIG. 42 is a block diagram showing structure of an electric system driving a capacitive ultrasonic transducer element.
Figure 43:
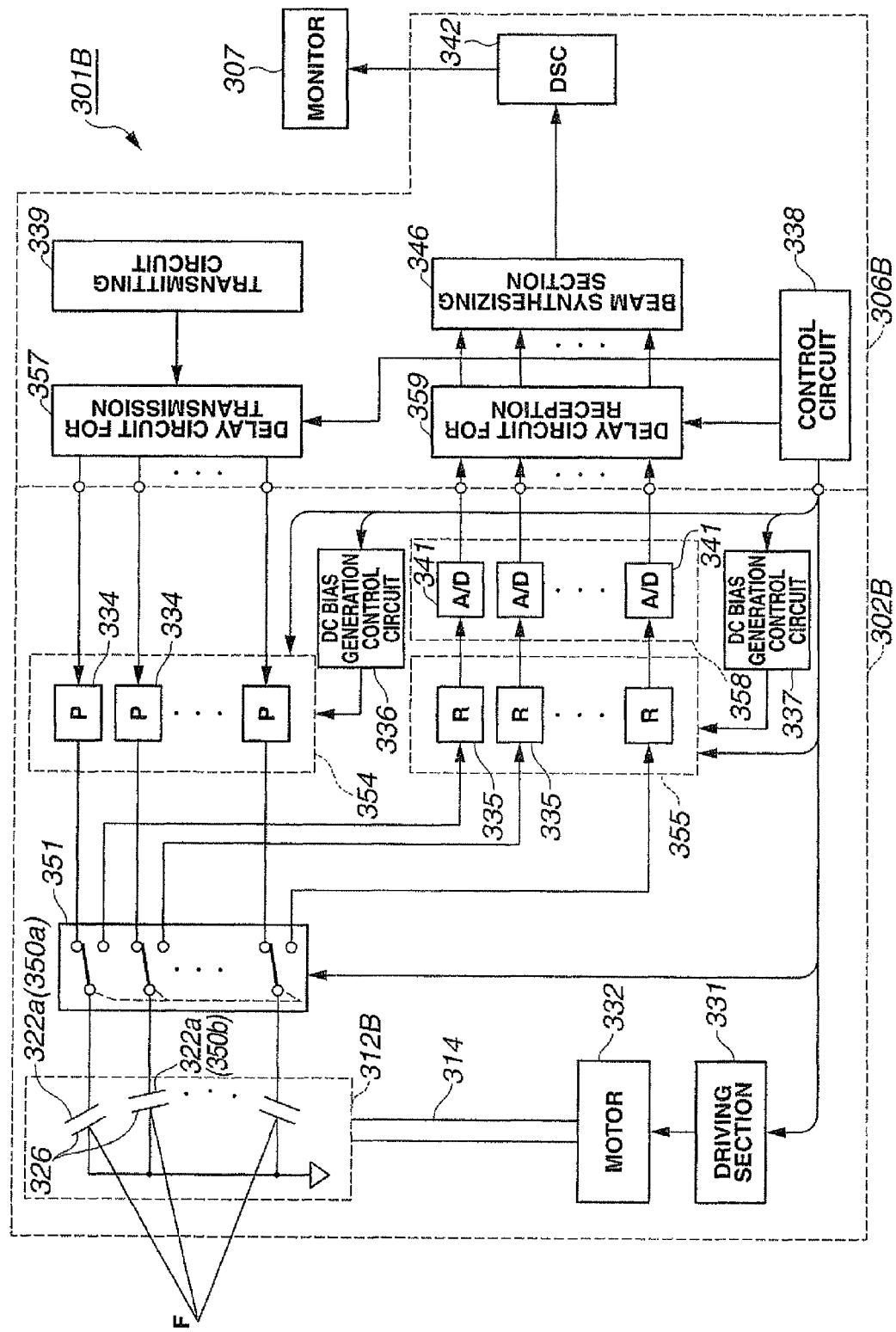
FIG. 43 is a block diagram showing structure of an electric system driving a capacitive ultrasonic transducer array in a modified example.

FIGS. 38 to 43 relate to an eleventh embodiment of the present invention, FIG. 38 showing a configuration of an ultrasonic diagnostic apparatus comprising a body cavity insertion capacitive ultrasonic probe of the eleventh embodiment of the present invention; FIG. 39 showing a configuration on the tip side of the body cavity insertion capacitive ultrasonic probe of the eleventh embodiment; FIG. 40 showing a configuration of a capacitive ultrasonic transducer element; FIG. 41 showing shapes of a membrane and the like viewed from the bottom side in FIG. 40; FIG. 42 showing a configuration of an electric system for driving the capacitive ultrasonic transducer element; and FIG. 43 showing a configuration of an electric system for driving the capacitive ultrasonic transducer array in a variation.

An ultrasonic diagnostic apparatus shown in FIG. 38 has a body cavity insertion capacitive ultrasonic probe (hereinafter to be abbreviated as capacitive ultrasonic probe) 302 of the eleventh embodiment which can be inserted into a channel of an endoscope not shown in the drawing.

This capacitive ultrasonic probe 302 comprises a capacitive ultrasonic probe main body 303, a capacitive ultrasonic probe main body 303 and a drive unit 304 provided with a joint portion 304a to which a joint portion 303a at the rear end of this capacitive ultrasonic probe main body 303 is connected in a detachably attachable fashion. This drive unit 304 is provided, in its inside with a built-in rotation drive mechanism such as a motor for rotary driving a capacitive ultrasonic transducer built-in in the capacitive ultrasonic probe main body 303.

From this drive unit 304, a cable portion 304b is extended, and a connector 305 provided at its back end is connected in a detachably attachable fashion. This ultrasonic observation apparatus 306 is connected to a monitor 307; a video signal is inputted from an ultrasonic observation apparatus 306 to the monitor 307 which displays an ultrasonic cross-sectional image corresponding with this video signal.

The capacitive ultrasonic probe main body 303 is covered by a longitudinal and flexible sheath 308 to form an insertion portion 309 and this insertion portion 309 can be inserted into a channel of the endoscope.

At the forward tip of this capacitive ultrasonic probe main body 303, there provided is an ultrasonic probe head portion 310 as shown in FIG. 39.

As shown in FIG. 39, the forward tip of the cylindrical sheath 308 is blocked to form the ultrasonic probe head portion 310, and there housed inside this ultrasonic probe head portion 310 is a housing 311 on which a capacitive ultrasonic transducer inclusive of the capacitive ultrasonic transducer element 312 is mounted. Interior of this sheath 308 is filled with ultrasonic transmission media 313 for transmitting ultrasonic waves.

This housing 311 on which the capacitive ultrasonic transducer inclusive of the capacitive ultrasonic transducer element 312 is mounted is mounted on the forward tip of flexible shaft 314 inserted inside the sheath 308.

The back end of this flexible shaft 314 is connected to a rotation shaft of the motor 315 as shown in FIG. 42 and this motor 315 rotates with a drive signal from the drive portion 317. And, rotary power of this motor 315 is transmitted to the housing 311 through the flexible shaft 314 and the capacitive ultrasonic transducer element 312 mounted on the housing 311 rotates so that the ultrasonic beam transmitted from this capacitive ultrasonic transducer element 312 is allowed to undergo radial scanning.

The capacitive ultrasonic transducer element 312 of the present embodiment is made to have sectional structure as shown in FIG. 40.

A curved membrane 321 is fixed in its periphery; the membrane 321 made of thin film which can vibrate and is spherically shaped or dome shape similar thereto is disposed inside the concave portion of an enclosure 320 supporting a substrate 323 where an electrode 326 is disposed; and any one of surface of this membrane 321 is provided with lower electrodes 322a, 322b and so on.

In addition, the periphery in the membrane 321 blocks the opening on the upper side of the concave portion of the enclosure 320 and is fixed to the lower surface of the substrate 323 shaped like a flat plate such as a cover plate forming the gap portion.

Inside the concave portion blocked by the substrate 323, the dome-like membrane 321 is disposed and thereby there formed in the concave portion are a front surface gap portion 324 surrounded by this dome-like membrane 321 and the substrate 323 and a rear surface gap portion 325 surrounded by the rear surface of the membrane 321 and the bottom side of the enclosure 320.

The present embodiment is provided with the concentric and annular lower electrodes 322a, 322b and so on on the lower surface of the dome-like membrane 321 as shown in FIG. 41. Here, FIG. 441 shows a drawing of the lower electrodes 322a, 322b and so on viewed from the side of the rear surface gap portion 325 of the concave portion in FIG. 40.

In addition, a disk-like upper electrode 326 is provided so that its center faces near the center of the dome-like membrane 321 on the bottom surface of this substrate 323 and there formed is the capacitive ultrasonic transducer element 312 which applies a drive signal in the state with DC bias voltage being applied between that upper electrode 326 and the annular lower electrodes 322a, 322b and thereby vibrate the membrane 321 to transmit ultrasonic waves.

In addition, the upper surface of the substrate 323 is provided with, as acoustic matching means, a first acoustic matching layer 327 and a second acoustic matching layer 328 provided on the upper surface of this first acoustic matching layer 327 so that ultrasonic waves can be transmitted to the living subject 330 side efficiently and ultrasonic waves from the living subject 330 side can be received efficiently.

In addition, also between the bottom surface of the rigid substrate 323 and the air layer portion of the forward surface gap portion 324, an acoustic matching layer 3271 having acoustic impedance being middle of the both is provided so as to cover the surface of the upper electrode 326 mounted on the bottom surface of this substrate 323. Here, the first acoustic matching layer 327 and the second acoustic matching layer 328 may be a one-layer acoustic matching layer.

Here, the dome-like membrane 321 is provided with small vents 329 at several points.

Thus in the capacitive ultrasonic transducer element 312 in the present embodiment, virtually annular capacitive ultrasonic transducer cells (abbreviated as transducer cells) are designed to be formed with a plurality of lower electrodes 322a, 322b and so on provided on the lower surface of the dome-like membrane 321 and upper electrode 326 provided on the bottom surface of the substrate 323 through the forward surface gap portion 324, and with the membrane portion provided with the respective lower electrodes 322a, 322b and so on.

And, an ultrasonic beam transmitted to the side of living subject 330 is structured to allow concentration even if drive signal application timing is not displaced for each electrode located differently on the membrane 311 since the membrane 321 has been formed to be substantially hemispheroidal in the case where a drive signal with the same phase has been applied between the respective lower electrodes 322a, 322b and so on respectively located differently from the common upper electrode 326 as shown in FIG. 40.

That is, the capacitive ultrasonic transducer element 312 in the present embodiment is characterized in that the shape of that membrane 321 portion structurally comprises a focusing function of focusing ultrasonic waves. Here, rigidness of the membrane 321 has elasticity to allow vibration while retaining a curved surface and is set to be flexible than the substrate 323.

Taking such a configuration, in FIG. 40, for example, ultrasonic waves transmitted from the membrane 321 portion provided with the lower electrode 322a and ultrasonic waves transmitted from the membrane 321 portion provided with the lower electrode 322b are transmitted to the living subject 330 side as indicated by the arrowed line and are focused at the focusing point F inside the living subject 330.

Here, as shown with a two-dot chain line 340 in FIG. 40, coating film 340 of parylene resin being resistant against chemicals and the like may be provided on the upper surface of the capacitive ultrasonic transducer element 312 of the second acoustic matching layer 328 to protect the capacitive ultrasonic transducer element 312 in its entirety in its inside.

FIG. 42 shows a configuration of a control system of the ultrasonic diagnostic apparatus 301 comprising the present embodiment.

The motor 332 of carrying out rotary drive with a drive signal from the drive portion 331 is brought into connection so as to be capable of rotary driving the capacitive ultrasonic transducer element 312 mounted on a housing 311 not shown in FIG. 42 through the flexible shaft 314 linked to the rotary shaft thereof.

The lower electrodes 322a, 322b and so on are formed concentrically on the bottom surface in the dome-like membrane 321 configuring the capacitive ultrasonic element 312 and the membrane portion where the lower electrodes 322a and 322b are formed configures a plurality of transducer cells equivalently in the same annular shape.

Those lower electrodes 322a, 322b and so on are commonly connected to a transmission/reception switching switch 333 and from there are connected to a pulser 334 of generating transducer drive signal and to a receiver 335 of amplifying the received signal. Here, the upper electrode 326 is connected to the ground.

In addition, the pulser 334 and the receiver 335 are respectively connected to DC bias generation control circuits 336 and 337. And operation of those pulser 334, receiver 335 and DC bias generation control circuits 336 and 337 are controlled by a control signal from a control circuit 338 inside the ultrasonic observation apparatus 306.

In addition, the ultrasonic observation apparatus 306 is provided in its inside with a transmission circuit 339 of generating an RE signal for transmission with low voltage, and this transmission circuit 339 generates and outputs to the pulser 334 the RF signal with pulsed low voltage at a predetermined period based on the control signal from the control circuit 338.

Low voltage DC bias control pulse is inputted to the pulser 334 with timing to become slightly before timing when this low voltage RF signal is inputted and with pulse width slightly wider than the pulse width of the RF signal.

And this pulser 334 generates transducer drive signal where high voltage RF signal is superimposed onto high voltage DC bias pulse by summing-amplifying the RF signal onto DC bias control pulse and applies simultaneously to the respective lower electrodes 322a, 322b and so on of the capacitive ultrasonic transducer element 312 through the transmission reception switching switch 333 switching this transducer drive signal with a switching control signal from the control circuit 338.

Thus in the present embodiment, an output signal from the pulser 334 is applied to each transducer cell configuring the capacitive ultrasonic transducer element 312 simultaneously.

In that case, in the present embodiment, pulsed high voltage PC bias voltage has pulse width almost the same as pulse width of the high voltage RF signal and therefore will become an extremely short period compared with the repeat period for transmitting ultrasonic waves and effective voltage thereof is made capable to become extremely small.

And, as shown in FIG. 40, in the case of applying the drive signal to each transducer cell simultaneously, the respective transducer cells transmit ultrasonic waves and in that occasion, the membrane 321 has a spherical shape or a dome-like shape and therefore an ultrasonic beam with high acoustic pressure focused at the specific focusing point F will be obtained on the living subject 330 side.

Immediately after ultrasonic waves are transmitted from each transducer cell, transmission/reception switching switch 333 is switched with a switch control signal from control circuit 338 so as to be conducted with the receiver 335 side and the transducer cell will enter the state of receiving ultrasonic waves. And, the received RF signals which are received by each transducer cell and converted into electric signals are amplified with the receiver 335.

Also in that case, each transducer cell receives simultaneously signals from the specific focusing point F and therefore ultrasonic received signals with good S/N are obtainable.

Here, in that case, the receiver 335 amplifies the received signals, converts them into low impedance and outputs them in an ON state where DC bias voltage is applied to each transducer cell.

The received signals amplified by that receiver 335 become digital received signal data with the A/D conversion circuit 341 and are inputted to a digital scan converter (abbreviated as DSC) 342 inside the ultrasonic observation apparatus 306 through a cable inserted inside the drive unit 304 and a cable inserted inside the flexible shaft 314 inside the capacitive ultrasonic probe main body 303.

Thus, in the above described embodiment, the received signals transmitted from the cable inserted inside the capacitive ultrasonic probe main body 303 are set to be digital signals, which are, therefore, not susceptible to transmission loss due to cables compared with the case of analog signals so that deterioration of S/N can be prevented.

The DSC 342 converts inputted digital received signal into video signals to output to the monitor 307 and an ultrasonic cross-sectional image is displayed on the display window of the monitor 307.

The present embodiment gives rise to the following effects.

Thus in the capacitive ultrasonic transducer element 312 in the present embodiment, a plurality of transducer cells are concentrically formed in the dome-like membrane 321 and the transducer drive signal is simultaneously applied to a plurality of transducer cells hereof and thereby ultrasonic beams can be focused at a predetermined position.

Accordingly, without using a delay circuit and the like for electrically adjusting timing to drive a plurality of transducer cells, and with simple configuration, intensity of ultrasonic beams can be enlarged and also in the case of reception, the received signal is obtainable in a state with good S/N. In addition, an ultrasonic cross-sectional image with good picture quality will be obtainable as well.

In addition, the pulser 334 and the receiver 335 do not have to be prepared in plurality, but a singular number thereof will do, being possible to make the circuit size for transmission and reception small and reduction in size and cost can be feasible.

In the above described embodiment, the bottom surface of the membrane 321 is provided with the concentric lower electrodes 322a, 322b and so on, but as a variation, the lower electrodes may be formed convolutedly, for example.

In addition, in the above described description, concentric lower electrodes 322a, 322b and so on are configured to be commonly connected to the bottom surface of the membrane 321 as shown in FIG. 42 to transmit ultrasonic waves with a drive signal of the same phase, but, giving up common connection of the concentric lower electrodes 322a, 322b and so on, and they may be driven with respectively different timing.

Such a configuration will make it possible to set the focus again electronically with a fixed focus as a center.

FIG. 43 shows a configuration of an ultrasonic diagnostic apparatus 301B in a variation. This ultrasonic diagnostic apparatus 301B is configured by a capacitive ultrasonic probe 302B, an ultrasonic observation apparatus 306B and a monitor 307.

This ultrasonic diagnostic apparatus 301B gives up common connection of the concentric lower electrodes 322a, 322b and so on in the capacitive ultrasonic transducer element 312 and has structure of the capacitive ultrasonic transducer array 312B provided with respectively separate terminals.

In that case, the concentric lower electrodes 322a, 322b and so on are respectively separate, and therefore, the transducer cells in FIG. 42 will be virtually changed to the transducer elements 350a, 350b and so on in configuration.

And the transducer elements 350a, 350b and so on provided with the concentric lower electrodes 322a, 322b and so on are connected to the pulser portion 354 and the receiver portion 355 through each switch element of the switching switch 351. The pulser portion 354 and the receiver portion 355 are configured by the transducer element number of the pulsers 334 and the receivers 335.

In addition, DC bias control signals are applied from the DC bias generation control circuits 336 and 337 to the pulser portion and the receiver portion 355.

In addition, the ultrasonic observation apparatus 306B inputs the RF signal for transmission of the transmission circuit 339 to the delay portion 357 for transmission; and the delay portion 357 for transmission delays the transmission signal with the control signal for correction from the control circuit 338 respectively with a plurality of delay circuits and outputs them to the pulser 334.

That is, to the transducer elements 350a, 350b and so on configured by providing with the concentric lower electrodes 322a, 322b and so on a drive signal is made applicable at different timing.

In addition, in the present embodiment, the received signal received by the transducer elements 350a, 350b and so on is inputted to each A/D conversion circuit 341 of the A/D conversion portion 358 through the receiver 335 of the receiver portion 355 and undergoes A/D conversion.

The digital received signal having undergone A/D conversion is inputted to the reception delay circuit 359 inside the ultrasonic observation apparatus 306B and delay amounts are respectively adjusted with a control signal from the control circuit 338. And, the delayed received signal is inputted to the beam synthesizing section 346 so as to undergo beam synthesizing to generate one received signal.

The received signal having undergone this beam synthesizing is inputted to the DSC 342 and is converted into a video signal and then is outputted to the monitor 307 so that an ultrasonic cross-sectional image will be displayed on the display window of the monitor 307.

According to the present variation, even if dispersion is present in the shape of the membrane 321 in the fabricated capacitive ultrasonic transducer element, for example, adjusting the delay amount in the delay portion 357 for transmission and the delay portion 359 for reception, dispersion on its property can be absorbed.

Therefore, deviation allowable at the time of fabrication can be made large and can reduce fabrication costs.

In this case, in the delay portion 357 for transmission and the delay portion 359 for reception, the necessary delay amount may be small and therefore a small size can be realized.

In addition, according to the configuration of the present variation, adjusting the delay amount in the above described delay portion 357 for transmission and the delay portion 359 for reception, the position of the focusing point of ultrasonic waves can be changed.

Twelfth Embodiment

Next, a twelfth embodiment of the present invention will be described with reference to FIGS. 44A to 44C. A capacitive ultrasonic probe of the twelfth embodiment adopts a capacitive ultrasonic transducer element 312C with structure different from the capacitive ultrasonic transducer element 312 shown in FIG. 40 mounted on the housing 311 in FIG. 39 in the eleventh embodiment.

Figure 44A:
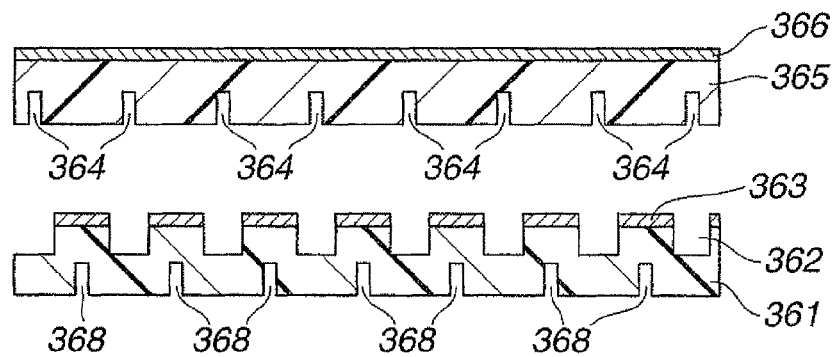
FIG. 44A is an explanatory diagram showing a state before bonding in a production process of a capacitive ultrasonic transducer element in a twelfth embodiment of the present invention.
Figure 44B:
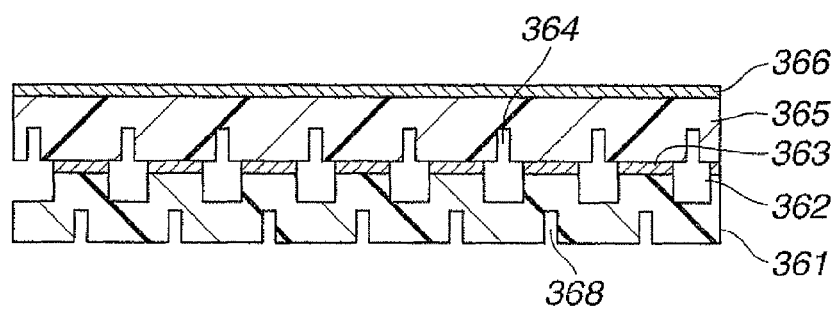
FIG. 44B is an explanatory diagram showing a state after bonding in the production process of the capacitive ultrasonic transducer element in the twelfth embodiment of the present invention.
Figure 44C:
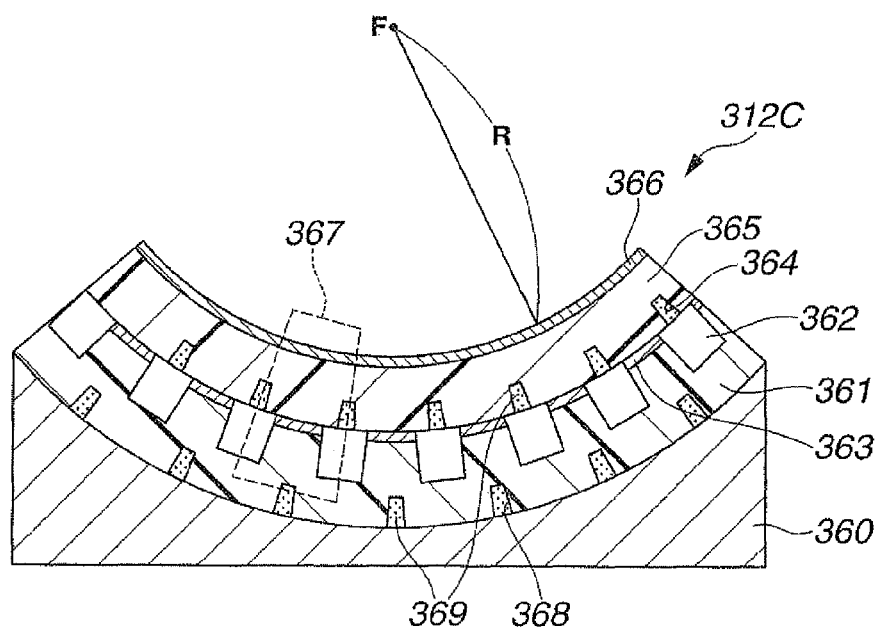
FIG. 44C is an explanatory diagram of forming a spherical shape in the production process of the capacitive ultrasonic transducer element in the twelfth embodiment.

Structure of the capacitive ultrasonic transducer element 312C in the present embodiment is shown in FIG. 44C. In this capacitive ultrasonic transducer element 312C, a flexible substrate 361 made of silicon resin and the like is bonded and fixed in a bent state on the upper surface of a rigid base 360 where a spherical concave portion is formed, small indentations or concave portions 362 are formed two dimensionally, in a predetermined distance and the like on the upper surface of this bent substrate 361.

As silicon resin, polydimethylsiloxane (abbreviated as PDMS) and SU-8 (product name at Micro Chemical Corporation) can be used. Here, as PDMS, those made of KE106VE (Shin-Etsu Chemical Co. Ltd.) and SILPOT184(Dow Corning) can be adopted.

In addition, respectively a flexible lower electrode 363, a polymer dielectric film 365 and an upper electrode 366 are sequentially stacked on the upper surface of the substrate 361 provided with this concave portion 362 and the upper surface of the upper electrode 366 on the uppermost surface has a spherical shape which will be provided with a predetermined curvature radius R.

In that case, a transducer cell 367 is formed by the portion opposite to the lower electrode 363.

And, applying a drive signal to the upper electrode 366 and the lower electrode 363, flexible polymer dielectric film 365 provided between them is vibrated and thereby it is made possible to generate ultrasonic waves.

Also in the present embodiment, likewise the eleventh embodiment, the upper surface of the upper electrode 366 is spherically shaped, and therefore in the case of applying drive signals simultaneously to each transducer cell 367, spherically shaped ultrasonic wavefront is formed and structurally the ultrasonic beam can be focused at the focusing point F.

Therefore, according to the present eleventh embodiment, ultrasonic waves can be focused in simple structure and ultrasonic received signal with good S/N can be obtained.

In addition, the configuration for obtaining an ultrasonic cross-sectional image can be simplified by a large margin.

In addition, the present embodiment provides the opposite side of the surface on the side to transmit ultrasonic waves with small concave portions 362, making it possible to reduce crosstalk between the adjacent transducer cells 367 to drive each transducer cell 367. In addition, providing the concave portion 362, it is possible to make acoustic impedance get closer to the value on a living subject.

The capacitive ultrasonic transducer element 312C shown in FIG. 44C can be fabricated according to an explanatory diagram of a fabrication process shown in FIGS. 44A and 44B.

Next, with reference to FIGS. 44A and 44B, fabrication steps of this capacitive ultrasonic transducer element 312C will be described. As shown in FIG. 44A, gap portions 362 are formed in the predetermined distance by silicon resin and the like and the upper surface thereof is provided with a lower electrode 363. In addition, since the upper surface of this lower electrode 363 is used for mounting, a stacked product is prepared by sequentially bonding respectively flexible polymer dielectric film 365 and an upper electrode 366.

Here, polymer dielectric film 365 may be resin such as PVDF (polyvinylidene-fluoride) and the like showing high dielectric with high dielectric inorganic powder being dispersed. In addition, a substrate 361 may comprise flexible resin such as silicon resin and the like being caused to contain mixture of increasing ultrasonic dumping effect such as tungsten.

Next, means or a process to make a variation simple is carried out. That is, in order to fix in an easily bent-processible state or in a state of having undergone a bent-process, as shown in FIG. 44A, small notched concave portions 364 and 368 are respectively formed in predetermined distance on bottom surface sides of polymer dielectric film 365 and the flexible substrate 361.

And, as shown in FIG. 44B, the bottom surface of polymer dielectric film 365 is fixed with adhesive and the like onto the lower electrode 369 on the upper surface of the flexible substrate 361 and thereafter as shown in FIG. 44C, the bottom surface of the substrate 361 is fixed with adhesive and the like in a state that the bottom surface of the substrate 361 is pushed onto the spherically shaped upper surface of a rigid base 360. Thus, as shown in FIG. 44C, a spherical capacitive ultrasonic transducer element 312C can be fabricated.

In addition, adopting such a base 360 being different in spherical curvature radius, a product with a different focusing point F can be simply fabricated as well.

Here, in the above described description, the substrate 361 is fixed on the rigid base 360, and thereby the capacitive ultrasonic transducer element 312C is formed spherically, but as shown in FIG. 44C, the concave portions 364 and 368 may be filled with a filling substance 369 such as adhesive and the like in a bent state so as to be fixed in a spherically bent state. In addition, the both of them may be used together. Here, besides the spherically shaped case, fixity may take place subjected to non-spherical deformation.

Next, with reference to FIGS. 45A to 45D, a method of fabricating a first variation of a capacitive ultrasonic transducer element 12D will be described.

Figure 45A:
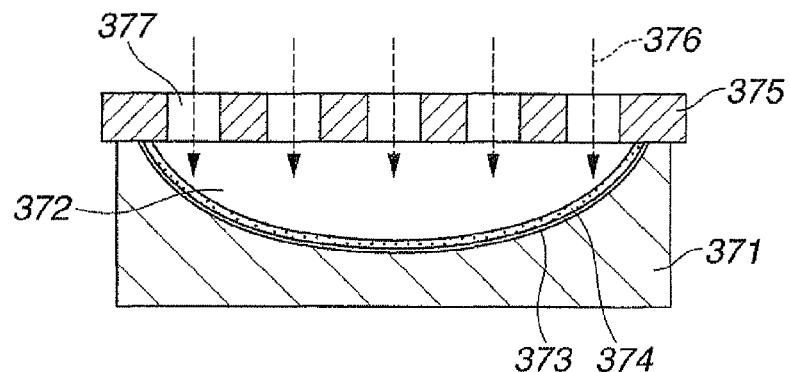
FIG. 45A is an explanatory diagram of a production process of a lower electrode and a photoresist of a capacitive ultrasonic transducer element in a first modified example.

As shown in FIG. 45A, forming a substantially spherical or similar non-spherically shaped concave portion 372 on the upper surface of a rigid substrate 371 with boring processing, a lower electrode 373 and film of photoresist 374 are formed on the front surface of this concave portion 372.

Next, as shown in this FIG. 45R, in a state that a photomask 375 is disposed on the upper surface of this substrate 371, parallel light 376 is radiated onto this photomask 375 from above to expose photoresist 374.

This photomask 375 is provided with a photomask pattern optically transparent portion 377 allowing light to pass through two dimensionally in predetermined distance and the photoresist 374 subjected to radiation of light 376 that has passed this photomask pattern optically transparent portion 377 changes its property being resistant to ion etching (Deep RIE).

Figure 45B:
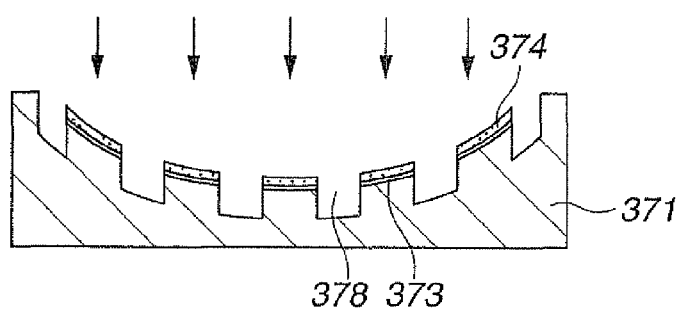
FIG. 45B is an explanatory diagram showing a production process of air gap sections of the capacitive ultrasonic transducer element in the first modified example.
Figure 45C:
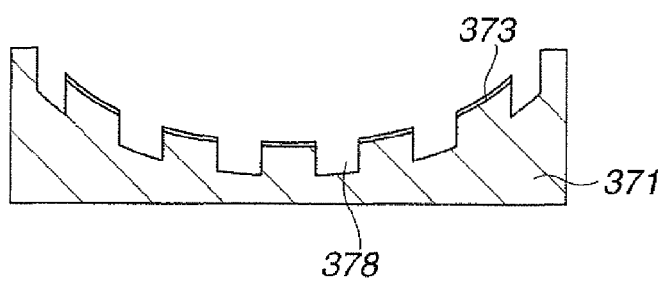
FIG. 45C is an explanatory diagram of a production process of photoresist removal of the capacitive ultrasonic transducer element in the first modified example.

Next as shown in FIG. 45B, ion etching is carried out so that the unexposed photoresist 374 and the lower electrode 373 undergo etching to reach in addition, immediately below the substrate 371 in its inside, and small indentations or gaps 378 are formed two dimensionally and in predetermined distance and the like in the portion of the substrate 371. Thereafter, as shown in FIG. 46C, photoresist 374 is removed.

Figure 45D:
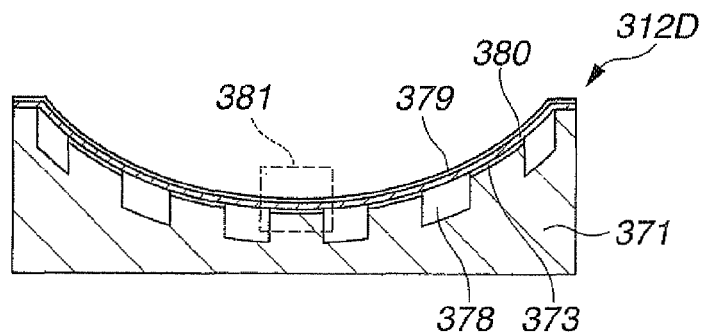
FIG. 45D is an explanatory diagram showing a production process of bonding a membrane with an upper electrode of the capacitive ultrasonic transducer element in the first modified example.

Next as shown in FIG. 45D, on the upper surface of the lower electrode 378 subjected to removal of the photoresist 374, a flexible sheet provided with an upper electrode 379 thereon so as to cover this upper surface in its entirety, specifically a membrane 380 configured by polyimide film and the like is mounted with bonding and the like and thereby a capacitive ultrasonic transducer element 312D is fabricated.

In that case, heating polyimide film configuring the membrane 380, and applying voltage, polyimide film and the lower electrode 373 on the upper surface of the convex substrate 371 can be brought into bonding.

In this capacitive ultrasonic transducer element 312D, a transducer cell 381 is formed in the portion where lower electrode 373 is provided.

The present variation gives rise to operation and effects approximately likewise the capacitive ultrasonic transducer element 312C in FIG. 44C.

Next, structure of a capacitive ultrasonic transducer element 312E of a second variation and a method of fabricating it will be described with reference to FIGS. 46A to 46D.

Figure 46A:
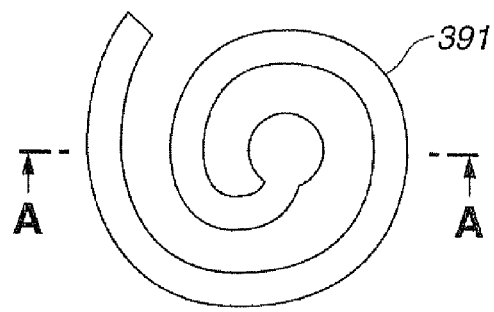
FIG. 46A is an explanatory diagram showing a production process of a spiral transducer body element of a capacitive ultrasonic transducer element in a second modified example.

At first, as shown in FIG. 46A, a convoluted capacitive ultrasonic transducer main body element (abbreviated as transducer main body element) 391 is fabricated. This transducer main body element 391 has transducer cells longitudinally formed along the direction of convolution.

Figure 46B:
FIG. 46B is a sectional view taken along line A-R in FIG. 46A in the second modified example.
Figure 46C:
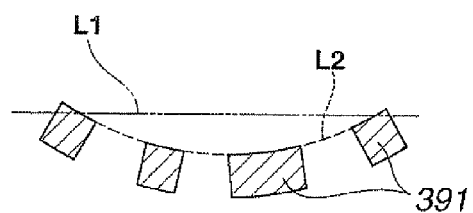
FIG. 46C is an explanatory diagram of a production process of transforming the transducer body element in FIG. 46A into a spherical form in the second modified example.

Showing FIG. 46A with a sectional view along an A-A line, a sectional shape as in FIG. 46B will be obtained. FIG. 46B does not show interior structure, but as that structure, sectional structure of the transducer cell 367 in FIG. 44C, for example, or sectional structure of the transducer cell 381 in FIG. 45D may be adopted.

Next, the convoluted transducer main body element 391 undergoes deformation processing as shown FIG. 46C by pushing the bottom surface side, for example, from above with a spherical member. That is, in FIG. 46C, an upper surface shape L1 prior to deformation indicated by two-dot chain line is deformed to an upper surface shape L2 after deformation indicated by a dotted line.

Figure 46D:
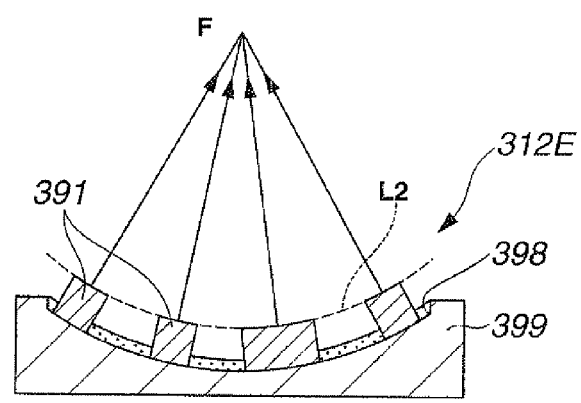
FIG. 46D is an explanatory diagram of a production process of producing the capacitive ultrasonic transducer element, which is arranged vorticosely along a spherical surface, in the second modified example.

And, for example, adhesive 398 is poured into the gap portion in the convolution and the like, a capacitive ultrasonic transducer element 312E disposed convolution-like along the spherical surface as shown in FIG. 46D is fabricated.

Here, the capacitive ultrasonic transducer element 312E shown in FIG. 46D has the bottom surface side being fixed to the spherical surface of a base 399 with adhesive 398, but such structure may be adopted that adhesive 398 and the base 399 are not bonded.

That is, at the time of fixing with adhesive 398, in use of a base 399 formed with a member being easily delaminated to adhesive 398, after adhesive 398 is solidified, the base 399 may be removed.

In the thus fabricated convoluted capacitive ultrasonic transducer element 312E, each part of the convoluted shape is arranged along the spherical surface in structure, and therefore as shown in FIG. 46D, the structure has function to focus an ultrasonic beam to a focusing point F.

Accordingly, the present variation also has operation and effects approximately likewise the twelfth embodiment.

According to the eleventh and the twelfth embodiments of the present invention described above, the capacitive ultrasonic transducer itself is shaped spherically and the like, thereby focusing means that can focus the transmitted and received ultrasonic beam structurally are formed and a received signal with good S/N is obtained.

It goes without saying that, besides a capacitive ultrasonic probe, a capacitive ultrasonic probe apparatus and an ultrasonic diagnostic apparatus using them, the present invention is applicable also to an ultrasonic endoscope diagnostic apparatus in combination of an electronic endoscope apparatus and an ultrasonic diagnostic apparatus to be designed to obtain an endoscopic image and an ultrasonic image simultaneously.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capacitive ultrasonic probe comprising:
one or more capacitive ultrasonic transducer cells;
an impedance matching portion adapted to match an acoustic impedance of a tissue, and an acoustic impedance of one or more of the capacitive ultrasonic transducer cells, the impedance matching portion being arranged with intervening between a membrane, which is a component of the capacitive ultrasonic transducer cell, and the tissue which is an object, and comprising at least one layer of acoustic matching layer which performs impedance matching between an apparent acoustic impedance of the membrane at the time of seeing the membrane as a sound medium, and the acoustic impedance of the tissue;
a capacitive ultrasonic transducer; and
a sheath which includes the capacitive ultrasonic transducer,
wherein the impedance matching portion is arranged on an inner wall on a side of the sheath so as to be separated from the capacitive ultrasonic transducer.

2. The capacitive ultrasonic probe according to claim 1, wherein an ultrasonic transmission medium intervenes between a surface of the capacitive ultrasonic transducer, and inside surface of the sheath.

3. The capacitive ultrasonic probe according to claim 1, having structure of an air layer intervening between the impedance matching portion and a membrane.

4. The capacitive ultrasonic probe according to claim 3, wherein Helmholtz resonator structure having a hole on the membrane is disposed between the impedance matching portion and a membrane.

5. The capacitive ultrasonic probe according to claim 1, wherein the impedance matching portion is means of changing the apparent acoustic impedance of the membrane.

6. The capacitive ultrasonic probe according to claim 5, wherein the means of changing the apparent acoustic impedance of the membrane is a sound medium arranged between an upper electrode and a lower electrode.

7. The capacitive ultrasonic probe according to claim 6, wherein the sound medium arranged between an upper electrode and a lower electrode has an acoustic impedance having a value of 0.5 to 3.0 Mrayl.

8. A capacitive ultrasonic probe comprising:
a capacitive ultrasonic transducer comprising:
a membrane adapted to transmit and receive ultrasonic waves by vibration, the membrane comprising a focusing section having a hemispheroidal structure adapted to focus ultrasonic waves transmitted from the membrane and obtain ultrasonic waves with higher acoustic pressure; and
a plurality of annular electrodes formed concentrically on a surface of the focusing section of the membrane, wherein the annular electrodes are adapted to be driven in different timing, respectively.

9. The capacitive ultrasonic probe according to claim 8, wherein the focusing section is formed by a spherical membrane section which is formed by a membrane section having a spherical surface, the spherical membrane section being arranged in a cavity constructed by a first substrate in which a concavity is formed, and a second substrate arranged so as to plug an opening portion of the concavity.

10. The capacitive ultrasonic probe according to claim 9, wherein a spiral electrode is formed on a surface of the spherical membrane section.

11. The capacitive ultrasonic probe according to claim 9, having at least one layer of acoustic matching layer in an ultrasonic transmitting surface side.

12. The capacitive ultrasonic probe according to claim 9, wherein two or more vent holes are provided in the spherical membrane section.

13. The capacitive ultrasonic probe according to claim 9, enabling to form a focal point obtained by synthesizing a fixed focal point by making the membrane section into a curvature, and a variable focal point obtained by controlling timing of applying a drive voltage to each capacitive ultrasonic transducer element which constructs the capacitive ultrasonic transducer.

14. A capacitive ultrasonic probe comprising:
one or more capacitive ultrasonic transducer cells; and
an impedance matching portion adapted to match an acoustic impedance of a tissue, and an acoustic impedance of one or more of the capacitive ultrasonic transducer cells, the impedance matching portion being provided in a cavity which is a component of the capacitive ultrasonic transducer cell, and being a multi-fine elastic pillar,
wherein the impedance matching portion is means of changing an apparent acoustic impedance of the membrane at the time of seeing the membrane as a sound medium.

15. The capacitive ultrasonic probe according to claim 14, wherein conductive films are uniformly formed on surfaces of the multi-fine elastic pillar.

16. The capacitive ultrasonic probe according to claim 14, wherein the impedance matching portion has a distribution characteristic in an acoustic impedance within a surface of the capacitive ultrasonic transducer cell.

17. The capacitive ultrasonic probe according to claim 14, wherein the means of changing the apparent acoustic impedance of the membrane is a sound medium arranged between an upper electrode and a lower electrode.

18. The capacitive ultrasonic probe according to claim 17, wherein the sound medium arranged between the upper electrode and the lower electrode has an acoustic impedance having a value of 0.5 to 3.0 Mrayl.

19. A capacitive ultrasonic probe comprising:
one or more capacitive ultrasonic transducer cells; and
an impedance matching portion adapted to match an acoustic impedance of a tissue, and an acoustic impedance of one or more of the capacitive ultrasonic transducer cells, the impedance matching portion being arranged with intervening between a membrane, which is a component of the capacitive ultrasonic transducer cell, and the tissue which is an object, and comprising at least one layer of acoustic matching layer which performs impedance matching between an apparent acoustic impedance of the membrane at the time of seeing the membrane as a sound medium, and the acoustic impedance of the tissue;
wherein the impedance matching portion includes a plurality of acoustic impedance adjustment columns in a cavity formed inside the membrane, and has a distribution characteristic in an acoustic impedance within a surface of the capacitive ultrasonic transducer cell.

20. A capacitive ultrasonic probe comprising:
one or more capacitive ultrasonic transducer cells; and
an impedance matching portion adapted to match an acoustic impedance of a tissue, and an acoustic impedance of one or more of the capacitive ultrasonic transducer cells, the impedance matching portion being arranged with intervening between a membrane, which is a component of the capacitive ultrasonic transducer cell, and the tissue which is an object, and comprising at least one layer of acoustic matching layer which performs impedance matching between an apparent acoustic impedance of the membrane at the time of seeing the membrane as a sound medium, and the acoustic impedance of the tissue,
wherein the impedance matching portion comprises a sheet-shaped concavoconvex protective film horn.

21. A capacitive ultrasonic probe comprising:
one or more capacitive ultrasonic transducer cells; and
an impedance matching portion adapted to match an acoustic impedance of a tissue, and an acoustic impedance of one or more of the capacitive ultrasonic transducer cells, the impedance matching portion being arranged with intervening between a membrane, which is a component of the capacitive ultrasonic transducer cell, and the tissue which is an object, and comprising at least one layer of acoustic matching layer which performs impedance matching between an apparent acoustic impedance of the membrane at the time of seeing the membrane as a sound medium, and the acoustic impedance of the tissue,
wherein the impedance matching portion comprises two layers, a first layer of the two layers is made of a porous resin, and a second layer of the two layers is made of a homogeneous resin material which is the same material as that of the first layer, but does not include holes.

22. The capacitive ultrasonic probe according to claim 20, wherein the concavoconvex protective film horn is a sheet with folding lines which is arranged on a surface of an ultrasonic transducer element.

23. The capacitive ultrasonic probe according to claim 20, wherein a lower crown portion of the concavoconvex protective film horn is arranged and connected so as to physically contact a center portion of the ultrasonic transducer cell.

24. The capacitive ultrasonic probe according to claim 21, wherein the resin material is any one of a silicone resin, an urethane resin, an epoxy resin, a Teflon resin, and a polyimide resin, or a composite resin using at least two of the silicone resin, the urethane resin, the epoxy resin, the Teflon resin, and the polyimide resin.

* * * * *